US007964200B2

(12) United States Patent
Mrsny et al.

(10) Patent No.: US 7,964,200 B2
(45) Date of Patent: Jun. 21, 2011

(54) METHODS AND COMPOSITIONS FOR IMMUNIZING AGAINST *CHLAMYDIA* INFECTION

(75) Inventors: Randall J. Mrsny, Los Altos Hills, CA (US); Deborah Dean, San Anselmo, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 25 days.

(21) Appl. No.: 11/914,734

(22) PCT Filed: May 17, 2006

(86) PCT No.: PCT/US2006/019232
§ 371 (c)(1),
(2), (4) Date: Aug. 8, 2008

(87) PCT Pub. No.: WO2006/125076
PCT Pub. Date: Nov. 23, 2006

(65) Prior Publication Data
US 2009/0214570 A1    Aug. 27, 2009

Related U.S. Application Data

(60) Provisional application No. 60/682,616, filed on May 18, 2005.

(51) Int. Cl.
*A61K 39/118* (2006.01)
*C12P 21/04* (2006.01)
(52) U.S. Cl. .................. 424/263.1; 424/192.1; 435/69.7
(58) Field of Classification Search .................. None
See application file for complete search history.

(56) References Cited

U.S. PATENT DOCUMENTS

| | | | |
|---|---|---|---|
| 5,458,878 A | 10/1995 | Pastan et al. | |
| 5,512,658 A | 4/1996 | Pastan et al. | |
| 5,602,095 A | 2/1997 | Pastan et al. | |
| 5,668,255 A | 9/1997 | Murphy | |
| 5,696,237 A | 12/1997 | FitzGerald et al. | |
| 5,747,269 A | 5/1998 | Rammensee et al. | |
| 5,807,832 A | 9/1998 | Russell-Jones et al. | |
| 5,824,315 A | 10/1998 | Nag | |
| 5,863,745 A | 1/1999 | Fitzgerald et al. | |
| 5,869,608 A | 2/1999 | Caldwell et al. | |
| 5,917,021 A | 6/1999 | Lee | |
| 5,922,680 A | 7/1999 | Fjellestad-Paulsen et al. | |
| 5,939,598 A | 8/1999 | Kucherlapati et al. | |
| 5,965,406 A | 10/1999 | Murphy | |
| 5,997,856 A | 12/1999 | Hora et al. | |
| 6,007,791 A | 12/1999 | Coombes et al. | |
| 6,022,950 A | 2/2000 | Murphy | |
| 6,051,405 A | 4/2000 | FitzGerald et al. | |
| 6,086,918 A | 7/2000 | Stern et al. | |
| 6,133,229 A | 10/2000 | Gibson et al. | |
| 6,174,529 B1 | 1/2001 | Michael et al. | |
| 6,239,116 B1 | 5/2001 | Krieg et al. | |
| 6,251,392 B1 | 6/2001 | Hein et al. | |
| 6,255,284 B1 | 7/2001 | McGregor et al. | |
| 6,391,296 B1 | 5/2002 | Okano et al. | |
| 6,440,419 B1 | 8/2002 | Hein et al. | |
| 6,488,926 B1 | 12/2002 | Khan et al. | |
| 6,500,641 B1 | 12/2002 | Chen et al. | |
| 6,525,102 B1 | 2/2003 | Chen et al. | |
| 6,573,237 B2 | 6/2003 | Rinella, Jr. | |
| 6,579,854 B1 * | 6/2003 | Mitchell et al. .................. 514/31 |
| 6,613,332 B1 | 9/2003 | Michael et al. | |
| 6,653,292 B1 | 11/2003 | Kreig et al. | |
| 6,699,678 B1 * | 3/2004 | Ohana .......................... 435/7.32 |
| 6,716,623 B2 | 4/2004 | Chen et al. | |
| 6,720,146 B2 | 4/2004 | Stolk et al. | |
| 6,759,241 B1 | 7/2004 | Hone et al. | |
| 7,314,632 B1 * | 1/2008 | Fitzgerald .................. 424/236.1 |
| 7,611,714 B2 * | 11/2009 | Mrsny ......................... 424/190.1 |
| 2004/0152649 A1 | 8/2004 | Krieg | |
| 2009/0214582 A1 | 8/2009 | Dean | |

FOREIGN PATENT DOCUMENTS

| | | |
|---|---|---|
| GB | 2188638 A | 10/1987 |
| WO | WO 86/01533 | 3/1986 |
| WO | WO 90/07861 | 7/1990 |
| WO | WO 91/00360 | 1/1991 |
| WO | WO 91/18088 | 11/1991 |
| WO | WO 92/05793 | 4/1992 |
| WO | WO 92/08802 | 5/1992 |
| WO | WO 93/17715 | 9/1993 |
| WO | WO 94/02506 A1 | 2/1994 |
| WO | WO 94/06827 A1 | 3/1994 |
| WO | WO 94/25060 A1 | 11/1994 |
| WO | WO 94/26900 A2 | 11/1994 |

(Continued)

OTHER PUBLICATIONS

Grigera et al Journal of Virology, vol. 70, p. 8492-8501.*
Allured, A.S. et al., 1986, "Structure of Exotoxin A of Pseudomonas Aeruginosa at 3.0 Angstrom Resolution," Proc. Natl. Acad. Sci., vol. 83:1320-1324.
Amit et al., 1986, "Three-Dimensional Structure of an Antigen-Antibody Complex at 2.8 A Resolution," Science, vol. 233:747-753.
Baehr et al., 1988, "Mapping Antigen Domains Expressed by *Chlamydia trachomatis* Major Outer Membrane Protein Genes," Proc. Natl. Acad. Sci., USA, vol. 85:4000-4004.
Becerra et al., 2003, "CD8+ T-Cell Mediated Tumor Protection by Pseudomonas Exotoxin Fused to Ovalbumin in C57BL/6 Mice," Surgery, vol. 133(4):404-410.

(Continued)

*Primary Examiner* — Larry R Helms
*Assistant Examiner* — Padma V Baskar
(74) *Attorney, Agent, or Firm* — Shweta Chandra; Carol L. Francis; Bozicevic, Field & Francis LLP

(57) ABSTRACT

The present invention relates, in part, to methods and compositions for immunizing against infection by *Chlamydia trachomatis*. The methods and compositions rely, in part, on administering an immunogenic composition comprising one or more peptides derived from *C. trachomatis* major outer membrane protein (MOMP) to a subject to be immunized. In some embodiments, the compositions comprise a chimeric immunogen comprising a receptor binding domain, a translocation domain, and a *Chlamydia trachomatis* antigen. Polynucleotides encoding the chimeric immunogens, expression vectors comprising the polynucleotides, and kits comprising the compositions are also provided.

9 Claims, 14 Drawing Sheets

FOREIGN PATENT DOCUMENTS

Figure 1:
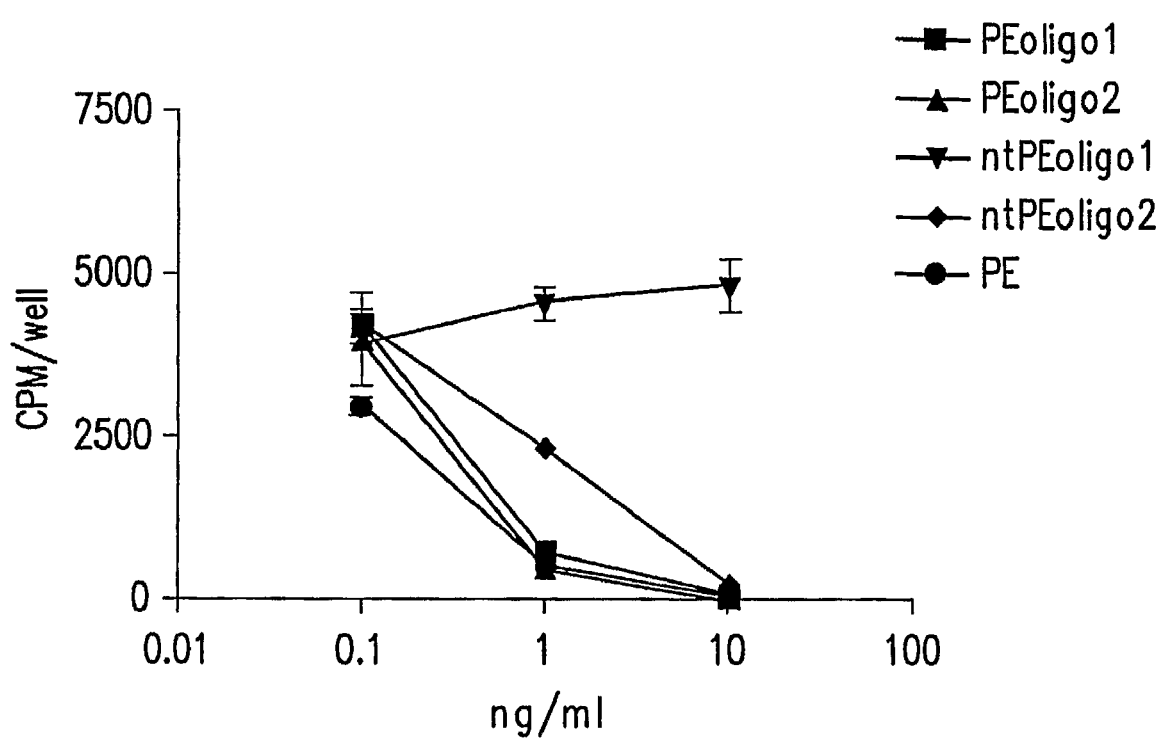

| WO | WO 96/16178 A1 | 5/1996 |
| WO | WO 99/02712 A1 | 1/1999 |
| WO | WO 99/02713 A1 | 1/1999 |
| WO | WO 02/060935 A2 | 8/2002 |
| WO | WO 2007027954 | 3/2007 |

OTHER PUBLICATIONS

Bot et al., 1996, "DNA Immunization of Newborn Mice with a Plasmid-Expressing Nucleoprotein of Influenza Virus," Viral Immunol., vol. 9(4):207-210.

Boyaka et al., 2003, "Therapeutic Manipulation of the Immune System: Enhancement of Innate and Adaptive Mucosal Immunity," Current Pharmaceutical Design, vol. 9:1965-1972.

Buchner et al., 1992, "A Method for Increasing the Yield of Properly Folded Recombinant Fusion Proteins: Single-Chain Immunotoxins from Renaturation of Bacterial Inclusion Bodies," Anal. Biochem., vol. 205:263-270.

Caldwell et al., 1981, "Purification and Partial Characterization of the Major Outer Membrane Protein of *Chlamydia trachomatis*," Infection and Immunity, vol. 31:1161-1176.

Carlson et al., 1989, "Cloning and Characterization of a *Chlamydia trachomatis* L3 DNA Fragment that Codes for an Antigenic Region of the Major Outer Membrane Protein and Specifically Hybridizes to the C- and C-Related—Complex Serovars," Infection and Immunity, vol. 57(2):487-494.

Coombes et al., 2001, "Dendritic Cell Discoveries Provide New Insight into the Cellular Immunobiology of DNA Vaccines," Immunology Letters 3, vol. 78:103-111.

Dean and Powers, 2001, "Persistent *Chlamydia trachomatis* Infections Resist Apoptotic Stimuli," Infection and Immunity, vol. 69(4):2442-2447.

Dean and Millman, 1997, "Molecular and Mutation Trends Analyses of omp1 Alleles for Serovar E of *Chlamydia trachomatis*," J. Clin. Invest., vol. 99:475-483.

Figdor et al., 2003, "Molecular Characterization of Dendritic Cells Operating at the Interface of Innate of Acquired Immunity," Pathol. Biol. (Paris)., vol. 51(2):61-63.

Fitzgerald et al., 1998, "Characterization of V3 Loop-Pseudomonas Exotoxin Chimeras," J. Biol. Chem., vol. 273(16):9951-9958.

Germain et al., 1993, "The Biochemistry and Cell Biology of Antigen Processing and Presentation," Annu. Rev. Immunol., vol. 11:403-450.

Hamilton and Malinowski, 1989, "Nucleoside Sequence of the Major Outer Membrane Protein Gene from *Chlamydia trachomatis* Serovar H," Nucleic Acids Res. 17(20):8366.

Hayes et al., 1995, "Extent and Kinetics of Genetic Change in the omp1 Gene of *Chlamydia trachomatis* in Two Villages with Endemic Trachoma," J. Infect. Dis., vol. 172:268-272.

Hayes et al., 1990, "The Major Outer-Membrane Proteins of *Chlamydia trachomatis* Serovars A and B: Intra-Serovar Amino Acid Changes do not Alter Specificities of Serovar- and C Subspecies-Reactive Antibody-Binding Domains," J. Gen. Microbiol. 136(Pt 8):1559-1566.

Hertle et al., 2001, "Dual-Function Vaccine for Pseudomonas Seruginosa: Characterization of Chimeric Exotoxin A-Pilin Protein," Infection and Immunity, vol. 69(11):6962-6969.

Huse et al., 1988, "Generation of a Large Combinatorial Library of the Immunoglobulin Repertoire in Phage Lambda," Science, vol. 246:1275-1281.

Ishibashi et al., 1993, "Hypercholesterolemia in Low Density Lipoprotein Receptor Knockout Mice and its Reversal by Adenovirus-Mediated Gene Delivery," J. Clin. Invest., vol. 92:883-893.

Ito et al., 1990, "Variation in Virulence Among Oculogenital Serovars of *Chlamydia trachomatis* in Experimental Genital Tract Infection," Infect. Immun., vol. 58(6):2021-2023.

Katz, 1998, "Antigen Presentation, Antigen-Presenting Cells and Antigen Processing," Curr. Opin. Immunol., vol. 1(2):213-219.

Kay et al., 1994, "In Vivo Hepatic Gene Therapy: Complete Albeit Transient Correction of Factor IX Deficiency in Hemophilia B Dogs," Proc. Natl. Acad. Sci. USA, vol. 91:2353-2357.

Kostelny et al., 1992, "Formation of a Bispecific Antibody by the Use of Leucine Zippers," J. Immunol., vol. 148(5):1547-1553.

Kounnas et al., 1992, "The α2-Macroglobulin Receptor/Low Density Lipoprotein Receptor-Related Protein Binds and Internalizes Pseudomonas Exotoxin A," J. Biol. Chem., vol. 267(18):12420-12423.

Lippolis et al., 2000, "Pseudomonas Exotoxin-Mediated Delivery of Exogenous Antigens to MHC Class I and Class II Processing Pathways," Cell. Immunol., vol. 203:75-83.

Lukac et al., 1988, "Toxoid of Pseudomonas Aeruginosa Exotoxin A Generated by Deletion of an Active-Site Residue," Infect. And Immun. vol. 56(12):3095-3098.

Margalit et al., 2003, "Insights from MHC-Bound Peptides," Novartis Found Symp. vol. 254:77-101.

Matsumoto et al., 1998, "Plaque Formation by and Plaque Cloning of *Chlamydia trachomatis* Biovar Trachoma," J. Clin. Microbial, vol. 36(10):3013-3019.

Millman et al., 2001, "Recombination in the ompA Gene but Not the omcB Gene of *Chlamydia* Contributes to Serovar-Specific Differences in Tissue Tropism, Immune Surveillance, and Persistence of the Organism," J. Bacteriol, vol. 183:5997-6008.

Mrsny et al., 1999, "Mucosal Administration of a Chimera Composed of Pseudomonas Exotoxin and the gp120 V3 Loop Sequence of HIV-1 Induces Both Salivary and Serum Antibody Responses," Vaccine, vol. 17:1425-1433.

Mrsny et al., 2002, "Bacterial Toxins as Tools for Mucosal Vaccination," Drug Discovery Today, vol. 7(4):247-258.

Ogata et al., 1990, "Processing of Pseudomonas Exotoxin by a Cellular Protease Results in the Generation of a 37,000-Da Toxin Fragment that is Translocated to the Cytosol," J. Biol. Chem., vol. 265(33):20678-20685.

Ogata, 1991, "Analysis of Pseudomonas Exotoxin Activation and Conformational Changes by Using Monoclonal Antibodies as Probes," Infect. Immun., vol. 59(1):407-414.

Pastan et al., 1992, "Recombinant Toxins as Novel Therapeutic Agents," Annu. Rev. Biochem., vol. 61:331-354.

Peterson et al., 1990, "The Major Outer Membrane Protein Nucleotide Sequence of *Chalamydia trachomatis*, Serovar E," Nucleic Acids Res. vol. 18(1 1):3414.

Pickett et al., 1987, "Complete Nucleotide Sequence of the Major Outer Membrane Protein Gene from *Chlamydia trachomatis* Serovar LI," FEMS Microbiol. Lett. 42:185-190.

Posnett et al., 1988, "A Novel Method of Producing Anti-Peptide Antibodies," J. Biol. Chem., vol. 263(4):1719-1725.

Queen et al., 1989, "A Humanized Antibody that Binds to the Interleukin 2 Receptor," Proc. Natl. Acad. Sci., USA, vol. 86:10029-10033.

Riechmann et al., 1988, "Reshaping Human Antibodies for Theapy," Nature, vol. 332:323-327.

Rodriguez-Maranon et al., 2002, "Prediction of the Membrane-Spanning β-Strands of the Major Outer Membrane Protein of *Chlamydia*," Accession No. MMCWTE, Protein Science, vol. 11:1854-1861.

Sayada et al., 1992, "Complete Sequence of the Major Outer Membrane Protein-Encoding Gene of *Chlamydia trachomatis* Serovar Da," Gene 120:129-130.

Sheikh et al., 2000, "Delivery Systems for Molecular Vaccination," Cur. Opin. Mol. Ther., vol. 2(1):37-54.

Shortman K. et al., 1997, "Dendritic Cells and T Lymphocytes: Developmental and Functional Interactions," Ciba Found Symp., vol. 204:130-138; discussion 138-141.

Sinigaglia et al., 1994, "Defining Rules for the Peptide-MHC Class II Interaction," Curr. Opin. Immunol., vol. 6:52-56.

Stephens et al., 1987, "Diversity of *Chlamydia trachomatis* Major Outer Membrane Protein Genes," J. Bacteriol. 169(9):3879-3885.

Stephens et al., 1998, "Genome Sequence of an Obligate Intracellular Pathogen of Humans: *Chlamydia trachomtis*," Science 282:754-759.

Stephens et al., 1987, "Sequence Analysis of the Major Outer Membrane Protein Gene From *Chlamydia trachomatis* Serovar 12," J. Bacteriol. 168(3):1277-1282.

Stevanovic, 2002, "Structural Basis of Immunogenicity," Transpl. Immunol., vol. 10:133-136.

Stothard et al., 1998, "Phylogenetic Analysis of the *Chlamydia trachomatis* Major Outer Membrane Protein and Examination of Potential Pathogenic Determinants," Infect. Immun. 66(8):3618-3625.
Takahashi, 2003, "Antigen Presentation in Vaccine Development," Comp. Immunol Microbial Infect. Dis., vol. 26:309-328.
Tam, 1988, "Synthetic Peptide Vaccine Design: Synthesis and Properties of a High-Density Multiple Antigenic Peptide System," Proc. Natl., Acad. Sci., USA, vol. 85:5409-5413.
Tam, 1992, "Chemically Defined Synthetic Immunogens and Vaccines by the Multiple Antigen Peptide Approach," Vaccine Research and Developments, vol. 1, Koff and Six, eds., Marcel Deblau, Inc., New York, NY, pp. 51-87.
Tutt et al., 1991, "Trispecific F(ab')3 Derivatives that Use Cooperative Signaling Via the TCR/CD3 Complex and CD2 to Activate and Redirect Resting Cytotoxic T Cells," J. Immunol., vol. 147:60-69.
Vasil et al., 1986, "Molecular Studies of Pseudomonas Exotoxin A Gene," Infect. Immunol., vol. 52:538-548.
Wettendorff et al., 1990, "Modulation of anti-tumor immunity by anti-idiotypic antibodies," Idiotypic Network and Diseases, Cerny and Hiernaux, eds., Am. Soc. Mocrobiol, Washington DC: pp. 203-229.
Yang, 2003, "Generation of Major Histocompatibility Complex Class I Antigens," Microbes and Infection, vol. 5:39-47.
Yuan et al., 1989, "Nucleotide and Deduced Amin Acid Sequences for the Four Variable Domains of the Major Outer Membrane Proteins of the 15 *Chlamydia trachomatis* Serovars," Infect. Immun. vol. 57(4):1040-1049.
Zhang et al., 1990, "The Nucleotide Sequence of Major Outer Membrane Protein Gene of *Chlamydia trachomatis* Serovar F," Nucleic Acids Res. 18(4):1061.
Accession No. B60756, 1997.
Accession No. P08780, 1987.
Accession No. H71484, 1995.
Accession No. H30587, 1989.
Accession No. AY950627, 2005.
Accession No. C30593, 1989.
Accession No. AF414961, 2002.
Accession No. D30593, 1989.
Accession No. AY950635, 2005.
Accession No. E30593, 1989.
Accession No. AF414965, 2002.
Accession No. B30587, 1989.
Accession No. AY950630, 2005.
Accession No. AF063201, 1998.
Accession No. AF063203, 1998.
Accession No. P19542, 1987.
Accession No. AF304858, 2000.
Daugherty, et al. Epithelial application of Pseudomonas aeruginosa exotoxin A results in a selective targeting to cells in the liver, spleen and lymph node. J Control Release. Mar. 1, 2000;65(1-2):297-302.
Gomes, et al. Immunoreactivity and differential developmental expression of known and putative *Chlamydia trachomatis* membrane proteins for biologically variant serovars representing distinct disease groups. Microbes Infect. Mar. 2005;7(3):410-20.
Murdin, et al. Poliovirus hybrids expressing neutralization epitopes from variable domains I and IV of the major outer membrane protein of *Chlamydia trachomatis* elicit broadly cross-reactive C. trachomatis-neutralizing antibodies. Infect Immun. Mar. 1995;63(3):1116-21.
Su, et al. Immunogenicity of a synthetic oligopeptide corresponding to antigenically common T-helper and B-cell neutralizing epitopes of the major outer membrane protein of *Chlamydia trachomatis*. Vaccine. 1993;11(11):1159-66.
Villeneuve, et al. Determination of neutralizing epitopes in variable domains I and IV of the major outer-membrane protein from *Chlamydia trachomatis* serovar K. Microbiology. Sep. 1994;140 ( Pt 9):2481-7.
Zhong and Brunham. Antigenic determinants of the chlamydial major outer membrane protein resolved at a single amino acid level. Infect Immun. Mar. 1991;59(3):1141-7.
Supplementary European Search Report for Application No. 06760091.6, Jan. 27, 2011.

* cited by examiner

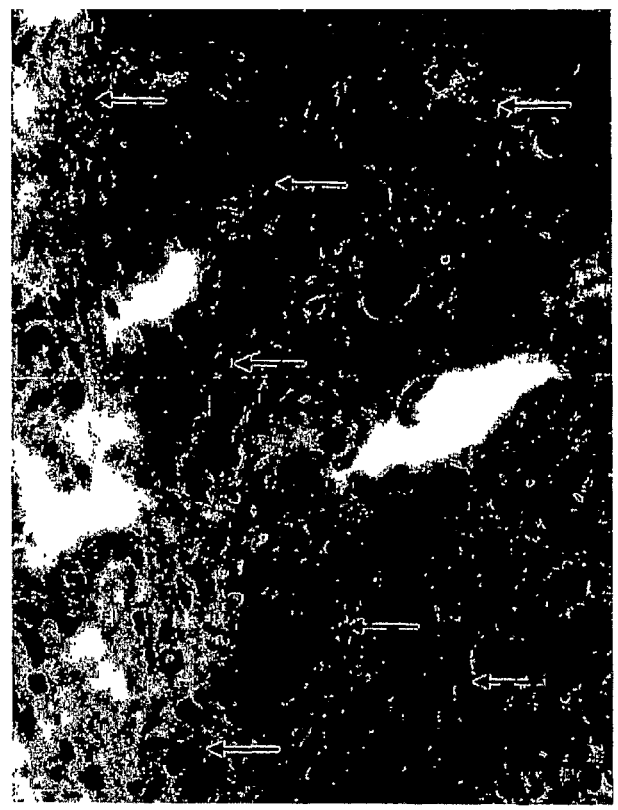
FIG.10B Group B
FIG.10A Group A

*Pseudomonas Aeruginosa* Exotoxin A Amino Acid Sequence

Start of Domain I ↓
1 mhliphwipl vaslgllagg ssasa aeeaf dlwnecakac vldlkdgvrs srmsvdpaia 61 dtngqgvlhy smvleggnda lklaidnals itsdgltirl eggvepnkpv rysytrqarg 121 swslnwlvpi ghekpsnikv fihelnagnq lshmspiyti emgdellakl ardatffvra 181 hesnemqptl aishagvsvv maqtqprrek rwsewasgkv lclldpldgv ynylaqqrcn Start of Domain II ↓
241 lddtwegkiy rvlagnpakh dldikptvis hrlhfpeggs laaltahqac hlpletftrh ⇓ Furin clip site
301 rqpr-gweqle qcgypvqrlv alylaarlsw nqvdqvirna laspgsggdl geaireqpeq Start of Domain III ↓
361 arlaltlaaa eserfvrqgt gndeagaana dvvsltcpva agecagpads gdallernyp 421 tgaeflgdgg dvsfstrgtq nwtverllqa hrqleergyv fvgyhgtfle aaqsivfggv 481 rarsqdldai wrgfyiagdp alaygyaqdq epdargrirn gallrvyvpr sslpgfyrts 541 ltlaapeaag evErlighpl plrldaitgp eeeggrleti lgwplaertv vipsaiptdp 601 rnvggdldps sipdkeqais alpdyasqpg kppredlk

METHODS AND COMPOSITIONS FOR IMMUNIZING AGAINST *CHLAMYDIA* INFECTION

This is a U.S. National Stage under 35 U.S.C. §371 of International Patent Application No. PCT/US2006/019232, filed May 17, 2006, and claims benefit under 35 U.S.C. §119(e) of U.S. Provisional Application No. 60/682,616, filed May 18, 2005, each of which are hereby incorporated by reference in its entirety.

1. STATEMENT REGARDING FEDERALLY SPONSORED RESEARCH

This invention was made with government support under grants entitled "Pathogenesis of persistent *C. trachomatis* STDs," SBIR Grant No. R01AI39499, and "Mucosal vaccine for *Chlamydia trachomatis* infection," SBIR Grant No. 5R43AI052500-02, which was awarded by the National Institute of Health, United States Department of Health and Human Services. The U.S. government has certain rights in this invention.

2. FIELD OF THE INVENTION

The present invention relates, in part, to methods and compositions for immunizing against infection by *Chlamydia trachomatis*. The methods and compositions rely, in part, on administering an immunogenic composition comprising one or more peptides derived from *C. trachomatis* major outer membrane protein (MOMP) to a subject to be immunized.

3. BACKGROUND

Immunization against bacterial or viral infection has greatly contributed to relief from infectious disease. Generally, immunization relies on administering an inactivated or attenuated pathogen to the subject to be immunized. For example, hepatitis B vaccines can be made by inactivating viral particles with formaldehyde, while some polio vaccines consist of attenuated polio strains that cannot mount a full-scale infection. In either case, the subject's immune system is stimulated to mount a protective immune response by interacting with the inactivated or attenuated pathogen. See, e.g., Kuby, 1997, *Immunology* W.H. Freeman and Company, New York.

This approach has proved successful for immunizing against a number of pathogens. Indeed, many afflictions that plagued mankind for recorded history have been essentially eliminated by immunization with attenuated or inactivated pathogens. See id. Nonetheless, this approach is not effective to immunize against infection by many pathogens that continue to pose significant public health problems. In particular, no vaccine presently exists that has been approved for immunization against *C. trachomatis* infection. The absence of such a vaccine presents significant public health problems.

For example, *C. trachomatis* infection is the most common sexually transmitted disease (STD) worldwide, with more than 500 million people throughout the world infected each year, approximately 4 million of which occur in the United States. See Jones and Batteiger, 2000, *Principles and Practice of Infectious Diseases*, Mandell, Bennett and Dolin R, eds., Churchill Livingstone, Philadelphia, pp. 1986-1989. The U.S. Centers for Disease Control and Prevention (CDC) estimates that these infections result in an estimated cost to Americans of $2 billion a year. About 75% of women and 50% of men infected with *C. trachomatis* are asymptomatic, resulting in large populations of untreated individuals. See Karam et al., 1986, *J Infect Dis* 154:900-3. Up to 40% of women with untreated *C. trachomatis* infection will develop pelvic inflammatory disease (PID). Because PID can cause scarring of the fallopian tubes, 20% of infected women will become infertile, 18% will experience debilitating, chronic pelvic pain and 9% will have a life-threatening ectopic pregnancy. If a pregnant woman becomes infected with *C. trachomatis* and is not treated, her baby has a 50% chance of developing conjunctivitis and a 20% chance of pneumonia. Very recently, *C. trachomatis* infection has also been identified as a risk factor for invasive squamous-cell carcinoma of the uterine cervix and a complicating factor in HIV-1 infection. See Koskela et al., 2000, *Int J Cancer* 85:35-9 and Kimani et al., 1996, *J Infect Dis* 173:1437-44.

When *C. trachomatis* infection is detected, antibiotic therapy can usually effectively eliminate the infection. However, these therapies do not always resolve persistent infections or affect established pathologies, such as autoimmunity. See Dean et al, 2000, *J. Infect. Dis.* 182:909-916. Further, issues related to unnecessary antibiotic use and costs associated with frequently screening asymptomatic individuals in an effort to decrease transmission make a compelling argument for developing systems for inducing protective immune responses. Over three decades of efforts to protect individuals from *C. trachomatis* infection, however, have been unsuccessful. See, e.g., Stagg, 1998, *Mol Med Today* 4:166-73 and Beagley, 2000, *J Reprod Immunol* 48:47-68. Thus, there remains an unmet need for methods and compositions that can immunize against *C. trachomatis* infection. These and other unmet needs are provided by the present invention.

4. SUMMARY OF THE INVENTION

In certain aspects, the present invention relates to antigens that comprise amino acid sequences from *C. trachomatis* MOMP. The antigens are useful, for example, for inducing an immune response specific for polypeptides comprising the *C. trachomatis* MOMP sequences that is effective to reduce or prevent *C. trachomatis* adherence to epithelial cells. Preferably, the immune response specific for polypeptides comprising the *C. trachomatis* MOMP sequences is effective to reduce or prevent *C. trachomatis* infection.

Accordingly, in certain embodiments, the invention provides a *C. trachomatis* antigen comprising a sequence according to Formula I. In certain embodiments, the *C. trachomatis* antigen is a sequence according to Formula I:

$$X_{aa1}\text{-}X_{aa2}\text{-}X_{aa3}\text{-}X_{aa4}\text{-}X_{aa5}\text{-}X_{aa6}\text{-}X_{aa7}\text{-}X_{aa8}\text{-}X_{aa9}\text{-}$$
$$X_{aa10}\text{-}X_{aa11}\text{-}X_{aa12}\text{-}X_{aa13}\text{-}X_{aa14}\text{-}X_{aa15}\text{-}X_{aa16}\text{-}$$
$$X_{aa17}\text{-}X_{aa18}\text{-}X_{aa19}\text{-}X_{aa20}\text{-}X_{aa21}\text{-}X_{aa22}\text{-}X_{aa23}\text{-}$$
$$X_{aa24}\text{-}X_{aa25}\text{-}X_{aa26}\text{-}X_{aa27}, \quad \text{Formula I}$$

wherein $X_{aa1}$ is A, V, or absent; $X_{aa2}$ is E, T, K, or absent; $X_{aa3}$ is A, T, P, or absent; $X_{aa4}$ is I, V, or absent; $X_{aa5}$ is F, L, V, or absent; $X_{aa6}$ is D or absent; $X_{aa7}$ is V, T, I, or absent; $X_{aa8}$ is T; $X_{aa9}$ is T; $X_{aa10}$ is L; $X_{aa11}$ is N; $X_{aa12}$ is P or R; $X_{aa13}$ is T; $X_{aa14}$ is T or I; $X_{aa15}$ is A or T; $X_{aa16}$ is G; $X_{aa17}$ is A, C, K, or absent; $X_{aa18}$ is G or absent; $X_{aa19}$ is S, G, T, A, E, D, or absent; $X_{aa20}$ is V or absent; $X_{aa21}$ is A, V, I, K, or absent; $X_{aa22}$ is A, G, S, T, or absent; $X_{aa23}$ is A, G, N, S, or absent; $X_{aa24}$ is G, N, or absent; $X_{aa25}$ is A, S, T, or absent; $X_{aa26}$ is D, E, or absent; and $X_{aa27}$ is G, N, or absent (SEQ ID NO.:42).

In certain embodiments, the invention provides a *C. trachomatis* antigen comprising a sequence according to Formula II. In certain embodiments, the *C. trachomatis* antigen is a sequence according to Formula II:

$$X_{aa1}\text{-}X_{aa2}\text{-}X_{aa3}\text{-}X_{aa4}\text{-}X_{aa5}\text{-}X_{aa6}, \quad \text{Formula II}$$

wherein $X_{aa1}$ is A, S; $X_{aa2}$ is G; $X_{aa3}$ is T; $X_{aa4}$ is D or E, $X_{aa5}$ is A or G; and $X_{aa6}$ is A or V (SEQ ID NO.:2).

In certain embodiments, the invention provides a *C. trachomatis* antigen comprising a sequence according to Formula III. In certain embodiments, the *C. trachomatis* antigen is a sequence according to Formula III:

$$X_{aa1}\text{-}X_{aa2}\text{-}X_{aa3}\text{-}X_{aa4}\text{-}X_{aa5}\text{-}X_{aa6}\text{-}X_{aa7}\text{-}X_{aa8}\text{-}X_{aa9}\text{-}$$
$$X_{aa10}\text{-}X_{aa11}\text{-}X_{aa12}\text{-}X_{aa13}\text{-}X_{aa14}\text{-}X_{aa15}\text{-}X_{aa16}\text{-}$$
$$X_{aa17}\text{-}X_{aa18}\text{-}X_{aa19}\text{-}X_{aa20}\text{-}X_{aa21}\text{-}X_{aa22}\text{-}X_{aa23},\quad\text{Formula III}$$

wherein $X_{aa1}$ is G; $X_{aa2}$ is A, D, or E; $X_{aa3}$ is A, E, or K; $X_{aa4}$ is L or P; $X_{aa5}$ is A or T; $X_{aa6}$ is A, G, S, T, or V; $X_{aa7}$ is K, N, R, S, or absent; $X_{aa8}$ is A, D, or absent; $X_{aa9}$ is A, D, I, S, T, or V; $X_{aa10}$ is A, E, G, T, or V; $X_{aa11}$ is D, G, or N; $X_{aa12}$ is L, N, or T; $X_{aa13}$ is A, E, Q, S, or T; $X_{aa14}$ is A, K, N, S, or T; $X_{aa15}$ is A, D, or T; $X_{aa16}$ is L or P; $X_{aa17}$ is K, S, T, or V; $X_{aa18}$ is I, K, T, or V; $X_{aa19}$ is C, L, or N; $X_{aa20}$ is I, T or V; $X_{aa21}$ is A or E; $X_{aa22}$ is R; and $X_{aa23}$ is E, P, or T (SEQ ID NO.:3).

In certain embodiments, the invention provides a *C. trachomatis* antigen comprising a sequence according to Formula IV. In certain embodiments, the *C. trachomatis* antigen is a sequence according to Formula IV:

$$X_{aa1}\text{-}X_{aa2}\text{-}X_{aa3}\text{-}X_{aa4}\text{-}X_{aa5}\text{-}X_{aa6}\text{-}X_{aa7}\text{-}X_{aa8}\text{-}X_{aa9}\text{-}$$
$$X_{aa10}\text{-}X_{aa11}\text{-}X_{aa12}\text{-}X_{aa13}\text{-}X_{aa14}\text{-}X_{aa15}\text{-}X_{aa16}\text{-}$$
$$X_{aa17}\text{-}X_{aa18}\text{-}X_{aa19}\text{-}X_{aa20}\text{-}X_{aa21}\text{-}X_{aa22}\text{-}X_{aa23}\text{-}$$
$$X_{aa24}\text{-}X_{aa25}\text{-}X_{aa26}\text{-}X_{aa27},\quad\text{Formula IV}$$

wherein $X_{aa1}$ is A or V; $X_{aa2}$ is E, T, or K; $X_{aa3}$ is A, T, or P; $X_{aa4}$ is I or V; $X_{aa5}$ is F, L, or V; $X_{aa6}$ is D; $X_{aa7}$ is V, T, or I; $X_{aa8}$ is T; $X_{aa9}$ is T; $X_{aa10}$ is L; $X_{aa11}$ is N; $X_{aa12}$ is P or R; $X_{aa13}$ is T; $X_{aa14}$ is T or I; $X_{aa15}$ is A or T; $X_{aa16}$ is G; $X_{aa17}$ is A, C, or K; $X_{aa18}$ is G; $X_{aa19}$ is S, G, T, A, E, or D; $X_{aa20}$ is V; $X_{aa21}$ is A, V, I, or K; $X_{aa22}$ is A, G, S, or T; $X_{aa23}$ is A, G, N, or S; $X_{aa24}$ is G, N, or absent; $X_{aa25}$ is A, S, or T; $X_{aa26}$ is D or E; and $X_{aa27}$ is G or N (SEQ ID NO.:1).

In certain embodiments, the *C. trachomatis* MOMP sequence is selected from the group consisting of AGTEAA (SEQ ID NO.:4), AGTDAA (SEQ ID NO.:5), AETIFDVTTLNPTIAGAGDVKTSAEG (SEQ ID NO.:6), AETILDVTTLNPTIAGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKPKGYVGKE (SEQ ID NO.:11), ILWEGFGGDPCDPCTT (SEQ ID NO.:12), ALNIWDRFDV (SEQ ID NO.:13), KMKSRKSCGIAVGTTVVSADKYAVT (SEQ ID NO.: 14), CAETIFDVTTLNPTIAGAGDVKTSAEGC (SEQ ID NO.: 15), CAETILDVTTLNPTIAGKGTVVTSAEC (SEQ ID NO.:16), CTTLNPTIAGC (SEQ ID NO.: 17), CGAKPTATTGNATAPSTLTAREC (SEQ ID NO.:18), and CTTSDVAGLQNDPC (SEQ ID NO.:19). In certain embodiments, the *C. trachomatis* antigen is a peptide having one of SEQ ID NOS.: 4-19.

In certain embodiments, the *C. trachomatis* antigen is selected from the group consisting of AGTEAA (SEQ ID NO.:4) and AGTDAA (SEQ ID NO.:5). In certain embodiments, the *C. trachomatis* antigen is selected from the group consisting of AETIFDVTTLNPTIAGAGDVKTSAEG (SEQ ID NO.:6), AETILDVTTLNPTIAGKGTVVTSAE (SEQ ID NO.:7), TTLNPTIAGC (SEQ ID NO.:8), CAETIFDVTTLNPTIAGAGDVKTSAEGC (SEQ ID NO.:15), CAETILDVTTLNPTIAGKGTVVTSAEC (SEQ ID NO.:16), and CTTLNPTIAGC (SEQ ID NO.:17). In certain embodiments, the *C. trachomatis* antigen is selected from the group consisting of GAKPTATTGNATAPSTLTARE (SEQ ID NO.:9), TTSDVAGLQNDPC (SEQ ID NO.: 10), CGAKPTATTGNATAPSTLTAREC (SEQ ID NO.:18), and CTTSDVAGLQNDPC (SEQ ID NO.:19). In certain embodiments, the *C. trachomatis* antigen is selected from the group consisting of SEFTINKPKGYVGKE (SEQ ID NO.:11), ILWEGFGGDPCDPCTT (SEQ ID NO.:12), ALNIWDRFDV (SEQ ID NO.:13), and KMKSRKSCGIAVGTTVVSADKYAVT (SEQ ID NO.:14).

In another aspect, the invention provides a chimeric immunogen for inducing an immune response against *C. trachomatis*. The chimeric immunogens of the invention generally comprise a receptor binding domain, a translocation domain, and one or more antigens heterologous to at least one of the other portions of the chimeric immunogen, as described herein. The chimeric immunogens of the invention can elicit humoral, cell-mediated and mucosal immune responses against the heterologous antigen(s). Such chimeras are useful, for example, in vaccines against infection by organisms for which conventional vaccines are not practical, such as, for example, *C. trachomatis*.

Accordingly, in certain aspects, the invention provides a chimeric immunogen that comprises a receptor binding domain, a translocation domain, and a *C. trachomatis* antigen comprising an amino acid sequence of Formula I, Formula II, Formula III, or Formula IV as defined above. In certain embodiments, the *C. trachomatis* antigen is selected from the group consisting of AGTEAA (SEQ ID NO.:4), AGTDAA (SEQ ID NO.:5), AETIFDVTTLNPTIAGAGDVKTSAEG (SEQ ID NO.:6), AETILDVTTLNPTIAGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKPKGYVGKE (SEQ ID NO.:11), ILWEGFGGDPCDPCTT (SEQ ID NO.: 12), ALNIWDRFDV (SEQ ID NO.:13), KMKSRKSCGIAVGTTVVSADKYAVT (SEQ ID NO.: 14), CAETIFDVTTLNPTIAGAGDVKTSAEGC (SEQ ID NO.:15), CAETILDVTTLNPTIAGKGTVVTSAEC (SEQ ID NO.:16), CTTLNPTIAGC (SEQ ID NO.:17), CGAKPTATTGNATAPSTLTAREC (SEQ ID NO.:18), and CTTSDVAGLQNDPC (SEQ ID NO.:19). In certain embodiments, the *C. trachomatis* antigen is selected from the group consisting of AGTEAA (SEQ ID NO.:4) and AGTDAA (SEQ ID NO.: 5). In certain embodiments, the *C. trachomatis* antigen is selected from the group consisting of AETIFDVTTLNPTIAGAGDVKTSAEG (SEQ ID NO.:6), AETILDVTTLNPTIAGKGTVVTSAE (SEQ ID NO.:7), TTLNPTIAGC (SEQ ID NO.:8), CAETIFDVTTLNPTIAGAGDVKTSAEGC (SEQ ID NO.:15), CAETILDVTTLNPTIAGKGTVVTSAEC (SEQ ID NO.:16), and CTTLNPTIAGC (SEQ ID NO.:17). In certain embodiments, the *C. trachomatis* antigen is selected from the group consisting of GAKPTATTGNATAPSTLTARE (SEQ ID NO.:9), TTSDVAGLQNDPC (SEQ ID NO.: 10), CGAKPTATTGNATAPSTLTAREC (SEQ ID NO.:18), and CTTSDVAGLQNDPC (SEQ ID NO.:19). In certain embodiments, the *C. trachomatis* antigen is selected from the group consisting of SEFTINKPKGYVGKE (SEQ ID NO.:11), ILWEGFGGDPCDPCTT (SEQ ID NO.:12), ALNIWDRFDV (SEQ ID NO.:13), and KMKSRKSCGIAVGTTVVSADKYAVT (SEQ ID NO.:14). In certain embodiments, the chimeric immunogen, when administered to a subject, induces an immune response in the subject that is effective to reduce adherence of a microorganism that expresses the *C. trachomatis* antigen to epithelial cells of the subject. For example, in certain embodiments, the chimeric immunogen, when administered to a subject, induced an immune response that is effective to reduce or prevent adherence of *C. trachomatis* to epithelial cells of the subject.

In another aspect, the invention provides a method for inducing an immune response in a subject that comprises administering to the subject an immunogenic amount of a chimeric immunogen comprising a receptor binding domain, a translocation domain, and a *C. trachomatis* antigen comprising an amino acid sequence of Formula I, Formula II, Formula III, or Formula IV as defined above. In certain embodiments, the *C. trachomatis* antigen comprises an amino acid sequence that is selected from the group consisting of AGTEAA (SEQ ID NO.:4), AGTDAA (SEQ ID NO.:5), AETIFDVTTLNPTIAGAGDVKTSAEG (SEQ ID NO.:6), AETILDVTTLNPTIAGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKPKGYVGKE (SEQ ID NO.:11), ILWEGFGGDPCDPCTT (SEQ ID NO.:12), ALNIWDRFDV (SEQ ID NO.:13), KMKSRKSCGIAVGTTVVSADKYAVT (SEQ ID NO.:14), CAETIFDVTTLNPTIAGAGDVKTSAEGC (SEQ ID NO.:15), CAETILDVTTLNPTIAGKGTVVTSAEC (SEQ ID NO.:16), CTTLNPTIAGC (SEQ ID NO.: 17), CGAKPTATTGNATAPSTLTAREC (SEQ ID NO.:18), and CTTSDVAGLQNDPC (SEQ ID NO.:19). In certain embodiments, administration of the chimeric immunogen can induce an immune response in the subject that is effective to reduce adherence of a microorganism expressing the *C. trachomatis* peptide to epithelial cells of the subject. In certain embodiments, administration of the chimeric immunogen to a subject can induce an immune response in the subject that reduces the severity of *C. trachomatis* infection. In certain embodiments, administration of the chimeric immunogen to a subject can induce an immune response in the subject that can prevent *C. trachomatis* infection.

In yet another aspect, the invention provides a method for generating in a subject antibodies specific for a *C. trachomatis* antigen comprising an amino acid sequence of Formula I, Formula II, Formula III, or Formula IV as defined above. In certain embodiments, the *C. trachomatis* antigen comprises an amino acid sequence that is selected from the group consisting of AGTEAA (SEQ ID NO.:4), AGTDAA (SEQ ID NO.:5), AETIFDVTTLNPTIAGAGDVKTSAEG (SEQ ID NO.:6), AETILDVTTLNPTIAGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKPKGYVGKE (SEQ ID NO.:11), ILWEGFGGDPCDPCTT (SEQ ID NO.:12), ALNIWDRFDV (SEQ ID NO.:13), KMKSRKSCGIAVGTTVVSADKYAVT (SEQ ID NO.: 14), CAETIFDVTTLNPTIAGAGDVKTSAEGC (SEQ ID NO.:15), CAETILDVTTLNPTIAGKGTVVTSAEC (SEQ ID NO.:16), CTTLNPTIAGC (SEQ ID NO.: 17), CGAKPTATTGNATAPSTLTAREC (SEQ ID NO.:18), and CTTSDVAGLQNDPC (SEQ ID NO.:19). In certain embodiments, the method comprises administering to said subject an immunogenic amount of a chimeric immunogen comprising a receptor binding domain, a translocation domain, and a *C. trachomatis* antigen comprising an amino acid sequence of Formula I, Formula II, Formula III, or Formula IV as defined above. In certain embodiments, the *C. trachomatis* antigen comprises an amino acid sequence that is selected from the group consisting of AGTEAA (SEQ ID NO.:4), AGTDAA (SEQ ID NO.:5), AETIFDVTTLNPTIAGAGDVKTSAEG (SEQ ID NO.:6), AETILDVTTLNPTIAGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKPKGYVGKE (SEQ ID NO.:11), ILWEGFGGDPCDPCTT (SEQ ID NO.:12), ALNIWDRFDV (SEQ ID NO.:13), KMKSRKSCGIAVGTTVVSADKYAVT (SEQ ID NO.: 14), CAETIFDVTTLNPTIAGAGDVKTSAEGC (SEQ ID NO.:15), CAETILDVTTLNPTIAGKGTVVTSAEC (SEQ ID NO.:16), CTTLNPTIAGC (SEQ ID NO.: 17), CGAKPTATTGNATAPSTLTAREC (SEQ ID NO.:18), and CTTSDVAGLQNDPC (SEQ ID NO.:19).

In still another aspect, the invention provides a polynucleotide that encodes a chimeric immunogen that comprises a receptor binding domain, a translocation domain, and a *C. trachomatis* antigen comprising an amino acid sequence of Formula I, Formula II, Formula III, or Formula IV as defined above. In certain embodiments, the *C. trachomatis* antigen comprises an amino acid sequence that is selected from the group consisting of AGTEAA (SEQ ID NO.:4), AGTDAA (SEQ ID NO.:5), AETIFDVTTLNPTIAGAGDVKTSAEG (SEQ ID NO.:6), AETILDVTTLNPTIAGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKPKGYVGKE (SEQ ID NO.:11), ILWEGFGGDPCDPCTT (SEQ ID NO.: 12), ALNIWDRFDV (SEQ ID NO.:13), KMKSRKSCGIAVGTTVVSADKYAVT (SEQ ID NO.:14), CAETIFDVTTLNPTIAGAGDVKTSAEGC (SEQ ID NO.:15), CAETILDVTTLNPTIAGKGTVVTSAEC (SEQ ID NO.:16), CTTLNPTIAGC (SEQ ID NO.:17), CGAKPTATTGNATAPSTLTAREC (SEQ ID NO.:18), and CTTSDVAGLQNDPC (SEQ ID NO.:19).

In yet another aspect, the invention provides expression vectors that comprise a polynucleotide of the invention.

In still another aspect, the invention provides cells comprising an expression vector of the invention.

In yet another aspect, the invention provides a composition comprising a chimeric immunogen that comprises a receptor binding domain, a translocation domain, and a *C. trachomatis* antigen comprising an amino acid sequence of Formula I, Formula II, Formula III, or Formula IV as defined above. In certain embodiments, the *C. trachomatis* antigen comprises an amino acid sequence that is selected from the group consisting of AGTEAA (SEQ ID NO.:4), AGTDAA (SEQ ID NO.:5), AETIFDVTTLNPTIAGAGDVKTSAEG (SEQ ID NO.:6), AETILDVTTLNPTIAGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKPKGYVGKE (SEQ ID NO.:11), ILWEGFGGDPCDPCTT (SEQ ID NO.:12), ALNIWDRFDV (SEQ ID NO.:13), KMKSRKSCGIAVGTTVVSADKYAVT (SEQ ID NO.:14), CAETIFDVTTLNPTIAGAGDVKTSAEGC (SEQ ID NO.:15), CAETILDVTTLNPTIAGKGTVVTSAEC (SEQ ID NO.:16), CTTLNPTIAGC (SEQ ID NO.: 17), CGAKPTATTGNATAPSTLTAREC (SEQ ID NO.:18), and CTTSDVAGLQNDPC (SEQ ID NO.:19). In certain embodiments, the composition further comprises a pharmaceutically acceptable diluent, excipient, vehicle, or carrier. In certain embodiments, the composition further comprises a pharmaceutically acceptable adjuvant that can potentiate the immune response induced by the chimeric immunogen.

In another aspect, the invention provides a kit. In certain embodiments, the kit comprises a composition of the invention in more or more containers. In certain embodiments, the composition can be in a unit dosage form, e.g., a tablet, lozenge, capsule, etc. In certain embodiments, the composition can be provided in or with a device for administering the composition, such as, for example, a device configured to administer a single-unit dose of the composition, e.g., an inhaler.

5. BRIEF DESCRIPTION OF THE DRAWINGS

FIG. 1 presents a graphical representation of inhibition of protein synthesis in L929 cells treated with toxic (PE) and nontoxic (ntPE) forms of chimeric immunogens 1 and 2.

Figure 2:
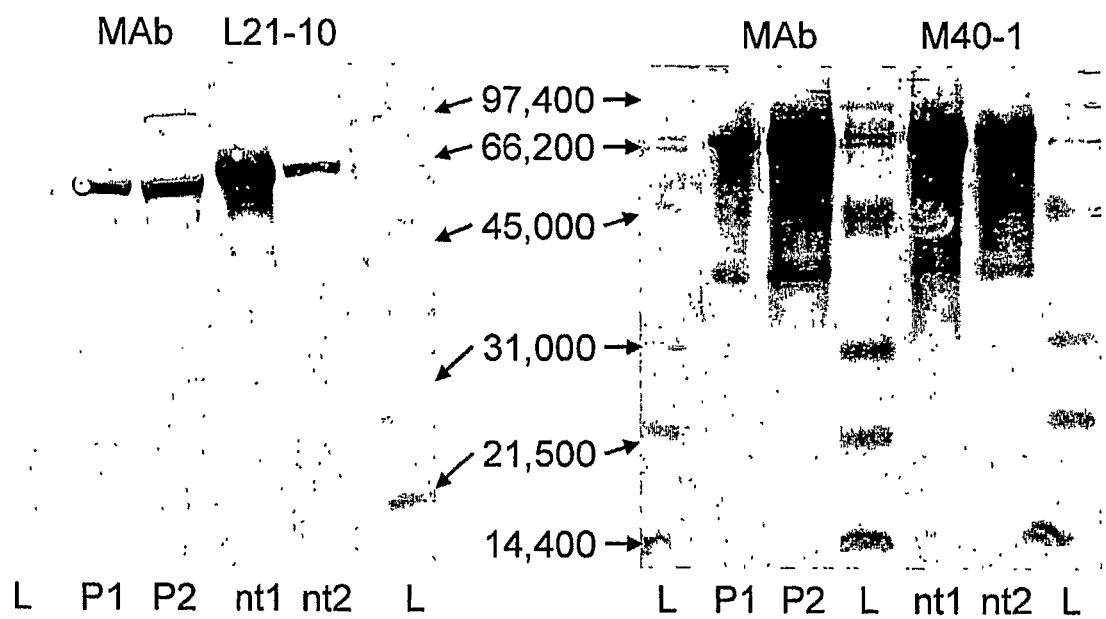

FIG. 2 presents the results of Western blot analysis of toxic and nontoxic forms of chimeric immunogens 1 and 2. Monoclonal antibody L21-10, specific for the VS4 region of all known *C. trachomatis* serovars was used in the Western blot presented in FIG. 2A, while monoclonal antibody M40-1, specific for ntPE was used in the Western blot presented in FIG. 2B. In FIG. 2, L is the molecular weight ladder; P1 is toxic chimeric immunogen 1; P2 is toxic chimeric immunogen 2; nt1 is non-toxic chimeric immunogen 1; nt2 is non-toxic chimeric immunogen 2.

Figure 3A:
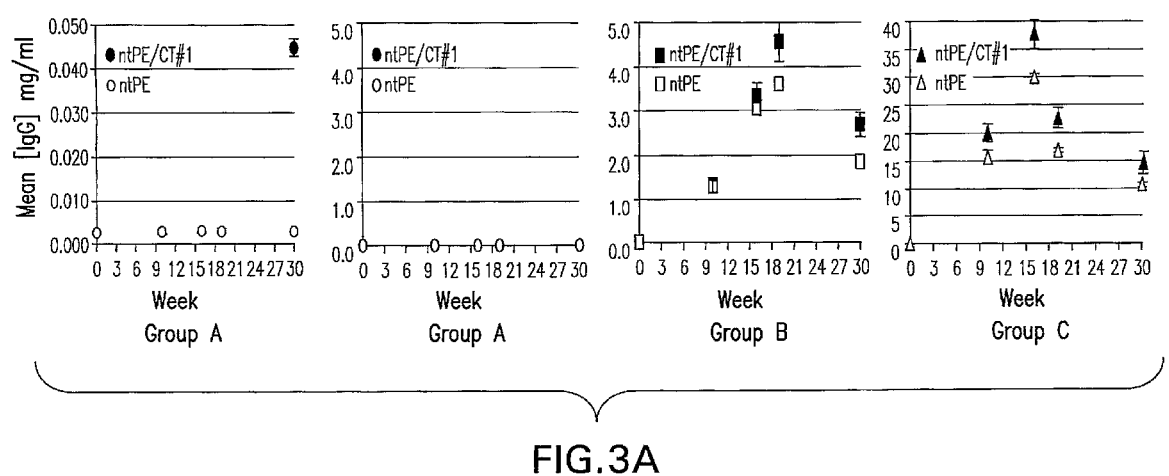
Figure 3B:
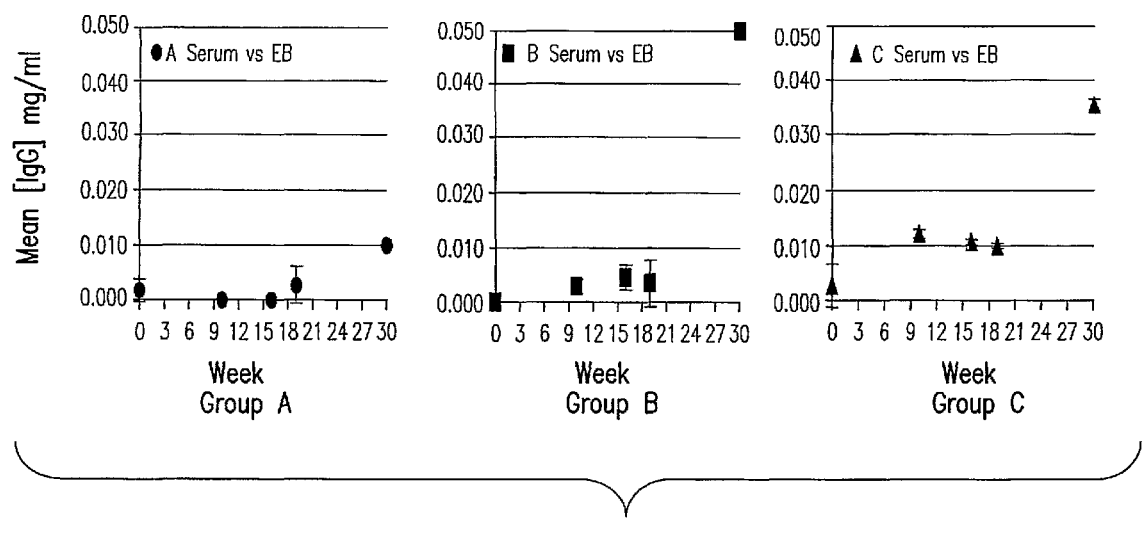

FIG. 3 presents graphical representations of antibody concentrations measured in serum of mice immunized intranasally (IN) with non-toxic *Pseudomonas* exotoxin A without a *C. trachomatis* antigen (ntPE; Group A), IN with chimeric immunogen 1 (Group B), or subcutaneously with chimeric immunogen 1 (Group C). The antibody concentrations were measured using ELISA assays against chimeric immunogen 1 (FIG. 3A) or against *C. trachomatis* elementary bodies (EBs) (FIG. 3B).

Figure 4A:
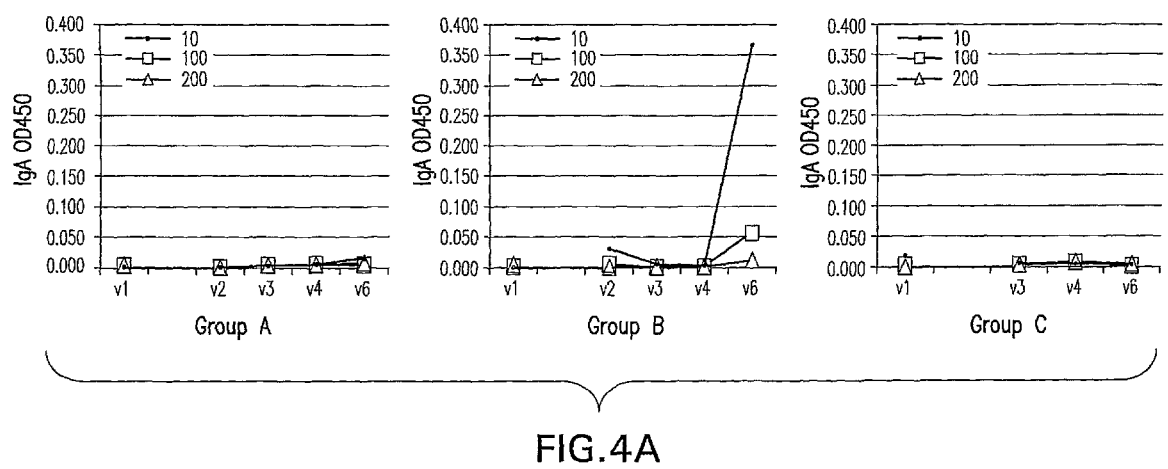
Figure 4B:
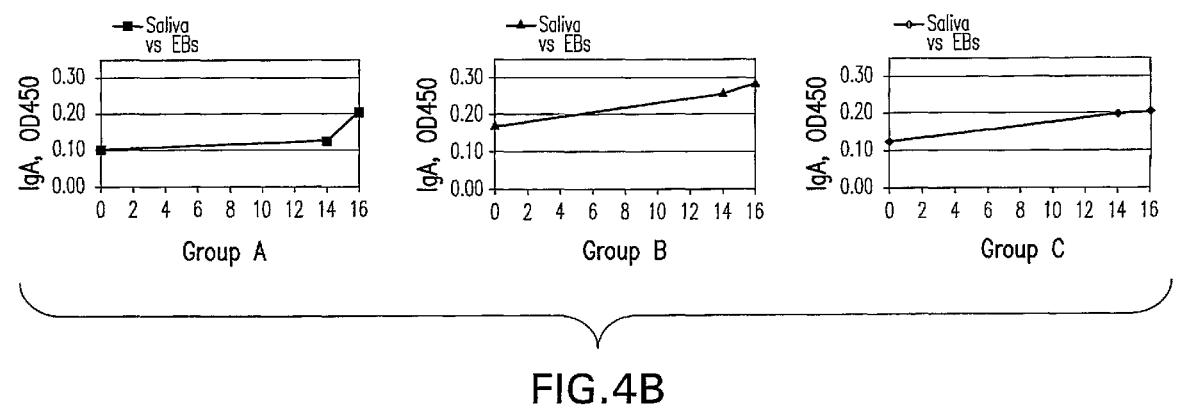

FIG. 4 presents graphical representations of antibody concentrations measured in saliva of mice immunized intranasally (IN) with ntPE (Group A), IN with chimeric immunogen 1 (Group B), or subcutaneously with chimeric immunogen 1 (Group C). The antibody concentrations were measured using ELISA assays against chimeric immunogen 1 (FIG. 4A) or against *C. trachomatis* elementary bodies (EBs) (FIG. 4B).

Figure 5:
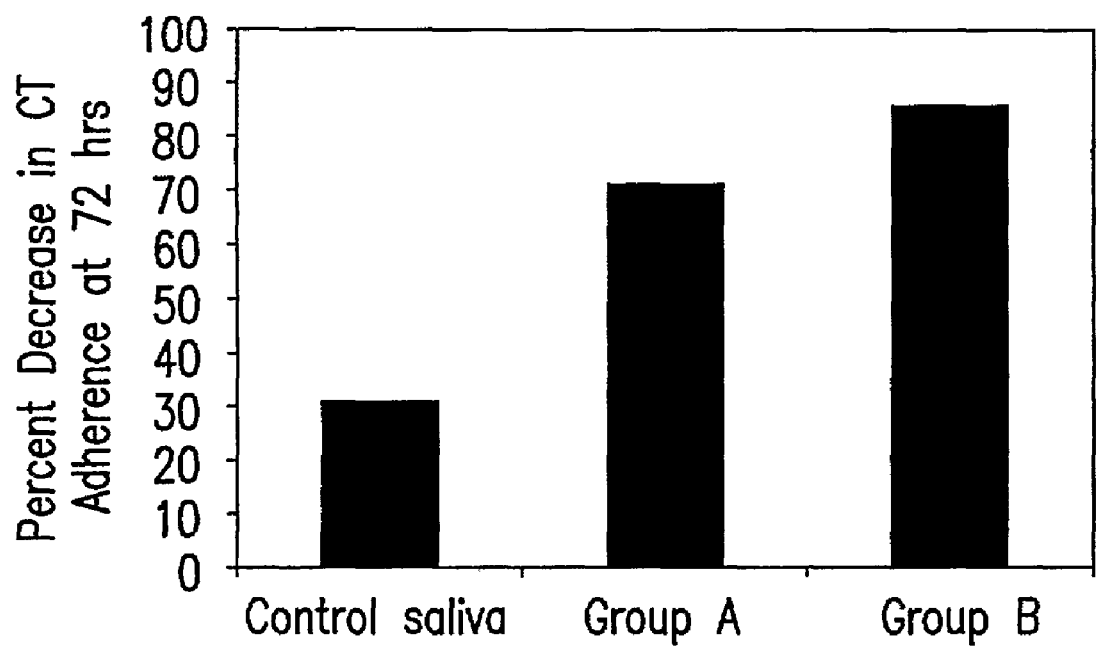

FIG. 5 presents a graphical representation of the ability of saliva isolated from mice immunized IN with ntPE (Group A) or chimeric immunogen 1 (Group B) to inhibit adherence of *C. trachomatis* to A549 cells.

Figure 6A:
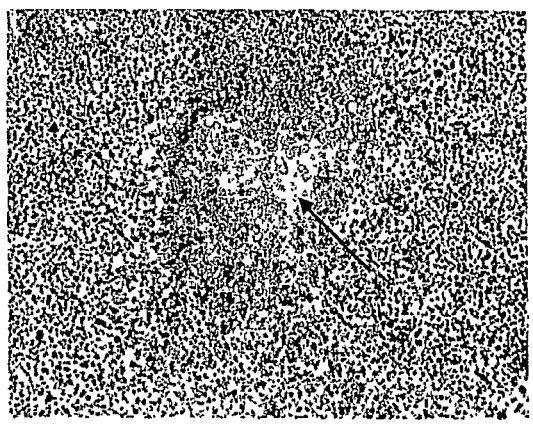
Figure 6B:
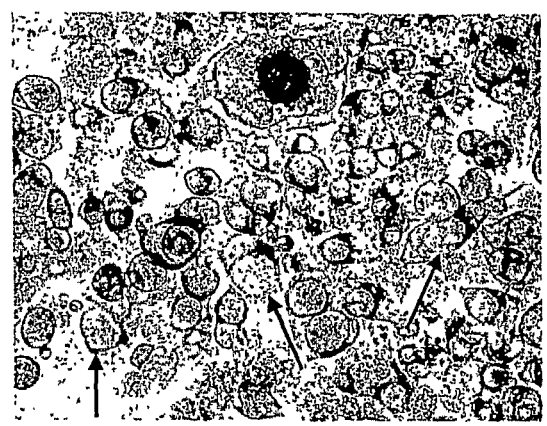

FIG. 6 presents a representative micrograph showing single plaques formed by an individual isolate of a *C. trachomatis* serovar at 100× magnification (FIG. 6A) and 400× magnification (FIG. 6B).

Figure 7B:
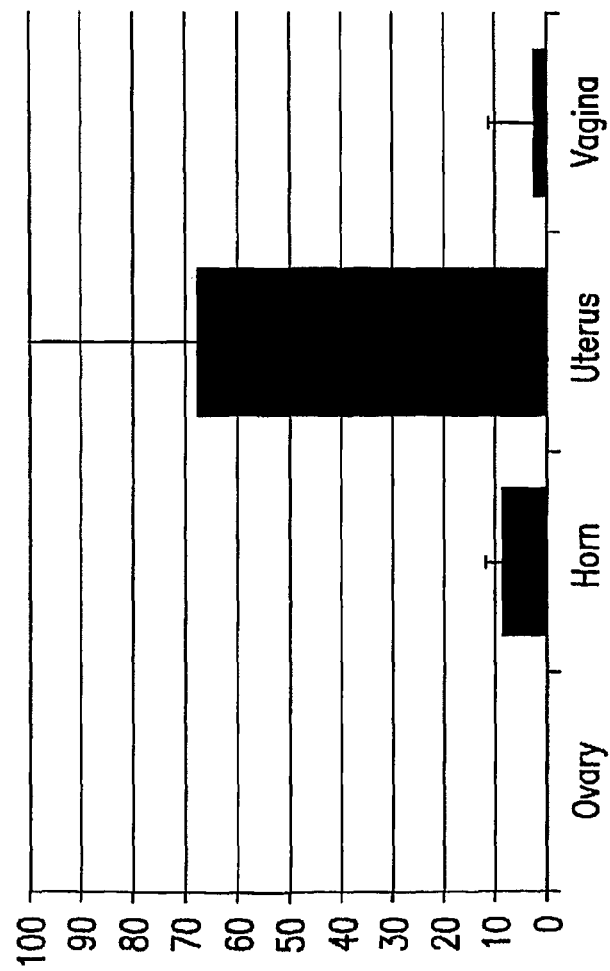
Figure 7A:
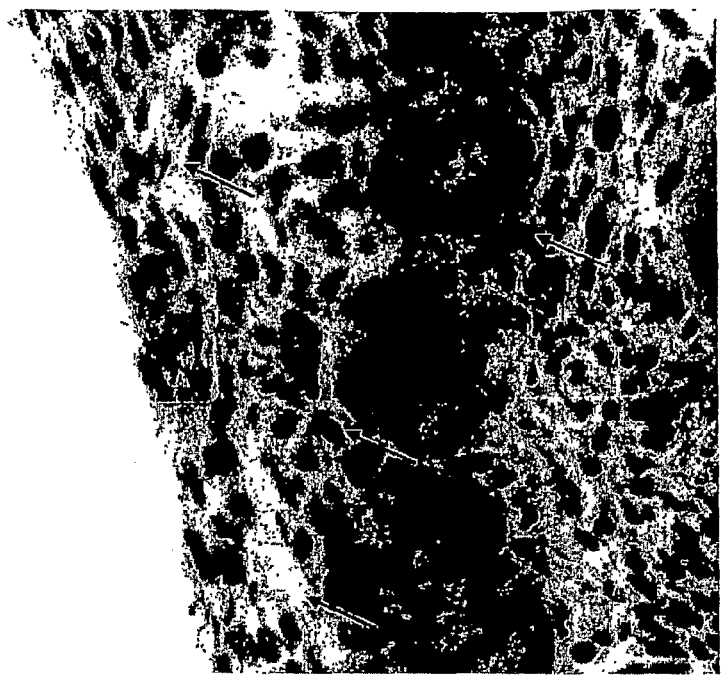

FIG. 7 presents the results of quantitative real-time RT-PCR analysis (FIG. 7A) and immunohistochemical analysis (IHC) (FIG. 7B) of *C. trachomatis* infection of the genital tract of unimmunized mice.

Figure 8C:
Figure 8A:
Figure 8B:
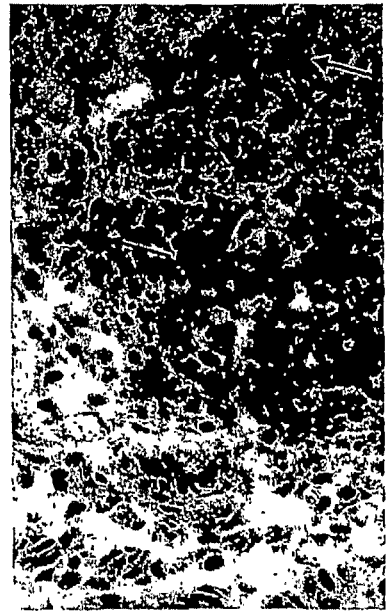

FIG. 8 presents the results of IHC analysis of *C. trachomatis* infection in the uterus of mice immunized IN with ntPE (Group A) (FIGS. 8A and 8B) and immunized IN with chimeric immunogen 1 (FIG. 8C).

Figure 9:

FIG. 9 presents the results of quantitative real-time RT-PCR of *C. trachomatis* infection in the uterus of mice immunized IN with ntPE (Group A) and immunized IN with chimeric immunogen 1 (Group B).

FIG. 10 presents the results of histological analysis with hemolysin and eosin staining of the uterus of mice immunized with ntPE (Group A) or chimeric immunogen 1 (Group B) showing neutrophilic and lymphocytic infiltration into uterine tissue following vaginal challenge with *C. trachomatis* in Group B but not Group A.

FIG. 11 presents an exemplary *Pseudomonas aeruginosa* exotoxin A amino acid sequence.

Figure 12:
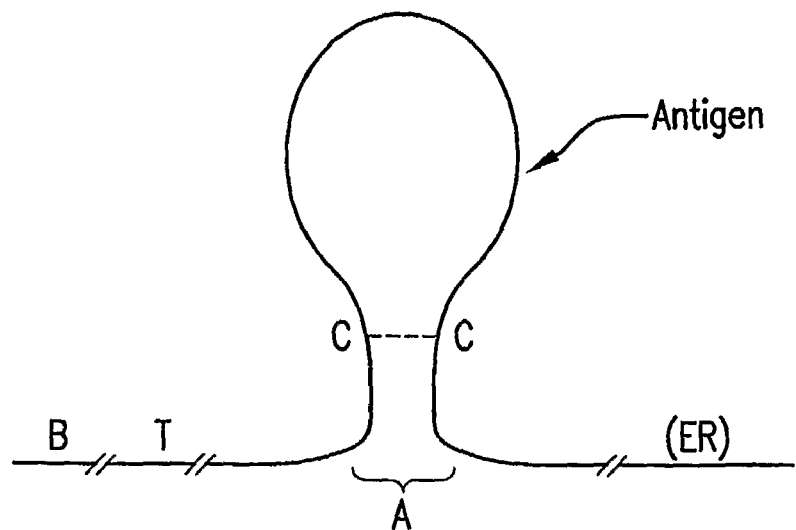

FIG. 12 presents a schematic exemplifying a region of a chimeric immunogen in which a heterologous antigen is presented in a constrained configuration due to the presence of a disulfide bridge between cysteines flanking the heterologous antigen. Hatched lines indicate that the complete structure of the chimeric immunogen N- and C-terminus is not shown. B, receptor binding domain; T, translocation domain; A, heterologous antigen domain; ER, optional ER retention domain.

Figure 13:
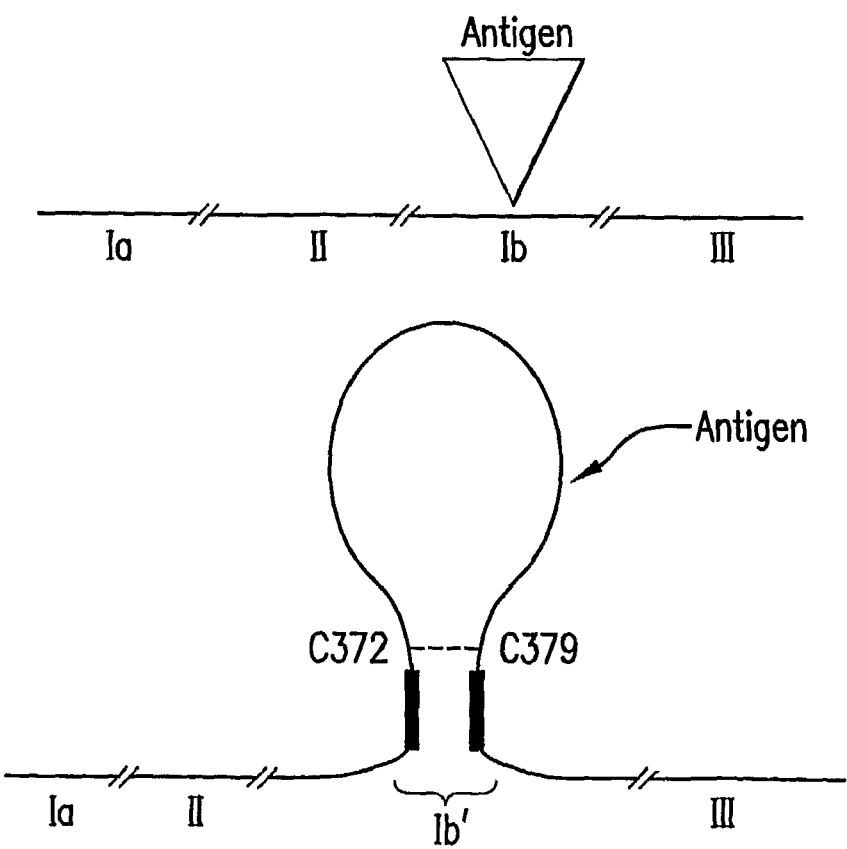

FIG. 13 presents a schematic exemplifying a chimeric immunogen of the invention based on a PE backbone. The relative size of the regions is not intended to necessarily be to scale, but rather is simply for illustrative purposes. Ib' represents a PE Ib domain modified to include a heterologous antigen.

6. DETAILED DESCRIPTION OF THE INVENTION

6.1. Definitions

Unless defined otherwise, all technical and scientific terms used herein have the meaning commonly understood by a person skilled in the art to which this invention belongs. As used herein, the following terms have the meanings ascribed to them unless specified otherwise.

A "ligand" is a compound that specifically binds to a target molecule. Exemplary ligands include, but are not limited to, an antibody, a cytokine, a substrate, a signaling molecule, and the like.

A "receptor" is compound that specifically binds to a ligand.

A ligand or a receptor (e.g., an antibody) "specifically binds to" or "is specifically immunoreactive with" another molecule when the ligand or receptor functions in a binding reaction that indicates the presence of the molecule in a sample of heterogeneous compounds. Thus, under designated assay (e.g., immunoassay) conditions, the ligand or receptor binds preferentially to a particular compound and does not bind in a significant amount to other compounds present in the sample. In one embodiment, the ligand or receptor does not bind in a detectable amount to other compounds present in a sample. For example, a polynucleotide specifically binds under hybridization conditions to another polynucleotide comprising a complementary sequence and an antibody specifically binds under immunoassay conditions to an antigen bearing an epitope used to induce the antibody.

As used herein, a "heterologous antigen" refers to a peptide or polypeptide is heterologous to at least one of the other portions of the chimeric immunogen. "Heterologous" as used herein refers to a first polypeptide that is associated with a second polypeptide with which it is not found in nature (e.g., the first and second polypeptides are derived from the same or different polypeptides which, when combined, provide a chimeric polypeptide not found in nature).

"Immunoassay" refers to a method of detecting an analyte in a sample involving contacting the sample with an antibody that specifically binds to the analyte and detecting binding between the antibody and the analyte. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity. In one example, an antibody that binds a particular antigen with an affinity ($K_m$) of about 10 µM specifically binds the antigen.

"Vaccine" refers to an agent or composition containing an agent effective to confer an at least partially prophylactic or therapeutic degree of immunity on an organism. Methods of making vaccines are, of course, useful in the study of the immune system and in preventing and treating animal or human disease.

An "immune response" refers to one or more biological activities mediated by cells of the immune system in a subject. Such biological activities include, but are not limited to, production of antibodies; activation and proliferation of immune cells, such as, e.g., B cells, T cells, macrophages, leukocytes, lymphocytes, etc.; release of messenger molecules, such as cytokines, chemokines, interleukins, tumor necrosis factors, growth factors, etc.; and the like. An immune response is typically mounted when a cell of the immune system encounters non-self antigen that is recognized by a receptor present on the surface of the immune cell. The immune response preferably protects the subject to some degree against infection by a pathogen that bears the antigen against which the immune response is mounted.

An immune response may be "elicited," "induced," or "induced against" a particular antigen. Each of these terms is intended to be synonymous as used herein and refers to the ability of the chimeric immunogen to generate an immune response upon administration to a subject.

An "immunogen" is a molecule or combination of molecules that can induce an immune response in a subject when the immunogen is administered to the subject.

"Immunizing" refers to administering an immunogen to a subject.

An "immunogenic amount" of a compound is an amount of the compound effective to elicit an immune response in a subject.

"Linker" refers to a molecule that joins two other molecules, either covalently or non-covalently, e.g., through ionic, van der Waals or hydrogen bonds, e.g., a nucleic acid molecule that hybridizes to one complementary sequence at the 5' end and to another complementary sequence at the 3' end, thus joining two non-complementary sequences.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences*, 19th Ed. 1995, Mack Publishing Co., Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

Preferred pharmaceutical carriers depend upon the intended mode of administration of the active agent. Typical modes of administration include enteral (e.g., oral, intranasal, rectal, or vaginal) or parenteral (e.g., subcutaneous, intramuscular, intravenous or intraperitoneal injection; or topical, transdermal, or transmucosal administration).

"Small organic molecule" refers to organic molecules of a size comparable to those organic molecules generally used in pharmaceuticals. The term excludes organic biopolymers (e.g., proteins, nucleic acids, etc.). Preferred small organic molecules range in size up to about 5000 Da, up to about 2000 Da, or up to about 1000 Da.

A "subject" of diagnosis, treatment, or administration is a human or non-human animal, including a mammal, such as a rodent (e.g., a mouse or rat), a lagomorph (e.g., a rabbit), or a primate. A subject of diagnosis, treatment, or administration is preferably a primate, and more preferably a human.

"Treatment" refers to prophylactic treatment or therapeutic treatment. A "prophylactic" treatment is a treatment administered to a subject who does not exhibit signs of a disease or exhibits only early signs for the purpose of decreasing the risk of developing pathology. A "therapeutic" treatment is a treatment administered to a subject who exhibits signs of pathology for the purpose of diminishing, slowing the progression, eliminating, or halting those signs. Thus, treatment of a subject with a composition of the invention can, in certain embodiments, treat an established *C. trachomatis* infection or, in other embodiments, prevent a *C. trachomatis* infection.

"*Pseudomonas* exotoxin A" or "PE" is secreted by *Pseudomonas aeruginosa* as a 67 kD protein composed of three prominent globular domains (Ia, II, and III) and one small subdomain (Ib) that connects domains II and III. See A. S. Allured et al., 1986, *Proc. Natl. Acad. Sci.* 83:1320-1324, and FIG. 11, which presents the amino acid sequence of native PE. Without intending to be bound to any particular theory or mechanism of action, domain Ia of PE is believed to mediate cell binding because domain Ia specifically binds to the low density lipoprotein receptor-related protein ("LRP"), also known as the α2-macroglobulin receptor ("α2-MR") and CD-91. See M. Z. Kounnas et al., 1992, *J. Biol. Chem.* 267: 12420-23. Domain Ia spans amino acids 1-252. Domain II of PE is believed to mediate translocation to the interior of a cell following binding of domain Ia to the α2-MR. Domain II spans amino acids 253-364. Domain Ib has no known function and spans amino acids 365-399. Domain III mediates cytotoxicity of PE and includes an endoplasmic reticulum retention sequence. PE cytotoxicity is believed to result from ADP ribosylation of elongation factor 2, which inactivates protein synthesis. Domain III spans amino acids 400-613 of PE. Deleting amino acid E553 ("ΔE553") from domain III eliminates EF2 ADP ribosylation activity and detoxifies PE. PE having the mutation ΔE553 is referred to herein as "PEΔE553." Genetically modified forms of PE are described in, e.g., U.S. Pat. Nos. 5,602,095; 5,512,658 and 5,458,878. *Pseudomonas* exotoxin, as used herein, also includes genetically modified, allelic, and chemically inactivated forms of PE within this definition. See, e.g., Vasil et al., 1986, *Infect. Immunol.* 52:538-48. Further, reference to the various domains of PE is made herein to the reference PE sequence presented as FIG. 11. However, one or more domains from modified PE, e.g., genetically or chemically modified PE, or a portion of such domains, can also be used in the chimeric immunogens of the invention so long as the domains retain functional activity. One of skill in the art can readily identify such domains of such modified PE based on, for example, homology to the PE sequence exemplified in FIG. 11 and test for functional activity using, for example, the assays described below.

The amino acid sequence of PE secreted by *Pseudomonas aeruginosa* is provided as SEQ ID NO: 98.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions. Thus, the polynucleotide whose sequence 5'-TATAC-3' is complementary to a polynucleotide whose sequence is 5'-GTATA-3'.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. Exemplary levels of sequence identity include, but are not limited to, 60, 70, 80, 85, 90, 95, 98% or more sequence identity to a given sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. Exemplary levels of sequence homology include, but are not limited to, 60, 70, 80, 85, 90, 95, 98% or more sequence homology to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, *J. Mol. Biol.* 215:403-10 (with special reference to the published default setting, i.e., parameters w=4, t=17) and Altschul et al., 1997, *Nucleic Acids Res.,* 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Ala (A), Gly (G), Ile (I), Leu (L), Met (M) and Val (V).

"Hydrophilic Amino Acid" refers to an amino acid exhibiting a hydrophobicity of less than zero according to the normalized consensus hydrophobicity scale of Eisenberg et al., 1984, *J. Mol. Biol.* 179:125-142. Genetically encoded hydrophilic amino acids include Arg (R), Asn (N), Asp (D), Glu (E), Gln (Q), His (H), Lys (K), Ser (S) and Thr (T).

"Hydrophobic Amino Acid" refers to an amino acid exhibiting a hydrophobicity of greater than zero according to the normalized consensus hydrophobicity scale of Eisenberg et al., 1984, *J. Mol. Biol.* 179:125-142. Genetically encoded hydrophobic amino acids include Ala (A), Gly (G), Ile (I), Leu (L), Met (M), Phe (F), Pro (P), Trp (W), Tyr (Y) and Val (V).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

"Basic Amino Acid" refers to a hydrophilic amino acid having a side chain pK value of greater than 7. Basic amino acids typically have positively charged side chains at physiological pH due to association with a hydrogen ion. Genetically encoded basic amino acids include Arg (R), His (H) and Lys (K).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and RNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Amplification" refers to any means by which a polynucleotide sequence is copied and thus expanded into a larger number of polynucleotide molecules, e.g., by reverse transcription, polymerase chain reaction, ligase chain reaction, and the like.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids can be found in Tijssen, 1993, *Laboratory Techniques in Biochemistry and Molecular Biology-Hybridization with Nucleic Acid Probes*, part I, chapter 2, "Overview of principles of hybridization and the strategy of nucleic acid probe assays", Elsevier, NY; Sambrook et al., 2001, *Molecular Cloning: A Laboratory Manual*, Cold Spring Harbor Laboratory, 3$^{rd}$ ed., NY; and Ausubel et al., eds., Current Edition, *Current Protocols in Molecular Biology*, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

One example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. Conventional notation is used herein to portray polypeptide sequences; the beginning of a polypeptide sequence is the amino-terminus, while the end of a polypeptide sequence is the carboxyl-terminus.

The term "protein" typically refers to large polypeptides, for example, polypeptides comprising more than about 50 amino acids. The term "protein" can also refer to dimers, trimers, and multimers that comprise more than one polypeptide.

The term "peptide" typically refers to short polypeptides, for example, polypeptides comprising about 50 or less amino acids.

"Conservative substitution" refers to the substitution in a polypeptide of an amino acid with a functionally similar amino acid. The following six groups each contain amino acids that are conservative substitutions for one another:

Alanine (A), Serine (S), and Threonine (T)
Aspartic acid (D) and Glutamic acid (E)
Asparagine (N) and Glutamine (Q)
Arginine (R) and Lysine (K)
Isoleucine (I), Leucine (L), Methionine (M), and Valine (V)
Phenylalanine (F), Tyrosine (Y), and Tryptophan (W).

6.2. Chimeric Immunogens

The chimeric immunogens of the invention generally comprise: (1) a "receptor binding domain" that functions as a ligand for a cell surface receptor and that mediates binding of the protein to a cell; (2) a "translocation domain" that mediates translocation from the exterior of the cell to the interior of the cell; (3) an "heterologous antigen domain", which comprises an antigen of interest (often referred to herein as a "heterologous antigen"); and, optionally, (4) an "endoplasmic reticulum ("ER") retention domain" that facilitates translocation of the chimeric immunogen from the endosome to the endoplasmic reticulum, from which it enters the cytosol. As discussed in more detail below, the chimeric immunogen can still induce an immune response in the absence of the ER retention domain, although the presence or absence of this domain alters the nature of the immune response induced, as described below.

In general, an exemplary chimeric immunogen of the invention can be represented by the formula:

B-(L)-T-A-(ER)

wherein B represents a receptor binding domain; T represents a translocation domain; L represents an optional linker between the receptor binding domain and the translocation domain; A represents a heterologous antigen domain; and ER represents an optional ER retention domain. The various domains of the chimeric immunogen are described in greater detail below.

An immune response that recognizes the heterologous antigen is elicited upon administration of the chimeric immunogen to a subject. In certain embodiments, the elicited immune response is specific for the heterologous antigen. The heterologous antigen and the structure of the chimeric immunogen can be selected so as to facilitate eliciting a humoral response or to facilitate eliciting a cellular response.

For example, in some embodiments, and particularly where it is desirable to enhance a humoral response against the heterologous antigen of the chimeric immunogen, the heterologous antigen is flanked by cysteines. Without intending to be bound to any particular theory or mechanism of action, as illustrated schematically in FIG. 12, in this embodiment, it is believed that crosslinking of the cysteine residues through a disulfide bond (represented by the dashed lines) provides a structure that presents the antigen in a constrained fashion, which can better mimic a native configuration of the antigen in the native protein. Such constructs and their uses are described in more detail below.

In other embodiments, the relative position of an ER retention domain and the heterologous antigen can be modified so as to affect whether the immune response elicited is predominantly Class I MHC-mediated ("cellular") or predominantly Class II MHC-mediated (humoral). As discuss in more detail below, and without being held to theory, placing the heterologous antigen relatively closer to the ER retention signal (e.g., R/KDEL) of the ER retention domain facilitates directing the polypeptide into the Class I MHC processing pathway, and thus facilitates inducing a cellular immune response. Increasing the distance between the ER retention signal and heterologous antigen (or, indeed, simply omitting the ER retention domain) facilitates directing the polypeptide into the Class II MHC processing pathway, and thus facilitates inducing a humoral immune response.

Thus, where a predominantly humoral response against the heterologous antigen is desired, the chimeric immunogen can lack an ER retention domain and provide the heterologous antigen flanked by cysteines to provide the constrained structure described in FIG. 12. Where a predominantly cellular response against the heterologous antigen is desired, the chimeric immunogen includes an ER retention domain with the ER retention signal and heterologous antigen positioned relatively close together (e.g., within less than 20 amino acids) and lacks crosslinked cysteines (e.g., the cysteines do not flank the heterologous antigen or, if present, are reduced to avoid formation of the disulfide linkage).

As is apparent from the discussion herein, the domains of the chimeric immunogens can be provided in different configurations from N- to C-terminus (e.g., from N- to C-terminus, the receptor binding domain, then the translocation domain, then the heterologous antigen domain, then, optionally, the ER retention domain). Although the arrangement exemplified in the formula above is preferred, the domains of the chimeric immunogen can be in any order as long as the domains retain their relevant functional activities. Further, the heterologous antigen domain can include a plurality (e.g., 2 or more, 3 or more, or 4 or more) heterologous antigens, which heterologous antigens can be present within the heterologous antigen domain immediately adjacent one another, or separated from one another (e.g., by a sequence of a polypeptide which provides the backbone of the construct or by a linker). Several representative assays to test such functional activities are set forth below.

In one embodiment of particular interest, the domains and "backbone" of the chimeric immunogen is provided by *Pseudomonas* exotoxin A (PE). In this embodiment, as exemplified schematically in FIG. 13, the chimeric immunogen comprises structural domains corresponding to the receptor binding and translocation domains of PE, i.e., PE domains Ia and II, respectively. The chimeric immunogens can optionally comprise structural domains corresponding to the other domains of PE, domains Ib and III, the latter of which is an ER retention domain of PE.

The Ib domain can provide a scaffold in which a heterologous antigen can be provided. For example, the heterologous antigen can be inserted into any portion of the Ib domain and/or replace some or all residues of the Ib domain. Where desired, and as also illustrated in FIG. 13, the heterologous antigen can be positioned within the Ib domain so that the cysteine residues at positions 372 (C372) and 379 (C379) flank the antigen, providing for a constrained loop configuration for presentation of the antigen (referred to as Ib' in FIG. 13). In addition, the folded structure provides for pairing of the charged residues N-terminal of C372 and C-terminal of C379 (represented by the dark lines). Without being held to theory, the Ib residues adjacent the cysteines thus provide for formation of a "stem" to this structure, which can further enhance surface accessibility of the antigen and enhance a humoral response.

Alternatively or in addition, the heterologous antigen can be introduced into or replace any other portion of the PE-backbone with the proviso that insertion of the antigen does not disrupt a cell-binding or translocation activity. The structural domains of PE perform certain functions, including, but not limited to, cell recognition, translocation and endoplasmic reticulum retention, that correspond to the functions of the domains of PE. By including or omitting the optional domains of PE, the character of the induced immune response can be modulated, as described herein.

Such chimeric immunogens offer several advantages over conventional immunogens. To begin with, certain embodiments of the chimeric immunogens can be constructed and expressed in recombinant systems. These systems eliminate any requirement to crosslink the heterologous antigen to a carrier protein. Recombinant technology also allows one to make a chimeric immunogen having an insertion site designed for introduction of any desired heterologous antigen. Such insertion sites allow the skilled artisan to quickly and easily produce chimeric immunogens that comprise either known variants of a heterologous antigen or emerging variants of evolving heterologous antigens.

Further, the chimeric immunogens can be engineered to alter the function of their domains in order to tailor the activity of the immunogen to its intended use. For example, by selecting the appropriate receptor binding domain, the skilled artisan can target the chimeric immunogen to bind to a desired cell or cell line.

In addition, because certain embodiments of the chimeric immunogens include a constrained cysteine-cysteine loop, heterologous antigens that are so constrained in nature can be presented in native or near-native conformation. By doing so, the induced immune response is more likely to be specific for antigen in its native conformation, and can more effectively protect the subject from infection by the pathogen.

Moreover, the chimeric immunogens can be used to elicit a humoral, a cell-mediated and/or a mucosal immune response. Depending on the pathway by which the chimeric immunogen is processed in an antigen-presenting cell, the chimeric immunogen can induce an immune response mediated by either class I or class II MHC. See Becerra et al., 2003, *Surgery* 133:404-410 and Lippolis et al., 2000, *Cell. Immunol.* 203:75-83. Further, if the PE chimeras are administered to a mucosal surface of the subject, a secretory immune response involving IgA can be induced. See, e.g., Mrsny et al., 1999, *Vaccine* 17:1425-1433 and Mrsny et al., 2002, *Drug Discovery Today* 7:247-258.

The chimeric immunogens of the invention can also be used to elicit a protective immune response without using attenuated or inactivated pathogens. Thus, the chimeric immunogens avoid the risk of incomplete inactivation or attenuation of a pathogen or reversion of the pathogen to a fully infectious state, leading to infection by the pathogen upon administration of the vaccine. For example, administration of attenuated polio vaccine actually results in paralytic polio in about 1 in 4 million subjects receiving the vaccine. See Kuby, 1997, *Immunology* Ch. 18, W.H. Freeman and Company, New York.

Accordingly, in certain aspects, the invention provides a chimeric immunogen that comprises a receptor binding domain, a translocation domain, and a *C. trachomatis* antigen. In certain embodiments, the *C. trachomatis* antigen comprises or is an amino acid sequence according to Formula I:

$$X_{aa1}\text{-}X_{aa2}\text{-}X_{aa3}\text{-}X_{aa4}\text{-}X_{aa5}\text{-}X_{aa6}\text{-}X_{aa7}\text{-}X_{aa8}\text{-}X_{aa9}\text{-}$$
$$X_{aa10}\text{-}X_{aa11}\text{-}X_{aa12}\text{-}X_{aa13}\text{-}X_{aa14}\text{-}X_{aa15}\text{-}X_{aa16}\text{-}$$
$$X_{aa17}\text{-}X_{aa18}\text{-}X_{aa19}\text{-}X_{aa20}\text{-}X_{aa21}\text{-}X_{aa22}\text{-}X_{aa23}\text{-}$$
$$X_{aa24}\text{-}X_{aa25}\text{-}X_{aa26}\text{-}X_{aa27}, \quad \text{Formula I}$$

wherein $X_{aa1}$ is A, V, or absent; $X_{aa2}$ is E, T, K, or absent; $X_{aa3}$ is A, T, P, or absent; $X_{aa4}$ is I, V, or absent; $X_{aa5}$ is F, L, V, or absent; $X_{aa6}$ is D or absent; $X_{aa7}$ is V, T, I, or absent; $X_{aa8}$ is T; $X_{aa9}$ is T; $X_{aa10}$ is L; $X_{a11}$ is N; $X_{aa12}$ is P or R; $X_{aa13}$ is T; $X_{aa14}$ is T or I; $X_{aa15}$ is A or T; $X_{aa16}$ is G; $X_{aa17}$ is A, C, K, or absent; $X_{aa18}$ is G or absent; $X_{aa19}$ is S, G, T, A, E, D, or absent; $X_{aa20}$ is V or absent; $X_{aa21}$ is A, V, I, K, or absent; $X_{aa22}$ is A, G, S, T, or absent; $X_{aa23}$ is A, G, N, S, or absent; $X_{aa24}$ is G, N, or absent; $X_{aa25}$ is A, S, T, or absent; $X_{aa26}$ is D, E, or absent; and $X_{aa27}$ is G, N, or absent (SEQ ID NO.:42).

In certain embodiments, the *C. trachomatis* antigen comprises or is an amino acid sequence according to Formula II:

$$X_{aa1}\text{-}X_{aa2}\text{-}X_{aa3}\text{-}X_{aa4}\text{-}X_{aa5}\text{-}X_{aa6}, \quad \text{Formula II}$$

wherein $X_{aa1}$ is A, S; $X_{aa2}$ is G; $X_{aa3}$ is T; $X_{aa4}$ is D or E, $X_{aa5}$ is A or G; and $X_{aa6}$ is A or V (SEQ ID NO.:2).

In certain embodiments, the *C. trachomatis* antigen comprises or is an amino acid sequence according to Formula III:

$$X_{aa1}\text{-}X_{aa2}\text{-}X_{aa3}\text{-}X_{aa4}\text{-}X_{aa5}\text{-}X_{aa6}\text{-}X_{aa7}\text{-}X_{aa8}\text{-}X_{aa9}\text{-}$$
$$X_{aa10}\text{-}X_{aa11}\text{-}X_{aa12}\text{-}X_{aa13}\text{-}X_{aa14}\text{-}X_{aa15}\text{-}X_{aa16}\text{-}$$
$$X_{aa17}\text{-}X_{aa18}\text{-}X_{aa19}\text{-}X_{aa20}\text{-}X_{aa21}\text{-}X_{aa22}\text{-}X_{aa23}, \quad \text{Formula III}$$

wherein $X_{aa1}$ is G; $X_{aa2}$ is A, D, or E; $X_{aa3}$ is A, E, or K; $X_{aa4}$ is L or P; $X_{aa5}$ is A or T; $X_{aa6}$ is A, G, S, T, or V; $X_{aa7}$ is K, N, R, S, or absent; $X_{aa8}$ is A, D, or absent; $X_{aa9}$ is A, D, I, S, T, or V; $X_{aa10}$ is A, E, G, T, or V; $X_{aa11}$ is D, G, or N; $X_{aa12}$ is L, N, or T; $X_{aa13}$ is A, E, Q, S, or T; $X_{aa14}$ is A, K, N, S, or T; $X_{aa15}$ is A, D, or T; $X_{aa16}$ is L or P; $X_{aa17}$ is K, S, T, or V; $X_{aa18}$ is I, K, T, or V; $X_{aa19}$ is C, L, or N; $X_{aa20}$ is I, T or V; $X_{aa21}$ is A or E; $X_{aa22}$ is R; and $X_{aa23}$ is E, P, or T (SEQ ID NO.:3).

In certain embodiments, the *C. trachomatis* antigen comprises or is an amino acid sequence according to Formula IV:

$$X_{aa1}\text{-}X_{aa2}\text{-}X_{aa3}\text{-}X_{aa4}\text{-}X_{aa5}\text{-}X_{aa6}\text{-}X_{aa7}\text{-}X_{aa8}\text{-}X_{aa9}\text{-}$$
$$X_{aa10}\text{-}X_{aa11}\text{-}X_{aa12}\text{-}X_{aa13}\text{-}X_{aa14}\text{-}X_{aa15}\text{-}X_{aa16}\text{-}$$
$$X_{aa17}\text{-}X_{aa18}\text{-}X_{aa19}\text{-}X_{aa20}\text{-}X_{aa21}\text{-}X_{aa22}\text{-}X_{aa23}\text{-}$$
$$X_{aa24}\text{-}X_{aa25}\text{-}X_{aa26}\text{-}X_{aa27}, \quad \text{Formula IV}$$

wherein $X_{aa1}$ is A or V; $X_{aa2}$ is E, T, or K; $X_{aa3}$ is A, T, or P; $X_{aa4}$ is I or V; $X_{aa5}$ is F, L, or V; $X_{aa6}$ is D; $X_{aa7}$ is V, T, or I; $X_{aa8}$ is T; $X_{aa9}$ is T; $X_{aa10}$ is L; $X_{aa11}$ is N; $X_{aa12}$ is P or R; $X_{aa13}$ is T; $X_{aa14}$ is T or I; $X_{aa15}$ is A or T; $X_{aa16}$ is G; $X_{aa17}$ is A, C, or K; $X_{aa18}$ is G; $X_{aa19}$ is S, G, T, A, E, or D; $X_{aa20}$ is V; $X_{aa21}$ is A, V, I, or K; $X_{aa22}$ is A, G, S, or T; $X_{aa23}$ is A, G, N, or S; $X_{aa24}$ is G, N, or absent; $X_{aa25}$ is A, S, or T; $X_{aa26}$ is D or E; and $X_{aa27}$ is G or N (SEQ ID NO.:1).

In certain embodiments, the chimeric immunogen comprises a receptor binding domain, a translocation domain, and a *C. trachomatis* antigen comprising an amino acid sequence that is selected from the group consisting of AGTEAA (SEQ ID NO.:4), AGTDAA (SEQ ID NO.:5), AETIFDVTTLNP-TIAGAGDVKTSAEG (SEQ ID NO.:6), AETILDVTTLNP-TIAGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKP-KGYVGKE (SEQ ID NO.:11), ILWEGFGGDPCDPCTT (SEQ ID NO.:12), ALNIWDRFDV (SEQ ID NO.:13), KMKSRKSCGIAVGTTVVSADKYAVT (SEQ ID NO.: 14), CAETIFDVTTLNPTIAGAGDVKTSAEGC (SEQ ID NO.: 15), CAETILDVTTLNPTIAGKGTVVTSAEC (SEQ ID NO.:16), CTTLNPTIAGC (SEQ ID NO.: 17), CGAKPTAT-TGNATAPSTLTAREC (SEQ ID NO.:18), and CTTSDVA-GLQNDPC (SEQ ID NO.:19). In certain embodiments, the *C. trachomatis* antigen is selected from the group consisting of AGTEAA (SEQ ID NO.:4) and AGTDAA (SEQ ID NO.: 5). In certain embodiments, the *C. trachomatis* antigen is selected from the group consisting of AETIFDVTTLNPTIA-GAGDVKTSAEG (SEQ ID NO.:6), AETILDVTTLNPTI-AGKGTVVTSAE (SEQ ID NO.:7), TTLNPTIAGC (SEQ ID NO.:8), CAETIFDVTTLNPTIAGAGDVKTSAEGC (SEQ ID NO.:15), CAETILDVTTLNPTIAGKGTVVT-SAEC (SEQ ID NO.:16), and CTTLNPTIAGC (SEQ ID NO.: 17). In certain embodiments, the *C. trachomatis* antigen is selected from the group consisting of GAKPTATTGNA-TAPSTLTARE (SEQ ID NO.:9), TTSDVAGLQNDPC (SEQ ID NO.: 10), CGAKPTATTGNATAPSTLTAREC (SEQ ID NO.:18), and CTTSDVAGLQNDPC (SEQ ID NO.:19). In certain embodiments, the *C. trachomatis* antigen is selected from the group consisting of SEFTINKPKGYVGKE (SEQ ID NO.:11), ILWEGFGGDPCDPCTT (SEQ ID NO.:12), ALNIWDRFDV (SEQ ID NO.:13), and KMKSRKSCGIA-VGTTVVSADKYAVT (SEQ ID NO.:14).

Without intending to be bound to any particular theory or mechanism of action, these peptides are believed to correspond to major B-cell and T-cell antigens from *C. trachomatis* major outer membrane protein (MOMP). In certain embodiments, the chimeric immunogen, when administered to a subject, can induce an immune response in the subject that is effective to reduce adherence of a microorganism that expresses said *C. trachomatis* antigen to epithelial cells of the subject. In other embodiments, the chimeric immunogen, when administered to a subject, generates an immune response in the subject that reduces the cytotoxicity of *Pseudomonas* exotoxin A to the subject.

In certain embodiments, the chimeric immunogen further comprises an endoplasmic reticulum retention domain. In certain embodiments, the *C. trachomatis* antigen is located between said translocation domain and said endoplasmic reticulum retention domain. In certain embodiments, the endoplasmic reticulum retention domain is an enzymatically inactive domain III, or portion thereof, of *Pseudomonas* exotoxin A. In certain embodiments, the enzymatically inactive domain III of *Pseudomonas* exotoxin A is inactivated by deleting a glutamate at position 553.

In certain embodiments, the endoplasmic reticulum retention domain comprises an ER retention signal that has an amino acid sequence selected from the group of RDEL (SEQ ID NO.:20) or KDEL (SEQ ID NO.:21). In certain embodiments, the ER retention signal is sufficiently near the C-terminus of said endoplasmic reticulum retention domain to result in retention of the chimeric immunogen in the endoplasmic reticulum.

In certain embodiments, the chimeric immunogen comprises a translocation domain that is selected from the group consisting of a translocation domain from *Pseudomonas* exotoxin A, diptheria toxin, pertussis toxin, cholera toxin, heat-labile *E. coli* enterotoxin, shiga toxin, and shiga-like toxin. In further embodiments, the translocation domain is domain II of *Pseudomonas* exotoxin A. In yet further embodiments, the translocation domain comprises amino acids 280 to 364 of domain II of *Pseudomonas* exotoxin A.

In certain embodiments, the chimeric immunogen comprises more than one of said *C. trachomatis* antigens. For example, the chimeric immunogen can comprise 1, 2, 3, 4, 5, 6, 7, 8, 9, 10, 15, 20, or more of the *C. trachomatis* antigens. In certain embodiments, the chimeric immunogen comprises more than one of the same *C. trachomatis* antigen. In certain embodiments, the chimeric immunogen comprises more than one different *C. trachomatis* antigen. In certain embodiments, the chimeric immunogen comprises a *C. trachomatis* antigen that comprises a sequence that is AGTEAA (SEQ ID NO.:4) and a *C. trachomatis* antigen that comprises a sequence that is AETIFDVTTLNPTIAGAGDVKTSAEG (SEQ ID NO.:6). In certain embodiments, the chimeric immunogen comprises a *C. trachomatis* antigen that comprises a sequence that is AGTDAA (SEQ ID NO.:5) and a *C. trachomatis* antigen that comprises a sequence that is AETIFDVTTLNPTIAGAGD-VKTSAEG (SEQ ID NO.:6). In certain embodiments, the chimeric immunogen comprises a *C. trachomatis* antigen that comprises a sequence that is AGTEAA (SEQ ID NO.:4), a *C. trachomatis* antigen that comprises a sequence that is AGTDAA (SEQ ID NO.:5), and a *C. trachomatis* antigen that comprises a sequence that is AETIFDVTTLNPTIAGAGD-VKTSAEG (SEQ ID NO.:6). In certain embodiments, the chimeric immunogen comprises a *C. trachomatis* antigen that comprises a sequence that is AGTEAA (SEQ ID NO.:4) and a *C. trachomatis* antigen that comprises a sequence that is GAKPTATTGNATAPSTLTARE (SEQ ID NO.:9). In certain embodiments, the chimeric immunogen comprises a *C. trachomatis* antigen that comprises a sequence that is AGTDAA (SEQ ID NO.:5) and a *C. trachomatis* antigen that comprises a sequence that is GAKPTATTGNATAPSTLTARE (SEQ ID NO.:9).

In certain embodiments, the chimeric immunogen comprises a *C. trachomatis* antigen that comprises a sequence that is selected from the group consisting of AGTEAA (SEQ ID NO.:4), AGTDAA (SEQ ID NO.:5), AETIFDVTTLNPTIA-GAGDVKTSAEG (SEQ ID NO.:6), AETILDVTTLNPTI-AGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKP-KGYVGKE (SEQ ID NO.:11), ILWEGFGGDPCDPCTT (SEQ ID NO.:12), ALNIWDRFDV (SEQ ID NO.:13), KMKSRKSCGIAVGTTVVSADKYAVT (SEQ ID NO.:14), CAETIFDVTTLNPTIAGAGDVKTSAEGC (SEQ ID NO.: 15), CAETILDVTTLNPTIAGKGTVVTSAEC (SEQ ID NO.:16), CTTLNPTIAGC (SEQ ID NO.: 17), CGAKPTAT-TGNATAPSTLTAREC (SEQ ID NO.:18), and CTTSDVA-GLQNDPC (SEQ ID NO.:19) and a *C. trachomatis* antigen that comprises a sequence that is selected from the group consisting of SEFTINKPKGYVGKE (SEQ ID NO.:11), ILWEGFGGDPCDPCTT (SEQ ID NO.:12), ALNIW-DRFDV (SEQ ID NO.:13) and KMKSRKSCGIAVGTTV-VSADKYAVT (SEQ ID NO.:14).

In certain embodiments, the chimeric immunogen comprises a receptor binding domain that is selected from the group consisting of domain Ia of *Pseudomonas* exotoxin A; a receptor binding domain from cholera toxin, diptheria toxin, shiga toxin, or shiga-like toxin; a monoclonal antibody, a polyclonal antibody, or a single-chain antibody that binds a cell surface receptor, or any antigen-binding fragment thereof; an Fc region of an antibody; TGFα, TGFβ, EGF, PDGF, IGF, or FGF; IL-1, IL-2, IL-3, or IL-6; and MIP-1a, MIP-1b, MCAF, or IL-8. In further embodiments, the receptor binding domain is domain Ia of *Pseudomonas* exotoxin A. In yet further embodiments, the domain Ia of *Pseudomonas* exotoxin A has an amino acid sequence that is SEQ ID NO.: 22.

In certain embodiments, the receptor binding domain binds to α2-macroglobulin receptor, epidermal growth factor receptor, transferrin receptor, interleukin-2 receptor, interleukin-6 receptor, interleukin-8 receptor, Fc receptor, poly-IgG receptor, asialoglycopolypeptide receptor, CD3, CD4, CD8, chemokine receptor, CD25, CD11B, CD11C, CD80, CD86, TNFα receptor, TOLL receptor, M-CSF receptor, GM-CSF receptor, scavenger receptor, or VEGF receptor. In further embodiments, the receptor binding domain binds to α2-macroglobulin receptor. Preferably, the receptor bound by the receptor binding domain is a human receptor.

In certain embodiments, the chimeric immunogen has an amino acid sequence that is selected from the group consisting of SEQ ID NOs.:23-33.

6.2.1. Receptor Binding Domain

The chimeric immunogens of the invention generally comprise a receptor binding domain. The receptor binding domain can be any receptor binding domain that binds to a cell surface receptor without limitation. Such receptor binding domains are well-known to those of skill in the art. Preferably, the receptor binding domain binds specifically to the cell surface receptor. Preferably, the receptor bound by the receptor binding domain is internalized by the cell following binding by the receptor binding domain. The receptor binding domain should bind to the cell surface receptor with sufficient affinity to hold the chimeric immunogen in proximity to the cell surface to allow endocytosis of the chimeric immunogen. Representative assays that can routinely be used by the skilled artisan to assess binding of the receptor binding domain to a cell surface receptor are described below.

In certain embodiments, the receptor binding domain can comprise a polypeptide, a peptide, a protein, a lipid, a carbohydrate, or a small organic molecule, or a combination thereof. Examples of each of these molecules that bind to cell surface receptors are well known to those of skill in the art. Suitable peptides, polypeptides, or proteins include, but are not limited to, bacterial toxin receptor binding domains, such as the receptor binding domains from PE, cholera toxin, diptheria toxin, shiga toxin, shiga-like toxin, etc.; antibodies, including monoclonal, polyclonal, and single-chain antibodies that bind a cell surface receptor, or antigen-binding fragments thereof, growth factors, such as TGFα; TGFβ, EGF, PDGF, IGF, FGF, etc.; cytokines, such as IL-1, IL-2, IL-3, IL-6, etc; chemokines, such as MIP-1α, MIP-1b, MCAF, IL-8, etc.; and other ligands, such as CD4, the Fc portion of an antibody, cell adhesion molecules from the immunoglobulin superfamily, integrins, ligands specific for the IgA receptor, etc. See, e.g., Pastan et al., 1992, *Annu. Rev. Biochem.* 61:331-54; and U.S. Pat. Nos. 5,668,255, 5,696,237, 5,863,745, 5,965,406, 6,022,950, 6,051,405, 6,251,392, 6,440,419, and 6,488,926. The skilled artisan can select the appropriate receptor binding domain based upon, for example, the expression pattern of the receptor to which the receptor binding domain binds.

Lipids suitable for receptor binding domains include, but are not limited to, lipids that themselves bind cell surface receptors, such as sphingosine-1-phosphate, lysophosphatidic acid, sphingosylphosphorylcholine, retinoic acid, etc.; lipoproteins such as apolipoprotein E, apolipoprotein A, etc., and glycolipids such as lipopolysaccharide, etc.; glycosphingolipids such as globotriaosylceramide and galabiosylceramide; and the like. Carbohydrates suitable for receptor binding domains include, but are not limited to, monosaccharides, disaccharides, and polysaccharides that comprise simple sugars such as glucose, fructose, galactose, etc.; and glycoproteins such as mucins, selecting, and the like. Suitable small organic molecules for receptor binding domains include, but are not limited to, vitamins, such as vitamin A, B1, B2, B3, B6, B9, B12, C, D, E, and K, amino acids, and other small molecules that are recognized and/or taken up by receptors present on the surface of cells, e.g., epithelial cells.

In certain embodiments, the receptor binding domain can bind to a receptor found on an epithelial cell. In further embodiments, the receptor binding domain can bind to a receptor found on the apical membrane of a polarized epithelial cell. In still further embodiments, the receptor binding domain can bind to a receptor found on the apical membrane of a mucosal epithelial cell. The receptor binding domain can bind to any receptor present on the apical membrane of an epithelial cell that is internalized following binding by a receptor binding domain known by one of skill in the art without limitation. For example, the receptor binding domain can bind to α2-MR. An example of a receptor binding domain that can bind to α2-MR is domain Ia of PE. Accordingly, in certain embodiments, the receptor binding domain is domain Ia of PE. In other embodiments, the receptor binding domain is a portion of domain Ia of PE that can bind to α2-MR.

In certain embodiments, the receptor binding domain can bind to a receptor present on a professional antigen presenting cell, such as, for example, a dendritic cell or a macrophage. The receptor binding domain can bind to any receptor present on a professional antigen presenting cell without limitation. For example, the receptor binding domain can bind to any receptor identified as present on a dendritic or other professional antigen presenting cell identified in Figdor, 2003, *Pathol. Biol. (Paris).* 51(2):61-3; Coombes et al., 2001, *Immunol Lett.* 3; 78(2):103-11; Shortman K et al., 1997, *Ciba Found Symp.* 204:130-8; discussion 138-41; Katz, 1998, *Curr Opin Immunol.* 1(2):213-9; and Goldsby et al., 2003, *Immunology*, 5th Edition W.H. Freeman & Company, New York, N.Y. In particular, the receptor binding domain can bind to α2-MR, which is also expressed on the surface of professional antigen presenting cells. Thus, in certain embodiments, the receptor binding domain can bind to a receptor that is present on both an epithelial cell and on a professional antigen presenting cell.

In certain embodiments, the receptor binding domains can bind to a cell surface receptor that is selected from the group consisting of α2-macroglobulin receptor (CD91), epidermal growth factor receptor, transferrin receptor, interleukin-2 receptor, interleukin-6 receptor, interleukin-8 receptor, Fc receptor, poly-IgG receptor, asialoglycopolypeptide receptor, CD3, CD4, CD8, chemokine receptor, CD25, CD11B, CD11C, CD80, CD86, TNFα receptor, TOLL receptor, M-CSF receptor, GM-CSF receptor, scavenger receptor, and VEGF receptor. Indeed, any cell surface receptor, without limitation, known by one of skill in the art to be internalized by a cell following binding of the receptor by a receptor binding domain can be bound by the receptor binding domain.

In certain embodiments, the chimeric immunogens of the invention comprise more than one domain that can function as a receptor binding domain. For example, the chimeric immunogen can comprise PE domain Ia in addition to another receptor binding domain.

The receptor binding domain can be attached to the remainder of the chimeric immunogen by any method or means known by one of skill in the art to be useful for attaching such molecules, without limitation. In certain embodiments, the receptor binding domain is expressed together with the remainder of the chimeric immunogen as a fusion protein. Such embodiments are particularly useful when the receptor binding domain and the remainder of the immunogen are formed from peptides or polypeptides.

In other embodiments, the receptor binding domain is connected with the remainder of the chimeric immunogen with a linker. In yet other embodiments, the receptor binding domain is connected with the remainder of the chimeric immunogen without a linker. Either of these embodiments are useful when the receptor binding domain comprises a peptide, polypeptide, protein, lipid, carbohydrate, nucleic acid, or small organic molecule.

In certain embodiments, the linker can form a covalent bond between the receptor binding domain and the remainder of the chimeric immunogen. In other embodiments, the linker can link the receptor binding domain to the remainder of the chimeric immunogen with one or more non-covalent interactions of sufficient affinity. One of skill in the art can readily recognize linkers that interact with each other with sufficient affinity to be useful in the chimeric immunogens of the invention. For example, biotin can be attached to the receptor binding domain, and streptavidin can be attached to the remainder of the molecule. In certain embodiments, the linker can directly link the receptor binding domain to the remainder of the molecule, e.g., via a peptide bond. In other embodiments, the linker itself comprises two or more molecules that associate in order to link the receptor binding domain to the remainder of the molecule. Exemplary linkers include, but are not limited to, straight or branched-chain carbon linkers, heterocyclic carbon linkers, substituted carbon linkers, unsaturated carbon linkers, aromatic carbon linkers, peptide linkers, etc.

In embodiments where a linker is used to connect the receptor binding domain to the remainder of the chimeric immunogen, the linkers can be attached to the receptor binding domain and/or the remainder of the chimeric immunogen by any means or method known by one of skill in the art without limitation. For example, the linker can be attached to the receptor binding domain and/or the remainder of the chimeric immunogen with an ether, ester, thioether, thioester, amide, imide, disulfide or other suitable moiety. The skilled artisan can select the appropriate linker and means for attaching the linker based on the physical and chemical properties of the chosen receptor binding domain and the linker. The linker can be attached to any suitable functional group on the receptor binding domain or the remainder of the molecule. For example, the linker can be attached to sulfhydryl (—S), carboxylic acid (COOH) or free amine (—NH2) groups, which are available for reaction with a suitable functional group on a linker. These groups can also be used to connect the receptor binding domain directly connected with the remainder of the molecule in the absence of a linker.

Further, the receptor binding domain and/or the remainder of the chimeric immunogen can be derivatized, for example, to facilitate attachment of a linker to these moieties. For example, such derivatization can be accomplished by attaching suitable derivatives such as those available from Pierce Chemical Company, Rockford, Ill. Alternatively, derivatization may involve chemical treatment of the receptor binding domain and/or the remainder of the molecule. For example, glycol cleavage of the sugar moiety of a carbohydrate or glycoprotein receptor binding domain with periodate generates free aldehyde groups. These free aldehyde groups may be reacted with free amine or hydrazine groups on the remainder of the molecule in order to connect these portions of the molecule. See U.S. Pat. No. 4,671,958. Further, the skilled artisan can generate free sulfhydryl groups on proteins to provide a reactive moiety for making a disulfide, thioether, theioester, etc. linkage. See U.S. Pat. No. 4,659,839.

Any of these methods for attaching a linker to a receptor binding domain and/or the remainder of a chimeric immunogen can also be used to connect a receptor binding domain with the remainder of the chimeric immunogen in the absence of a linker. In such embodiments, the receptor binding domain is coupled with the remainder of the immunogen using a method suitable for the particular receptor binding domain. Thus, any method suitable for connecting a protein, peptide, polypeptide, nucleic acid, carbohydrate, lipid, or small organic molecule to the remainder of the chimeric immunogen known to one of skill in the art, without limitation, can be used to connect the receptor binding domain to the remainder of the immunogen. In addition to the methods for attaching a linker to a receptor binding domain or the remainder of an immunogen, as described above, the receptor binding domain can be connected with the remainder of the immunogen as described in U.S. Pat. Nos. 6,673,905; 6,585,973; 6,596,475; 5,856,090; 5,663,312; 5,391,723; 6,171,614; 5,366,958; and 5,614,503.

In certain embodiments, the receptor binding domain can be a monoclonal antibody or antigen-binding portion of an antibody. In some of these embodiments, the chimeric immunogen is expressed as a fusion protein that comprises an immunoglobulin heavy chain from an immunoglobulin specific for a receptor on a cell to which the chimeric immunogen is intended to bind, or antigen-binding portion thereof. The light chain of the immunoglobulin, or antigen-binding portion thereof, then can be co-expressed with the chimeric immunogen, thereby forming an antigen-binding light chain-heavy chain dimer. In other embodiments, the antibody, or antigen-binding portion thereof, can be expressed and assembled separately from the remainder of the chimeric immunogen and chemically linked thereto.

6.2.2. Translocation Domain

The chimeric immunogens of the invention also comprise a translocation domain. The translocation domain can be any translocation domain known by one of skill in the art to effect translocation of chimeric proteins that have bound to a cell surface receptor from outside the cell to inside the cell, e.g., the outside of an epithelial cell, such as, for example, a polarized epithelial cell. In certain embodiments, the translocation domain is a translocation domain from PE, diptheria toxin, pertussis toxin, cholera toxin, heat-labile *E. coli* enterotoxin, shiga toxin, or shiga-like toxin. See, for example, U.S. Pat. Nos. 5,965,406, and 6,022,950. In preferred embodiments, the translocation domain is domain II of PE. In certain embodiments, the translocation domain of domain II of PE has an amino acid sequence that is SEQ ID NO.:34.

The translocation domain need not, though it may, comprise the entire amino acid sequence of domain II of native PE, which spans residues 253-364 of PE. For example, the translocation domain can comprise a portion of PE that spans residues 280-344 of domain II of PE. Preferably, the translocation domain comprises the amino acids corresponding to positions 339 and 343 of PE. Further, conservative or non-conservative substitutions can be made to the amino acid sequence of the translocation domain, as long as translocation activity is not substantially eliminated. A representative assay that can routinely be used by one of skill in the art to determine whether a translocation domain has translocation activity is described below.

Without intending to be limited to any particular theory or mechanism of action, the translocation domain is believed to perform at least two functions in the chimeric immunogens of the invention. First, the translocation domain permits the trafficking of the chimeric immunogen through a polarized, mucosal epithelial cell into the bloodstream after the immunogen binds to a receptor present on the apical surface of the polarized epithelial cell. This trafficking results in the release of the chimeric immunogen from the basal-lateral membrane of the polarized epithelial cell. Second, the translocation domain facilitates endocytosis of the chimeric immunogen into an antigen presenting cell after the immunogen binds to a receptor present on the surface of the antigen presenting cell.

6.2.3. Heterologous Antigen

The chimeric immunogens of the invention also comprise a heterologous antigen. The antigen is "heterologous" because it is heterologous to a portion of the remainder of the immunogen; i.e., not naturally found in a molecule from which one of the other domains of the chimeric immunogen is derived. The heterologous antigen can be any molecule, macromolecule, combination of molecules, etc. against which an immune response is desired. Thus, the heterologous antigen can be any peptide, polypeptide, protein, nucleic acid, lipid, carbohydrate, or small organic molecule, or any combination thereof, against which the skilled artisan wishes to induce an immune response. Preferably, the heterologous antigen is an antigen that is present on a pathogen. More preferably, the heterologous antigen is an antigen that, when administered to a subject as part of a chimeric immunogen, results in an immune response against the heterologous antigen that protects the subject from infection by a pathogen from which the heterologous antigen is derived.

The heterologous antigen can be attached to the remainder of the chimeric immunogen by any method known by one of skill in the art without limitation. In certain, embodiments, the heterologous antigen is expressed together with the remainder of the chimeric immunogen as a fusion protein. In such embodiments, the heterologous antigen can be inserted into or replace any portion of the chimeric immunogen, so long as the receptor binding domain, the translocation domain, and the optional ER retention signal domain, when present, retain their activities, and the immune response induced against the heterologous antigen retains specificity. In certain embodiments, it can be useful for the ER retention domain to have the ADP-ribosylation activity of Domain III of PE, as this activity allows convenient assessment of receptor binding and translocation activity as monitored by cell death caused by ADP-ribosylation mediated by Domain III of PE. Methods for assessing the specificity of the immune response against the heterologous antigen are extensively described below. In chimeric immunogen embodiments based on PE, the heterologous antigen is preferably placed in the chimeric immunogen to the C-terminal side of the furin cleavage site found at about amino acid 279. Where the chimeric immunogen is based on PE, the heterologous antigen is preferably inserted into or replaces all or a portion of the Ib loop of PE, into the ER retention domain, or attached to or near the C-terminal end of the translocation domain.

In native PE, the Ib loop (domain Ib) spans amino acids 365 to 399, and is structurally characterized by a disulfide bond between two cysteines at positions 372 and 379. See FIGS. 11, 12, and 13. This portion of PE is not essential for any known activity of PE, including cell binding, translocation, ER retention or ADP ribosylation activity. Accordingly, domain Ib can be deleted entirely, or modified to contain one or more heterologous antigen(s).

Thus, in certain embodiments, the heterologous antigen can be inserted into domain Ib, or a domain corresponding to domain Ib in the case of PE derivatives. If desirable, the heterologous antigen can be inserted into domain Ib wherein the cysteines at positions 372 and 379 are not crosslinked. This can be accomplished by reducing the disulfide linkage between the cysteines, by deleting one or both of the cysteines entirely from the Ib domain, by mutating one or both of the cysteines to other residues, such as, for example, serine, or by other similar techniques. Alternatively, the heterologous antigen can be inserted into or replace all or a portion of the Ib loop between the cysteines at positions 372 and 379, or corresponding to such residues in the case of PE derivatives. In such embodiments, the disulfide linkage between the cysteines can be used to constrain the heterologous antigen domain.

In certain embodiments, one or more epitopes of the heterologous antigen can be provided within a loop created by a disulfide bridge between the two cysteines, e.g., one or more epitopes of the heterologous antigen can be flanked by the cysteines of the Ib loop. The cysteines can be present in the chimeric immunogen backbone or can be present in the heterologous antigen. In certain embodiments, the heterologous antigen can be separated from one or both of the cysteines by one, two, three, four, five, six, seven ten, or more amino acids. In certain embodiments, the amino acids that separate the heterologous antigen from the cysteine(s) are endogenous to the MOMP protein from which the heterologous antigen is selected. In certain embodiments, such amino acids are the amino acids adjacent to the heterologous antigen in the MOMP protein from which the heterologous antigen is selected. In certain embodiments, the amino acids that separate the heterologous antigen from the cysteines are heterologous to the MOMP protein. In certain embodiments, the amino acids that separate the heterologous antigen from the cysteines are heterologous to *Pseudomonas* exotoxin A. In certain embodiments, the amino acids that separate the heterologous antigen from the cysteines are heterologous to the MOMP protein and to *Pseudomonas* exotoxin A. In certain embodiments, the heterologous antigen can comprise or be flanked by one, two, or more cysteines that can replace one or both of the cysteines present at positions 372 and 379. Thus, in certain embodiments, the cysteine at position 372 can be replaced by a cysteine at or near the N-terminus of the heterologous antigen. In certain embodiments, the cysteine at position 379 can be replaced by a cysteine at or near the C-terminus of the heterologous antigen. In certain embodiments, the cysteine at position 372 can be replaced by a cysteine at or near the N-terminus of the heterologous antigen and the cysteine at position 379 can be replaced by a cysteine at or near the C-terminus of the heterologous antigen.

These arrangements offer several advantages. The chimeric immunogens can be used in this manner to present heterologous antigens that naturally comprise a cysteine-cysteine disulfide bond in native or near-native conformation. These embodiments are particularly useful when a humoral response against the heterologous antigen is to be induced. Further, without intending to be bound to any particular theory or mechanism of action, it is believed that charged amino acid residues in the native Ib domain result in a hydrophilic structure that protrudes from the molecule and into the solvent. Thus, inserting the heterologous antigen into or in place of the Ib loop gives immune system components unfettered access to the antigen, resulting in more effective antigen presentation. Such access is particularly useful when the heterologous antigen is a B cell antigen for inducing a humoral immune responses. Further, changes, including mutations or insertions, to domain Ib do not appear to affect activity of the other PE domains. Accordingly, although native Ib domain has only six amino acids between the cysteine residues, much longer sequences can be inserted into the loop without disrupting the other functions of the chimeric immunogen.

In other embodiments, the heterologous antigen can be inserted into the optional ER retention domain of the chimeric immunogen. Without intending to be bound to any particular theory or mechanism of action, it is believed that the nature of the immune response against the heterologous antigen varies depending on the degree of separation between the antigen and the ER retention signal. In particular, the degree to which the heterologous antigen is processed by the Class I or II MHC pathways can vary depending on this degree of separation. By placing the heterologous antigen close to the ER retention signal, e.g., inserting the heterologous antigen into the ER retention domain of the chimeric immunogen within 100, preferably within 50, amino acids of the ER retention signal, more of the heterologous antigen can be directed into the Class I MHC processing pathway, thereby inducing a cellular immune response. Conversely, when the heterologous antigen is further from the ER retention signal, more of the antigen is directed into the Class II MHC processing pathway, thereby facilitating induction of a humoral immune response. If the immune response is intended to be primarily humoral, with essentially no Class I MHC cell mediated response, the ER retention domain can be deleted entirely, and the heterologous antigen can be attached to the immunogen in another location, such as, for example, to the C-terminus of the translocation domain or in the Ib loop. Thus, by controlling the spatial relationship between the heterologous antigen and the ER retention signal, the skilled artisan can modulate the immune response that is induced against the heterologous antigen.

In embodiments where the heterologous antigen is expressed together with another portion of the chimeric immunogen as a fusion protein, the heterologous antigen can be can be inserted into the chimeric immunogen by any method known to one of skill in the art without limitation. For example, amino acids corresponding to the heterologous antigen can be inserted directly into the chimeric immunogen, with or without deletion of native amino acid sequences. In certain embodiments, all or part of the Ib domain of PE can be deleted and replaced with the heterologous antigen. In certain embodiments, the cysteine residues of the Ib loop are deleted so that the heterologous antigen remains unconstrained, which may be preferable when inducing a predominantly cell-mediated immune response. In other embodiments, the cysteine residues of the Ib loop are linked with a disulfide bond and constrain the heterologous antigen, which may be preferable when inducing a predominantly humoral immune response.

In embodiments where the heterologous antigen is not expressed together with the remainder of the chimeric immunogen as a fusion protein, the heterologous antigen can be connected with the remainder of the chimeric immunogen by any suitable method known by one of skill in the art, without limitation. More specifically, the exemplary methods described above for connecting a receptor binding domain to the remainder of the molecule are equally applicable for connecting the heterologous antigen to the remainder of the molecule.

In certain embodiments, the heterologous antigen is a *C. trachomatis* peptide, polypeptide, or protein. The heterologous antigen can be any peptide, polypeptide, or protein against which an immune response is desired to be induced. In certain embodiments, the heterologous antigen is a peptide that comprises about 5, about 8, about 10, about 12, about 15, about 17, about 20, about 25, about 30, about 40, about 50, or about 60, about 70, about 80, about 90, about 100, about 200, about 400, about 600, about 800, or about 1000 amino acids. In certain embodiments, the heterologous antigen is a polypeptide derived from *C. trachomatis*. In certain embodiments, the heterologous antigen is *C. trachomatis* MOMP, or a portion thereof. In further embodiments, the heterologous antigen is a peptide that comprises a sequence selected from a *C. trachomatis* MOMP. In still further embodiments, the heterologous antigen is a peptide of the sequence identified as any of SEQ ID NO.:4-19.

In certain embodiments, the *C. trachomatis* MOMP is a MOMP from *C. trachomatis* B class, C class, or intermediate class. In certain embodiments, the *C. trachomatis* MOMP is a MOMP from *C. trachomatis* serovar A (Accession No.: S12799; Hayes et al., 1990, *J. Gen. Microbiol.* 136(Pt 8):1559), serovar B (Accession No.: B60756; Hayes et al., 1990, *J. Gen. Microbiol.* 136(Pt 8):1559), serovar C (Accession No.: P08780; Stephens et al., 1987, *J. Bacteriol.* 169: 3879), serovar D (Accession No.: H71484; Stephens et al., 1998, *Science* 282:754), serovar E (Accession No.: MMCWTE; Peterson et al., 1990, *Nucleic Acids Res.* 18:3414), serovar F (Accession No.: MMCWTF; Zhang et al., 1990, *Nucleic Acids Res.* 18:1061), serovar G (variable regions identified by Accession No.:H30587; Yuan et al., 1989, *Infect. Immun.* 57:1040; complete nucleotide sequence identified as Accession No. AY950627), serovar H (Accession No.: MMCWTH; Hamilton and Malinowski, 1989, *Nucleic Acids Res.* 17:8366), serovar I (variable regions identified by Accession No.: C30593; Yuan et al., 1989, *Infect. Immun.* 57:1040; complete nucleotide sequence identified as Accession No. AF414961), serovar J (variable regions identified by Accession No.: D30593; Yuan et al., 1989, *Infect. Immun.* 57:1040; complete nucleotide sequence identified as Accession No. AY950635), serovar K (variable regions identified by Accession No.: E30593; Yuan et al., 1989, *Infect. Immun.* 57:1040; complete nucleotide sequence identified as Accession No. AF414965), serovar Ba (variable regions identified by Accession No.: B30587; Yuan et al., 1989, *Infect. Immun.* 57:1040; complete nucleotide sequence identified as Accession No. AY950630), serovar Da (Accession No.: JC1432; Sayada et al., 1992, *Gene* 120:129), serovar Ia (Accession No. AF063201; Stothard et al., 1998, *Infect. Immun.* 66:3618), serovar Ja (Accession No. AF063203; Stothard et al., 1998, *Infect. Immun.* 66:3618), serovar L1 (Accession No.: P19542 or Accession No.: S06259; Pickett et al., 1987, *FEMS Microbiol. Lett.* 42:185), serovar L2 (Accession No.: P06597; Stephens et al., 1987, *J. Bacteriol.* 168:1277), serovar L3 (Accession No.: JE0413; Kaul et al., 1989, *Infect. Immun.* 57:487), or serovar La (Accession No. AF304858). In certain embodiments, the heterologous antigen comprises a MOMP sequence that is conserved in more than one *C. trachomatis* serovar. In certain embodiments, the MOMP sequence is conserved across at least two members of *C. trachomatis* B class. In certain embodiments, the MOMP sequence is conserved across at least two members of *C. trachomatis* C class. In certain embodiments, the MOMP sequence is conserved across at least two members of *C. trachomatis* intermediate class. In certain embodiments, the MOMP sequence is at least 50%, 55%, 60%, 65%, 70%, 75%, 80%, 85%, 90%, 95%, 99% or 100% identical to at least one of the members of *C. trachomatis* class. In certain embodiments, the MOMP sequence is at least 50%, 55%, 60%, 65%, 70%, 75%, 80%, 85%, 90%, 95%, 99% or 100% homologous to at least one of the members of *C. trachomatis* class. In certain embodiments, the MOMP sequence is at least 50%, 55%, 60%, 65%, 70%, 75%, 80%, 85%, 90%, 95%, 99% or 100% identical to two or more of the members of *C. trachomatis* class. In certain embodiments, the MOMP sequence is at least 50%, 55%, 60%, 65%, 70%, 75%, 80%, 85%, 90%, 95%, 99% or 100% homologous to two or more of the members of *C. trachomatis* class.

In certain embodiments, the heterologous antigen comprises or is between about 2 and about 10 amino acids selected from a *C. trachomatis* MOMP. In certain embodiments, the heterologous antigen comprises or is between about 2 and about 20 amino acids selected from a *C. trachomatis* MOMP. In certain embodiments, the heterologous antigen comprises or is between about 2 and about 30 amino acids selected from a *C. trachomatis* MOMP. In certain embodiments, the heterologous antigen comprises or is between about 2 and about 50 amino acids selected from a *C. trachomatis* MOMP. In certain embodiments, the heterologous antigen comprises or is between about 2 and about 75 amino acids selected from a *C. trachomatis* MOMP. In certain embodiments, the heterologous antigen comprises or is between about 2 and about 100 amino acids selected from a *C. trachomatis* MOMP. In certain embodiments, the heterologous antigen comprises or is between about 2 and about 150 amino acids selected from a *C. trachomatis* MOMP. In certain embodiments, the heterologous antigen comprises or is between about 2 and about 200 amino acids selected from a *C. trachomatis* MOMP. In certain embodiments, the heterologous antigen comprises or is between about 2 and about 250 amino acids selected from a *C. trachomatis* MOMP. In certain embodiments, the heterologous antigen comprises or is between about 2 and about 300 amino acids selected from a *C. trachomatis* MOMP. In certain embodiments, the heterologous antigen comprises or is between about 2 and about 350 amino acids selected from a *C. trachomatis* MOMP. In certain embodiments, the heterologous antigen comprises or is between about 2 and about 150 amino acids selected from a *C. trachomatis* MOMP. In certain embodiments, the heterologous antigen comprises or is between about 5 and about 10 amino acids selected from a *C. trachomatis* MOMP. In certain embodiments, the heterologous antigen comprises or is between about 5 and about 15 amino acids selected from a *C. trachomatis* MOMP. In certain embodiments, the heterologous antigen comprises or is between about 5 and about 20 amino acids selected from a *C. trachomatis* MOMP. In certain embodiments, the heterologous antigen comprises or is between about 5 and about 30 amino acids selected from a *C. trachomatis* MOMP. In certain embodiments, the heterologous antigen comprises or is between about 8 and about 10 amino acids selected from a *C. trachomatis* MOMP. In certain embodiments, the heterologous antigen comprises or is between about 8 and about 15 amino acids selected from a *C. trachomatis* MOMP. In certain embodiments, the heterologous antigen comprises or is between about 8 and about 20 amino acids selected from a *C. trachomatis* MOMP. In certain embodiments, the heterologous antigen comprises or is between about 8 and about 30 amino acids selected from a *C. trachomatis* MOMP. In certain embodiments, the heterologous antigen comprises or is between about 10 and about 15 amino acids selected from a *C. trachomatis* MOMP. In certain embodiments, the heterologous antigen comprises or is between about 10 and about 20 amino acids selected from a *C. trachomatis* MOMP. In certain embodiments, the heterologous antigen comprises or is between about 10 and about 25 amino acids selected from a *C. trachomatis* MOMP. In certain embodiments, the heterologous antigen comprises or is between about 10 and about 30 amino acids selected from a *C. trachomatis* MOMP. In certain embodiments, the heterologous antigen comprises or is between about 10 and about 50 amino acids selected from a *C. trachomatis* MOMP.

The following discussion describes particular portions of *C. trachomatis* MOMP that refer to particular residues of the *C. trachomatis* MOMP. In certain embodiments, these particular residues can be interpreted with reference to the variable regions VS1, VS2, VS3, and VS4 of *C. trachomatis* MOMP as defined by Yuan et al., 1989, *Infect. Immun.* 57:1040. In this definition, amino acids 64-83 define VS1, amino acids 139-160 define VS2, amino acids 224-237 define VS3, and amino acids 288-317 define VS4. Thus, one skilled in the art can identify which MOMP sequences are defined by the following amino acid positions by comparing the described positions to the alignments of Yuan et al. Further, any of the sequences from the serovars described by Yuan et al. corresponding to the below-described amino acids can be used as a heterologous antigen. Still further, one of skill in the art can, by aligning a MOMP sequence from a serovar identified above to the sequences described by Yuan et al., identify sequences from any *C. trachomatis* serovar known to one of skill in the art that correspond to the below-described amino acids which can be used as a heterologous antigen. In other embodiments, the below-described amino acid sequences correspond to the MOMP sequence from *C. trachomatis* serovar A, or to MOMP amino acid sequences from other serovars of *C. trachomatis* that correspond to the *C. trachomatis* serovar A MOMP sequence when aligned.

Thus, in certain embodiments, the heterologous antigen comprises or is a MOMP sequence corresponding to amino acids 64-83. In certain embodiments, the heterologous antigen comprises or is a MOMP sequence corresponding to amino acids 139-160. In certain embodiments, the heterologous antigen comprises or is a MOMP sequence corresponding to amino acids 224-237. In certain embodiments, the heterologous antigen comprises or is a MOMP sequence corresponding to amino acids 288-317. In certain embodiments, the heterologous antigen comprises or is a MOMP sequence corresponding to amino acids 231-236. In certain embodiments, the heterologous antigen comprises or is a MOMP sequence corresponding to amino acids 289-314. In certain embodiments, the heterologous antigen comprises or is a MOMP sequence corresponding to amino acids 293-309. In certain embodiments, the heterologous antigen comprises or is a MOMP sequence corresponding to amino acids 63-83. In certain embodiments, the heterologous antigen comprises or is a MOMP sequence corresponding to amino acids 69-77. In certain embodiments, the heterologous antigen comprises or is a MOMP sequence corresponding to amino acids 214-227. In certain embodiments, the heterologous antigen comprises or is a MOMP sequence corresponding to amino acids 17-33. In certain embodiments, the heterologous antigen comprises or is a MOMP sequence corresponding to amino acids 106-116. In certain embodiments, the heterologous antigen comprises or is a MOMP sequence corresponding to amino acids 331-355. In certain embodiments, the heterologous antigen comprises or is a MOMP amino acid sequence identified as an epitope of a MOMP in U.S. Pat. No. 5,869,608. In certain embodiments, the heterologous antigen comprises or is a MOMP amino acid sequence identified as a variable region of a MOMP in U.S. Pat. No. 5,869,608.

In certain embodiments, the heterologous antigen comprises or is an amino acid sequence that is selected from the group consisting of AGTEAA (SEQ ID NO.:4), AGTDAA (SEQ ID NO.:5), AETIFDVTTLNPTIAGAGDVKTSAEG (SEQ ID NO.:6), AETILDVTTLNPTIAGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKPKGYVGKE (SEQ ID NO.:11), ILWEGFGGDPCDPCTT (SEQ ID NO.:12), ALNIWDRFDV (SEQ ID NO.:13), KMKSRKSCGIAVGTTVVSADKYAVT (SEQ ID NO.:14), CAETIFDVTTLNPTIAGAGDVKTSAEGC (SEQ ID NO.:15), CAETILDVTTLNPTIAGKGTVVTSAEC (SEQ ID NO.:16), CTTLNPTIAGC (SEQ ID NO.:17), CGAKPTATTGNATAPSTLTAREC (SEQ ID NO.:18), and CTTSDVAGLQNDPC (SEQ ID NO.:19). In one preferred embodiment, the heterologous antigen is a peptide that has an amino acid sequence that is AETIFDVTTLNPTIAGAGDVKTSAEG (SEQ ID NO.:6).

In certain embodiments, the heterologous antigen comprises an amino acid sequence that is AGTEAA (SEQ ID NO.:4). In certain embodiments, the heterologous antigen comprises an amino acid sequence that is AGTDAA (SEQ ID NO.:5). In certain embodiments, the heterologous antigen comprises an amino acid sequence that is AETIFDVTTLNPTIAGAGDVKTSAEG (SEQ ID NO.:6). In certain embodiments, the heterologous antigen comprises an amino acid sequence that is AETILDVTTLNPTIAGKGTVVTSAE (SEQ ID NO.:7). In certain embodiments, the heterologous antigen comprises an amino acid sequence that is TTLNPTIAGC (SEQ ID NO.:8). In certain embodiments, the heterologous antigen comprises an amino acid sequence that is GAKPTATTGNATAPSTLTARE (SEQ ID NO.:9). In certain embodiments, the heterologous antigen comprises an amino acid sequence that is TTSDVAGLQNDPC (SEQ ID NO.:10). In certain embodiments, the heterologous antigen comprises an amino acid sequence that is SEFTINKPKGYVGKE (SEQ ID NO.:11). In certain embodiments, the heterologous antigen comprises an amino acid sequence that is ILWEGFGGDPCDPCTT (SEQ ID NO.:12). In certain embodiments, the heterologous antigen comprises an amino acid sequence that is ALNIWDRFDV (SEQ ID NO.:13). In certain embodiments, the heterologous antigen comprises an amino acid sequence that is KMKSRKSCGIAVGTTVVSADKYAVT (SEQ ID NO.:14). In certain embodiments, the heterologous antigen comprises an amino acid sequence that is CAETIFDVTTLNPTIAGAGDVKTSAEGC (SEQ ID NO.:15). In certain embodiments, the heterologous antigen comprises an amino acid sequence that is CAETILDVTTLNPTIAGKGTVVTSAEC (SEQ ID NO.:16). In certain embodiments, the heterologous antigen comprises an amino acid sequence that is CTTLNPTIAGC (SEQ ID NO.: 17). In certain embodiments, the heterologous antigen comprises an amino acid sequence that is CGAKPTATTGNATAPSTL- TAREC (SEQ ID NO.:18). In certain embodiments, the heterologous antigen comprises an amino acid sequence that is CTTSDVAGLQNDPC (SEQ ID NO.:19).

In certain embodiments, the heterologous antigen comprises 1, 2, 3, 4, 5, 6, 7, 8, 9, 10, 11, 12, 13, 14, 15, 16, 17, 18, 19, 20, 25, 30, 35, 40, 45, 50 or more amino acids to one or both sides of the C. trachomatis sequences described above. In certain embodiments, such amino acids are heterologous to the C. trachomatis antigen, e.g., the amino acids are not present in the C. trachomatis MOMP from which the antigen is derived. In certain embodiments, the amino acids are endogenous to the C. trachomatis antigen, e.g., the amino acids are present in the C. trachomatis MOMP from which the antigen is derived. In certain embodiments, the endogenous amino acids flank the heterologous antigen in the C. trachomatis MOMP.

In certain embodiments, the heterologous antigen is not a C. trachomatis antigen whose amino acid sequence consists of AKPTATTGNATAPSTLTARE (SEQ ID NO.:43). In certain embodiments, the heterologous antigen is not a C. trachomatis antigen whose amino acid sequence consists of NNENQTKVSNSTFVPNMSLDQS (SEQ ID NO.:44). In certain embodiments, the heterologous antigen is not a C. trachomatis antigen whose amino acid sequence consists of KELPLDLTSGTDAA (SEQ ID NO.:45). In certain embodiments, the heterologous antigen is not a C. trachomatis antigen whose amino acid sequence consists of SAETIFDVTTLNPTIAGAGDVKTSAEGQLG (SEQ ID NO.:46). In certain embodiments, the heterologous antigen is not a C. trachomatis antigen whose amino acid sequence consists of AKPTTDTGNSAAPSTLTARE (SEQ ID NO.:47). In certain embodiments, the heterologous antigen is not a C. trachomatis antigen whose amino acid sequence consists of DNENQKTVKAESVPNMSFDQS (SEQ ID NO.:48). In certain embodiments, the heterologous antigen is not a C. trachomatis antigen whose amino acid sequence consists of KEFPLDLTAGTDAA (SEQ ID NO.:49).

In certain embodiments, the heterologous antigen is not a C. trachomatis antigen whose amino acid sequence consists of SATAIFDTTTLNPTIAGAGDVKTGAEGQLG (SEQ ID NO.:50). In certain embodiments, the heterologous antigen is not a C. trachomatis antigen whose amino acid sequence consists of DKPTSTTGNATAPTTLTARE (SEQ ID NO.:51). In certain embodiments, the heterologous antigen is not a C. trachomatis antigen whose amino acid sequence consists of DNENQSTVKTNSVPNMSLDQS (SEQ ID NO.:52). In certain embodiments, the heterologous antigen is not a C. trachomatis antigen whose amino acid sequence consists of QEFPLALIAGTDAA (SEQ ID NO.:53). In certain embodiments, the heterologous antigen is not a C. trachomatis antigen whose amino acid sequence consists of SATAIFDTTTLNPTIAGAGDVKASAEGQLG (SEQ ID NO.:54). In certain embodiments, the heterologous antigen is not a C. trachomatis antigen whose amino acid sequence consists of EALAGASGNTTSTLSKLVERT (SEQ ID NO.:55). In certain embodiments, the heterologous antigen is not a C. trachomatis antigen whose amino acid sequence consists of DGVNATKPAADSIPNVQLNQS (SEQ ID NO.:56). In certain embodiments, the heterologous antigen is not a C. trachomatis antigen whose amino acid sequence consists of KEFPLDLTAGTDAA (SEQ ID NO.:57). In certain embodiments, the heterologous antigen is not a C. trachomatis antigen whose amino acid sequence consists of LVTPVVDITTLNPTIAGCGSVAGANTEGQIS (SEQ ID NO.:58). In certain embodiments, the heterologous antigen is not a C. trachomatis antigen whose amino acid sequence consists of EALAGASGNTTSTLSKLVERT (SEQ ID NO.:59).

In certain embodiments, the heterologous antigen is not a C. trachomatis antigen whose amino acid sequence consists of DGENATQPAATSIPNVQLNQS (SEQ ID NO.:60). In certain embodiments, the heterologous antigen is not a C. trachomatis antigen whose amino acid sequence consists of QEFPLALTAGTDAA (SEQ ID NO.:61). In certain embodiments, the heterologous antigen is not a C. trachomatis antigen whose amino acid sequence consists of LAKPVVDITTLNPTIAGCGSVVMNSEGQIS (SEQ ID NO.:62). In certain embodiments, the heterologous antigen is not a C. trachomatis antigen whose amino acid sequence consists of AAPTTNDAADLQNDPKTNVARP (SEQ ID NO.:63). In certain embodiments, the heterologous antigen is not a C. trachomatis antigen whose amino acid sequence consists of TKTKSSDFNTAKLVPNIALNRA (SEQ ID NO.:64). In certain embodiments, the heterologous antigen is not a C. trachomatis antigen whose amino acid sequence consists of AEFPLDITAGTEAA (SEQ ID NO.:65). In certain embodiments, the heterologous antigen is not a C. trachomatis antigen whose amino acid sequence consists of LAEAILDVTTLNPTIAGKGTVVASGSDNDLA (SEQ ID NO.:66). In certain embodiments, the heterologous antigen is not a C. trachomatis antigen whose amino acid sequence consists of AAPTTKDVAGLENDPTTNVARP (SEQ ID NO.:67). In certain embodiments, the heterologous antigen is not a C. trachomatis antigen whose amino acid sequence consists of TKTQSSNFNTAKLVPNAALNQA (SEQ ID NO.:68). In certain embodiments, the heterologous antigen is not a C. trachomatis antigen whose amino acid sequence consists of AEFPLDIIAGTEAA (SEQ ID NO.:69).

In certain embodiments, the heterologous antigen is not a C. trachomatis antigen whose amino acid sequence consists of LAEAILDVTTLNPTIAGKGTVVSSAENELA (SEQ ID NO.:70). In certain embodiments, the heterologous antigen is not a C. trachomatis antigen whose amino acid sequence consists of AAPTTSDVAGLQNDPTTNVARP (SEQ ID NO.:71). In certain embodiments, the heterologous antigen is not a C. trachomatis antigen whose amino acid sequence consists of TKTQASSFNTANLFPNTALNQA (SEQ ID NO.:72). In certain embodiments, the heterologous antigen is not a C. trachomatis antigen whose amino acid sequence consists of AEFPLDITAGTEAA (SEQ ID NO.:73). In certain embodiments, the heterologous antigen is not a C. trachomatis antigen whose amino acid sequence consists of LAEAILDVTTLNPTIAGKGTVVASGSENDLA (SEQ ID NO.:74). In certain embodiments, the heterologous antigen is not a C. trachomatis antigen whose amino acid sequence consists of AAPTTSDVEGLQNDPTTNVARP (SEQ ID NO.:75). In certain embodiments, the heterologous antigen is not a C. trachomatis antigen whose amino acid sequence consists of TKTQYSKFNTANLVPNTALDRA (SEQ ID NO.:76). In certain embodiments, the heterologous antigen is not a C. trachomatis antigen whose amino acid sequence consists of VEFPLDITAGTEAA (SEQ ID NO.:77). In certain embodiments, the heterologous antigen is not a C. trachomatis antigen whose amino acid sequence consists of LAEAILDVTTLNPTITGKGAVVSSGSDNELA (SEQ ID NO.:78). In certain embodiments, the heterologous antigen is not a C. trachomatis antigen whose amino acid sequence consists of AEPTTSDTAGLSNDPTTNVARP (SEQ ID NO.:79).

In certain embodiments, the heterologous antigen is not a C. trachomatis antigen whose amino acid sequence consists of TKTQSTNFNTAKLVPNTALNQA (SEQ ID NO.:80). In certain embodiments, the heterologous antigen is not a C. trachomatis antigen whose amino acid sequence consists of AEFPLDITAGTEAA (SEQ ID NO.:81). In certain embodiments, the heterologous antigen is not a *C. trachomatis* antigen whose amino acid sequence consists of LAEAVLDVTTLNPTIAGKGSVVASGSENELA (SEQ ID NO.:82). In certain embodiments, the heterologous antigen is not a *C. trachomatis* antigen whose amino acid sequence consists of SAETIFDVTTLNPTIAGAGDVKTSAEGQLG (SEQ ID NO.:83). In certain embodiments, the heterologous antigen is not a *C. trachomatis* antigen whose amino acid sequence consists of SATAIFDTTTLNPTIAGAGDVKTGAEGQLG (SEQ ID NO.:84). In certain embodiments, the heterologous antigen is not a *C. trachomatis* antigen whose amino acid sequence consists of SATAIFDTTTLNPTIAGAGDVKASAEGQLG (SEQ ID NO.:85). In certain embodiments, the heterologous antigen is not a *C. trachomatis* antigen whose amino acid sequence consists of LATAIFDTTTLNPTIAGAGEVKANAEGQLG (SEQ ID NO.:86). In certain embodiments, the heterologous antigen is not a *C. trachomatis* antigen whose amino acid sequence consists of SATTVFDVTTLNPTIAGAGDVKASAEGQLG (SEQ ID NO.: 87). In certain embodiments, the heterologous antigen is not a *C. trachomatis* antigen whose amino acid sequence consists of LVTPVVDITTLNPTIAGCGSVAGANTEGQIS (SEQ ID NO.:88). In certain embodiments, the heterologous antigen is not a *C. trachomatis* antigen whose amino acid sequence consists of LAKPVVDITTLNPTIAGCGSVVAANSEGQIS (SEQ ID NO.:89).

In certain embodiments, the heterologous antigen is not a *C. trachomatis* antigen whose amino acid sequence consists of LAEAILDVTTLNPTIAGKGSVVSAGTDNELA (SEQ ID NO.:90). In certain embodiments, the heterologous antigen is not a *C. trachomatis* antigen whose amino acid sequence consists of LAKPVLDTTTLNPTIAGKGTVVSSAENELA (SEQ ID NO.:91). In certain embodiments, the heterologous antigen is not a *C. trachomatis* antigen whose amino acid sequence consists of LAEAILDVTTLNPTIAGKGTVVASGSDNDLA (SEQ ID NO.:92). In certain embodiments, the heterologous antigen is not a *C. trachomatis* antigen whose amino acid sequence consists of LAEAILDVTTLNPTIAGKGTVVSSAENELA (SEQ ID NO.:93). In certain embodiments, the heterologous antigen is not a *C. trachomatis* antigen whose amino acid sequence consists of LAEAILDVTTLNPTIAGKGTVVASGSENDLA (SEQ ID NO.:94). In certain embodiments, the heterologous antigen is not a *C. trachomatis* antigen whose amino acid sequence consists of LAEAILDVTTLNPTITGKGAVVSSGSDNELA (SEQ ID NO.:95). In certain embodiments, the heterologous antigen is not a *C. trachomatis* antigen whose amino acid sequence consists of LAEAVLDVTTLNPTIAGKGSVVASGSENELA (SEQ ID NO.:96). In certain embodiments, the heterologous antigen is not a *C. trachomatis* antigen whose amino acid sequence consists of VLQTDVNKEFQ (SEQ ID NO.:97).

In certain embodiments, the heterologous antigen is a carbohydrate. The heterologous antigen can be any carbohydrate against which an immune response is desired to be induced. In certain embodiments, the heterologous antigen is a carbohydrate that comprises about 1, about 2, about 3, about 4, about 5, about 8, about 10, about 12, about 15, about 17, about 20, about 25, about 30, about 40, about 50, or about 60, about 70, about 80, about 90, or about 100 sugar monomers. In certain embodiments, the heterologous antigen is a carbohydrate derived from *C. trachomatis*.

In other embodiments, the heterologous antigen can be a glycoprotein, or a portion thereof. The heterologous antigen can be any glycoprotein, or portion of a glycoprotein, against which an immune response is desired to be induced. In certain embodiments, the heterologous antigen is a glycoprotein or glycoprotein portion that comprises about 5, about 8, about 10, about 12, about 15, about 17, about 20, about 25, about 30, about 40, about 50, or about 60, about 70, about 80, about 90, about 100, about 200, about 400, about 600, about 800, or about 1000 amino acids. In certain embodiments, the heterologous antigen is a glycoprotein or glycoprotein portion derived from *C. trachomatis*.

In addition to the protein component, the glycoprotein or glycoprotein portion also comprises a carbohydrate moiety. The carbohydrate moiety of the glycoprotein or glycoprotein portion comprises about 1, about 2, about 3, about 4, about 5, about 8, about 10, about 12, about 15, about 17, about 20, about 25, about 30, about 40, about 50, or about 60, about 70, about 80, about 90, or about 100 sugar monomers.

In general, the skilled artisan may select the heterologous antigen at her discretion, guided by the following discussion. One important factor in selecting the heterologous antigen is the type of immune response that is to be induced. For example, when a humoral immune response is desired, the heterologous antigen should be selected to be recognizable by a B-cell receptor and to be antigenically similar to a region of the source molecule that is available for antibody binding. In certain embodiments, the heterologous antigen is a B-cell antigen. In certain embodiments, the heterologous antigen is a T-cell antigen. In certain embodiments, the heterologous antigen is both a B-cell antigen and a T-cell antigen, e.g., a B-cell antigen can be a T-cell antigen, and a T-cell antigen can be a B-cell antigen.

Important factors to consider when selecting a B-cell antigen include, but are not limited to, the size and conformation of the antigenic determinant to be recognized, both in the context of the chimeric immunogen and in the native molecule from which the heterologous antigen is derived; the hydrophobicity or hydrophilicity of the heterologous antigen; the topographical accessibility of the antigen in the native molecule from which the heterologous antigen is derived; and the flexibility or mobility of the portion of the native molecule from which the heterologous antigen is derived. See, e.g., Kuby, 1997, *Immunology* Chapter 4, W.H. Freeman and Company, New York. Based on these criteria, the skilled artisan can, when appropriate, select a portion of a large molecule, such as a protein, to be the heterologous antigen. If the source of the heterologous antigen cannot be effectively represented by selecting a portion of it, then the skilled artisan can select the entire molecule to be the heterologous antigen. Such embodiments are particularly useful in the cases of B-cell antigens that are formed by non-sequential amino acids, i.e., antigens formed by amino acids that are not adjacent in the primary structure of the source protein.

Similarly, if the skilled artisan wishes to deliver a heterologous antigen to activate T cells, several factors must be considered in the selection of the heterologous antigen. Principle among such factors is whether helper T cells or cytotoxic T cells are to be stimulated. As described below, helper T cells recognize antigen presented by Class II MHC molecules, while cytotoxic T cells recognize antigen present by Class I MHC. Accordingly, in order to selectively activate these populations, the skilled artisan should select the heterologous antigen to be presentable by the appropriate type of MHC. For example, the skilled artisan can select the heterologous antigen to be a peptide that is presented by Class I MHC when a response mediated by cytotoxic T cells is desired. Similarly, the skilled artisan can select the heterologous antigen to be a peptide that is presented by Class II MHC when a response mediated by helper T cells is desired.

Further, both Class I and Class II MHC exhibit significant allelic variation in studied populations. Much is known about Class I and II MHC alleles and the effects of allelic variation on antigens that can be presented by the different alleles. For example, rules for interactions between Class I MHC haplotype and antigens that can be effectively presented by these molecules are reviewed in Stevanovic, 2002, *Transpl Immunol* 10:133-136. Further guidance on selection of appropriate peptide antigens for Class I and II MHC molecules may be found in U.S. Pat. Nos. 5,824,315 and 5,747,269, and in Germain et al., 1993, *Annu. Rev. Immunol.* 11:403-450; Sinigaglia et al, 1994, *Curr. Opin. Immunol.* 6:52-56; Margalit et al., 2003, *Novartis Found Symp.* 254:77-101, 216-22, and 250-252; Takahashi, 2003, *Comp Immunol Microbiol Infect Dis.* 26:309-328; Yang, 2003, *Microbes Infect.* 5:39-47; and Browning et al., 1996, *HLA and MHC: Genes, Molecules and Function* (Davenport and Hill, eds.) A BIOS Scientific Publishers, Oxford. An empirical system for identifying peptide antigens for presentation on Class II MHC, and that can be adapted for identifying peptide antigens for presentation on Class I MHC, is presented in U.S. Pat. No. 6,500,641.

Further, the chimeric immunogen can comprise one or more antigens in addition to the antigen or antigens from *C. trachomatis* MOMP that can be a molecule that potentiates an immune response. Any antigen that can act as immune stimulant known by one of skill in the art without limitation can be used as an antigen in such embodiments. For example, the heterologous antigen can be a nucleic acid with an umethylated CpG motif, with a methylated CpG motif, or without any CpG motifs, as described in U.S. Pat. Nos. 6,653,292 and 6,239,116 and Published U.S. Application 20040152649, lipopolysaccharide (LPS) or an LPS derivative such as mono- or diphosphoryl lipid A, or any of the LPS derivatives or other adjuvants described in U.S. Pat. Nos. 6,716,623, 6,720,146, and 6,759,241.

6.2.4. Endoplasmic Reticulum Retention Domain

The chimeric immunogens of the invention can optionally comprise an endoplasmic reticulum retention domain. This domain comprises an endoplasmic reticulum signal sequence, which functions in translocating the chimeric immunogen from the endosome to the endoplasmic reticulum, and from thence into the cytosol. Native PE comprises an ER retention domain in domain III, which comprises an ER retention signal sequence at its carboxy terminus. In native PE, this ER retention signal is REDLK (SEQ ID NO.:35). The terminal lysine can be eliminated (i.e., REDL (SEQ ID NO.: 20)) without an appreciable decrease in activity. However, any ER retention signal sequence known to one of skill in the art without limitation can be used in the chimeric immunogens of the invention. Other suitable ER retention signal sequences include, but are not limited to, KDEL (SEQ ID NO.:21), or dimers or multimers of these sequences. See, e.g., Ogata et al., 1990, *J. Biol. Chem.* 265:20678-85; U.S. Pat. No. 5,458,878; and Pastan et al., 1992, *Annu. Rev. Biochem.* 61:331-54.

In certain embodiments, the chimeric immunogen comprises domain III of native PE, or a portion thereof. Preferably, the chimeric immunogen comprises domain III of ΔE553 PE. In certain embodiments, domain III, including the ER retention signal, can be entirely eliminated from the chimeric immunogen. In other embodiments, the chimeric immunogen comprises an ER retention signal sequence and comprises a portion or none of the remainder of PE domain III. In certain embodiments, the portion of PE domain III other than the ER retention signal can be replaced by another amino acid sequence. This amino acid sequence can itself be non immunogenic, slightly immunogenic, or highly immunogenic. A highly immunogenic ER retention domain is preferable for use in eliciting a humoral immune response. For example, PE domain III is itself highly immunogenic and can be used in chimeric immunogens where a robust humoral immune response is desired. Chimeric immunogens in which the ER retention domain is only slightly immunogenic will be more useful when an Class I MHC-dependent cell-mediated immune response is desired.

ER retention domain activity can routinely be assessed by those of skill in the art by testing for translocation of the protein into the target cell cytosol using the assays described below.

In native PE, the ER retention sequence is located at the C-terminus of domain III. Native PE domain III has at least two observable activities. Domain III mediates ADP-ribosylation and therefore toxicity. Further, the ER retention signal present at the C-terminus directs endocytosed toxin into the endoplasmic reticulum and from thence, into the cytosol. Eliminating the ER retention sequence from the chimeric immunogens does not alter the activity of *Pseudomonas* exotoxin as a superantigen, but does prevent it from eliciting an MHC Class I-dependent cell-mediated immune response.

The PE domain that mediates ADP-ribosylation is located between about amino acids 400 and 600 of PE. This toxic activity of native PE is preferably eliminated in the chimeric immunogens of the invention. By doing so, the chimeric immunogen can be used as a vehicle for delivering heterologous antigens to be processed by the cell and presented on the cell surface with MHC Class I or Class II molecules, as desired, rather than as a toxin. ADP ribosylation activity can be eliminated by, for example, deleting amino acid E553. See, e.g., Lukac et al., 1988, *Infect. and Immun.* 56:3095-3098. Alternatively, the amino acid sequence of domain III, or portions of it, can be deleted from the protein. Of course, an ER retention sequence should be included at the C-terminus if a Class I MHC-mediated immune response is to be induced.

In certain embodiments, the ER retention domain is substantially identical to the native amino acid sequences of PE domain III, or a fragment thereof. In certain embodiments, the ER retention domain is domain III of PE. In other embodiments, the ER retention domain is domain III of ΔE553 PE. In still other embodiments, the ER retention domain comprises an amino acid sequence that is selected from the group consisting of RDELK, RDEL, and KDEL.

6.3. *C. trachomatis* MOMP Antigens

In another aspect, the invention provides *C. trachomatis* MOMP antigens, or derivatives thereof. Any heterologous antigen described above as suitable for use in a chimeric immunogen of the invention can be a *C. trachomatis* MOMP antigen as set forth below. The *C. trachomatis* antigens are useful, for example, as components of immunogenic compositions as described below. Further, in certain embodiments, a nucleic acid encoding a heterologous antigen as described above can be used as a *C. trachomatis* antigen, as described below.

Accordingly, in certain embodiments, the *C. trachomatis* antigen comprises or is an amino acid sequence that is selected from the group consisting of AETIFDVTTLNPTIAGAGDVKTSAEG (SEQ ID NO.:6), AETILDVTTLNPTIAGKGTVVTSAEC (SEQ ID NO.:7), TTLNPTIAGC (SEQ ID NO.:8), GAKPTATTGNATAPSTLTARE (SEQ ID NO.: 9), TTSDVAGLQNDPC (SEQ ID NO.:10), SEFTINKPKGYVGKE (SEQ ID NO.:11), ILWEGFGGDPCDPCTT (SEQ ID NO.:12), ALNIWDRFDV (SEQ ID NO.:13), KMKSRKSCGIAVGTTVVSADKYAVT (SEQ ID NO.: 14), CAETIFDVTTLNPTIAGAGDVKTSAEGC (SEQ ID NO.: 15), CAETILDVTTLNPTIAGKGTVVTSAEC (SEQ ID NO.:16), CTTLNPTIAGC (SEQ ID NO.:7), CGAKPTATTGNATAPSTLTAREC (SEQ ID NO.:18), and CTTSDVAGLQNDPC (SEQ ID NO.:19). In one embodiment, the *C. trachomatis* antigen is a peptide that has an amino acid sequence that is CAETIFDVTTLNPTIAGAGDVKTSAEGC (SEQ ID NO.:15).

In certain embodiments, the *C. trachomatis* antigen comprises or is an amino acid sequence that is AETIFDVTTLNPTIAGAGDVKTSAEG (SEQ ID NO.:6). In certain embodiments, the *C. trachomatis* antigen comprises an amino acid sequence that is AETILDVTTLNPTIAGKGTVVTSAEC (SEQ ID NO.:7). In certain embodiments, the *C. trachomatis* antigen comprises or is an amino acid sequence that is TTLNPTIAGC (SEQ ID NO.:8). In certain embodiments, the *C. trachomatis* antigen comprises an amino acid sequence that is GAKPTATTGNATAPSTLTARE (SEQ ID NO.:9). In certain embodiments, the *C. trachomatis* antigen comprises or is an amino acid sequence that is TTSDVAGLQNDPC (SEQ ID NO.:10). In certain embodiments, the *C. trachomatis* antigen comprises or is an amino acid sequence that is SEFTINKPKGYVGKE (SEQ ID NO.:11). In certain embodiments, the *C. trachomatis* antigen comprises or is an amino acid sequence that is ILWEGFGGDPCDPCTT (SEQ ID NO.:12). In certain embodiments, the *C. trachomatis* antigen comprises or is an amino acid sequence that is ALNIWDRFDV (SEQ ID NO.:13). In certain embodiments, the *C. trachomatis* antigen comprises or is an amino acid sequence that is KMKSRKSCGIAVGTTVVSADKYAVT (SEQ ID NO.:14). In certain embodiments, the *C. trachomatis* antigen comprises or is an amino acid sequence that is CAETIFDVTTLNPTIAGAGDVKTSAEGC (SEQ ID NO.:15). In certain embodiments, the *C. trachomatis* antigen comprises or is an amino acid sequence that is CAETILDVTTLNPTIAGKGTVVTSAEC (SEQ ID NO.:16). In certain embodiments, the *C. trachomatis* antigen comprises or is an amino acid sequence that is CTTLNPTIAGC (SEQ ID NO.: 17). In certain embodiments, the *C. trachomatis* antigen comprises or is an amino acid sequence that is CGAKPTATTGNATAPSTLTAREC (SEQ ID NO.:18). In certain embodiments, the *C. trachomatis* antigen comprises or is an amino acid sequence that is CTTSDVAGLQNDPC (SEQ ID NO.:19).

In certain embodiments, the *C. trachomatis* antigen comprises or is an amino acid sequence that is AETIFDVTTLNPTIAGAGDVKTSAEG (SEQ ID NO.:6), wherein an immune response induced against the *C. trachomatis* antigen does not recognize an epitope defined by the amino acid sequence QLG (SEQ ID NO.:36). In certain embodiments, an immune response induced against the *C. trachomatis* antigen does not recognize an epitope defined by the amino acid sequence SAEGQLG (SEQ ID NO.:37).

In certain embodiments, the *C. trachomatis* antigen comprises or is an amino acid sequence that is AETILDVTTLNPTIAGKGTVVTSAEC (SEQ ID NO.:7), wherein an immune response induced against the *C. trachomatis* antigen does not recognize an epitope defined by the amino acid sequence GTDELA (SEQ ID NO.:38). In certain embodiments, an immune response induced against the *C. trachomatis* antigen does not recognize an epitope defined by the amino acid sequence AECGTDELA (SEQ ID NO.:39).

In certain embodiments, the *C. trachomatis* antigen comprises or is an amino acid sequence that is TTSDVAGLQNDPC (SEQ ID NO.:10), wherein an immune response induced against the *C. trachomatis* antigen does not recognize an epitope defined by the amino acid sequence TTNVARP (SEQ ID NO.:40).

The *C. trachomatis* MOMP antigens can be prepared using any suitable method. In certain embodiments, the *C. trachomatis* MOMP antigens can be prepared by chemical synthesis. In other embodiments, the *C. trachomatis* MOMP antigens can be prepared biologically using suitable vectors in appropriate cell cultures as described below.

In certain embodiments, the *C. trachomatis* MOMP antigens can be used in immunogenic compositions without further modification. In certain embodiments, the *C. trachomatis* MOMP antigens can be modified, e.g., chemical conjugates, fusion proteins, pegylation, and the like. For example, chemical or nucleotidic or peptidic modifications can be made to allow the nucleotides/peptides to pass through certain biological barriers, to solubilize better, or to facilitate their incorporation into particular galenical forms, such as, e.g., liposomes or microparticles. Further, the *C. trachomatis* MOMP antigens can be deglycosylated or glycosylated, as appropriate.

In certain embodiments, at least one portion of the *C. trachomatis* MOMP antigens of the invention can be conjugated to a support onto which it is absorbed or bound in a covalent or non-covalent manner. The support can be, e.g., natural or synthetic carrier molecules. Such embodiments are useful, for example, in methods of purifying antibodies reactive with the antigens and to increase the immunogenicity of the antigens. Preferably, the carrier molecules are physiologically acceptable and non toxic. The carrier molecules, in the context of an immunogenic composition, also preferably can increase the immunogenicity of the *C. trachomatis* MOMP antigens. The *C. trachomatis* MOMP antigens can be connected with the carrier molecules by, e.g., complementary reactive groups respectively present on the carrier molecule and the peptide known to those skilled in the art. Useful chemical compounds for coupling include, without limitation, dinitrophenol groups and arsonilic acid. Examples of carrier molecules include, but are not limited to, natural proteins such as, e.g., tetanus anatoxin, ovalbumin, serum albumin, hemocyamines, keyhole limpet hemocyanin (KLH), PPD (purified protein derivative) of tuberculin, red blood cells, tetanus toxoid, cholera toxoid, agarose beads, activated carbon, bentonite, etc.; synthetic macromolecular supports such as, e.g., polylysine or poly(D-L-alanine)-poly(L-lysine); hydrocarbon or lipid supports such as, e.g., saturated or unsaturated fatty acids. For a review of some general considerations in use of such compounds, see Harlow and Lane, eds., 1988, *Antibodies, A Laboratory Manual*, Cold Spring Harbor Laboratory Press, Cold Spring Harbor, N.Y. Further, liposomes, particles and microparticles, vesicles, latex bead microspheres, polyphosphoglycans (PGLA) or polystyrene can also be used as a support in the immunogenic compositions of the invention.

In yet another embodiment, the *C. trachomatis* MOMP antigens may be in the form of a multiple antigenic peptide ("MAP", also referred to as an octameric lysine core peptide) construct. Such a construct may be designed employing the MAP system described by Tam, 1988, *Proc. Natl. Acad. Sci. USA* 85:5409. In this system, multiple copies of a *C. trachomatis* antigen are synthesized onto a core matrix of lysine residues as described in Posnett et al., 1988, *J. Biol. Chem.* 263:1719; and Tam, 1992, "Chemically Defined Synthetic Immunogens and Vaccines by the Multiple Antigen Peptide Approach", *Vaccine Research and Developments, Vol.* 1, Koff and Six, eds., Marcel Deblau, Inc., New York, N.Y., pp. 51-87. Each MAP contains multiple copies of one antigen.

Still other modified fragments of *C. trachomatis* MOMP antigens may be prepared by any number of now conventional techniques to improve production thereof, to enhance protein stability or other characteristics, e.g., binding activity or bioavailability, or to confer some other desired property upon the protein. Other useful fragments of these polypeptides may be readily prepared by one of skill in the art using known techniques, such as deletion mutagenesis and expression.

The *C. trachomatis* MOMP antigens of the present invention may also be constructed, using conventional genetic engineering techniques as part of a larger and/or multimeric protein or protein compositions. Antigens of this invention may be in combination with outer surface proteins or other proteins or antigens of other pathogens, such as those described herein, or various fragments of the antigens described herein may be in combination with each other. In such combination, the antigen may be in the form of a fusion protein. The antigen of the invention may be optionally fused to a selected polypeptide or protein derived from other microorganisms. For example, an antigen or polypeptide of this invention may be fused at its N-terminus or C-terminus to a polypeptide from another pathogen or to more than one polypeptide in sequence. Any polypeptides, without limitation, known by those of skill in the art to be useful for this purpose may be used in such embodiments.

A *C. trachomatis* MOMP antigen of the present invention may also be used in the form of a pharmaceutically acceptable salt. Suitable acids and bases which are capable of forming salts with the polypeptides of the present invention are well known to those of skill in the art, and include inorganic and organic acids and bases.

6.3.1. Immunogenic Compositions Comprising *C. trachomatis* Antigens

In another aspect, the invention provides immunogenic compositions comprising one or more *C. trachomatis* antigens as described above. In certain embodiments, the immunogenic compositions comprise one or more *C. trachomatis* MOMP antigen(s) as described above and a pharmaceutically acceptable vehicle, carrier, excipient, or diluent. Preferably, the immunogenic compositions induce a protective immune response when administered to a subject. In certain embodiments, the induced immune response is effective to reduce or prevent adherence of *C. trachomatis* to an epithelial cell. In certain embodiments, the induced immune response is effective to reduce the severity of a *C. trachomatis* infection in the subject. In certain embodiments, the induced immune response is effective to prevent a *C. trachomatis* infection in the subject following exposure to *C. trachomatis*. In certain embodiments, the induced immune response is effective to treat a *C. trachomatis* infection in the subject. In certain embodiments, the induced immune response is effective to treat a disease, or a symptom thereof, mediated by *C. trachomatis* infection in the subject. In certain embodiments, the induced immune response is effective to treat or prevent one or more symptoms associated with *C. trachomatis* infection in a subject.

The immunogenic compositions can be administered to a human for the treatment or prevention of *C. trachomatis* infection being. Thus, the immunogenic compositions are generally compatible with administration to a human. In certain embodiments, the immunogenic compositions can be in any suitable solid or liquid form for pharmaceutical administration, e.g., in liquid administration forms, as a gel, or any other support allowing controlled release, for example. For example, the immunogenic composition can be an injectable composition, e.g., an immunogenic composition formulated for injection into the blood in a human.

The compositions of the invention can also comprise components that increase the immunogenicity of a *C. trachomatis* antigen. For example, the immunogenic compositions can comprise immunogenic peptides other than *C. trachomatis* antigens, specific or nonspecific immunogenic adjuvants such as, e.g., alum, QS21, Freund's adjuvant, $SBA_2$ adjuvant, montanide, polysaccharides, lipopolysaccharides, lipopolysaccharide derivatives, lipid A, CpG-containing nucleic acids, non-CpG containing nucleic acids, or equivalent compounds. The antigen may also be modified by other techniques, such as denaturation with heat and/or SDS.

In an alternate embodiment, the immunogenic compositions may also comprise nucleic acids that express one or more *C. trachomatis* antigen(s) described above. For example, when injecting naked DNA encoding a *C. trachomatis* antigen as described above, this injection can result in expression of the encoded antigen and an immune response against the antigen. It is also possible to use naked DNA systems that comprise expression system or expression vectors. The expression vectors can in some cases improve the activity of the expressed antigens. Any suitable immunization system employing DNA known by one of skill in the art, whether as part of an expression system or not, can be used to administer DNA to a subject. Examples of such immunization systems can be found, for example, in International Patent Publication No. WO 95/111307 and in Bot et al., 1996, *Viral Immunol* 9:207. Additional exemplary vectors for in vivo gene delivery and include, e.g., adeno-associated virus (International patent application No. PCT/US91/03440), adenovirus vectors (Kay et al., 1994, *Proc. Natl. Acad. Sci. USA* 91:2353; Ishibashi et al., 1993, *J. Clin. Invest.* 92:883), or other viral vectors, e.g., various poxviruses, vaccinia, etc. Methods for insertion of a desired gene, e.g., a *C. trachomatis* antigen and obtaining in vivo expression of the encoded protein are well known to those of skill in the art. In certain embodiments, vectors incorporating sequences that are capable of increasing the immunogenicity of the *C. trachomatis* antigens of the present invention, such as CPG sequences, the GMCSF (granulocyte macrophage colony stimulating factor) gene, or cytokine genes can be employed. The specific constructions depend on the host, the epitope and on the vector selected.

6.3.2. Methods of Expressing *C. trachomatis* Antigens

Any suitable expression system known by one of skill in the art for producing a peptide, polypeptide, or nucleic acid antigen can be used to produce the *C. trachomatis* antigens of the invention. To produce recombinant peptide *C. trachomatis* antigens, the nucleic acid sequences encoding the antigens can be inserted into a suitable expression system. Desirably, a recombinant molecule or vector can be constructed in which the polynucleotide sequence encoding the selected protein, e.g., a *C. trachomatis* antigen, is operably linked to a heterologous expression control sequence permitting expression of the protein. Numerous types of appropriate expression vectors are known in the art for protein expression by standard molecular biology techniques. Such vectors can be selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known. See, e.g., Sambrook et al., 2001, *Molecular Cloning—A Laboratory Manual*, 3$^{rd}$ edition, Cold Spring Harbor Laboratory, Cold Spring Harbor, N.Y., and Ausubel et al., eds., Current Edition, *Current Protocols in Molecular Biology*, Greene Publishing Associates and Wiley Interscience, NY, and references cited therein.

Suitable host cells or cell lines for transfection by this method include bacterial cells, such as, for example, *E. coli* (e.g., HB101, MC1061, etc.) *B. subtilis*, *Pseudomonas* ssp., Streptomyces ssp., and the like; and mammalian cells, such as, for example, human 293 cells, Chinese hamster ovary cells (CHO), monkey COS-1 cells, and murine 3T3 cells. Indeed, any suitable host cell, method for transfection, culture, amplification, screening, production, purification, etc. known to one of skill in the art can be used to produce a *C. trachomatis* antigen. Further, strains of yeast cells or other fungal systems known to those skilled in the art are also available as host cells for expression of the antigens of the present invention. Alternatively, insect cells such as *Spodoptera frugipedera* (Sf9) cells may be used.

Thus, the present invention provides a method for producing recombinant *C. trachomatis* antigen that comprises transfecting, e.g., by conventional means such as electroporation, a host cell with at least one expression vector containing a polynucleotide encoding the *C. trachomatis* antigen under the control of a transcriptional regulatory sequence. The transfected or transformed host cell can be then cultured under conditions that allow expression of the protein. The expressed protein can be recovered, isolated, and optionally purified from the cell (or from the culture medium, if expressed extracellularly) by appropriate means known to one of skill in the art.

For example, the antigens can be isolated in soluble form following cell lysis, or extracted using known techniques, e.g., in guanidine chloride. If desired, the proteins or fragments of the invention are produced as a fusion protein such as those described above. Alternatively, for example, it may be desirable to produce fusion proteins to enhance expression of the antigen in a selected host cell, to improve purification, or for use in monitoring the presence of the antigen in tissues, cells or cell extracts. Suitable fusion partners for the proteins of the invention are well known to those of skill in the art and include, among others, β-galactosidase, glutathione-S-transferase, poly-histidine and maltose binding protein.

Thus, the invention also provides a method for preparing a *C. trachomatis* antigen of the invention by transforming a host cell using an expression vector (plasmid, cosmid, virus, etc.) comprising DNA sequences encoding the antigens of the invention, and culturing the transformed host cell and recovering the peptide in the culture medium.

The invention further provides a vector (either cloning and/or expression) and a host cell (prokaryotic or eukaryotic) transformed by the vector and comprising regulating elements allowing expression of the nucleotide sequence coding for a antigen of the invention.

6.4. Methods for Inducing an Immune Response

In another aspect, the invention provides methods of inducing an immune response against an antigen. The methods allow one of skill in the art to induce a cellular, humoral, and/or mucosal immune response. These methods comprise administration of a chimeric immunogen of the invention to a subject in whom the immune response is to be induced. Alternatively, an immunogenic composition as described herein can be administered to the subject in whom the immune response is to be induced. As described above, the chimeric immunogens can be used to induce an immune response that is specific for a heterologous antigen. In certain embodiments, the immune response that is induced is a prophylactic immune response, i.e., the subject is not already afflicted with a disease from which the heterologous antigen is derived. In other embodiments, the immune response that is induced is therapeutic, i.e., the subject is already afflicted with a disease from which the heterologous antigen is derived.

Accordingly, the invention provides methods for inducing an immune response against a heterologous antigen. In certain embodiments, the methods comprise administering to a subject in whom the immune response is to be induced a chimeric immunogen bearing the heterologous antigen. The chimeric immunogen can be administered as a vaccine composition, as described below. The resultant immune responses protect against infection by a pathogen bearing the heterologous antigen or against cells that express the heterologous antigen. For example, in the context of a *Chlamydia* infection, the immune response is mounted against the bacteria, themselves, or against cells containing intracellular *Chlamydia* bacteria.

Accordingly, in certain aspects, the invention provides a method for inducing an immune response in a subject that comprising administering to the subject an immunogenic amount of a chimeric immunogen comprising a receptor binding domain, a translocation domain, and a *C. trachomatis* antigen that comprises or is an amino acid sequence that is selected from the group consisting of AGTEAA (SEQ ID NO.:4), AGTDAA (SEQ ID NO.:5), AETIFDVTTLNPTIAGAGDVKTSAEG (SEQ ID NO.:6), AETILDVTTLNPTIAGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKPKGYVGKE (SEQ ID NO.:11), ILWEGFGGDPCDPCTT (SEQ ID NO.:12), ALNIWDRFDV (SEQ ID NO.:13), KMKSRKSCGIAVGTTVVSADKYAVT (SEQ ID NO.: 14), CAETIFDVTTLNPTIAGAGDVKTSAEGC (SEQ ID NO.: 15), CAETILDVTTLNPTIAGKGTVVTSAEC (SEQ ID NO.:16), CTTLNPTIAGC (SEQ ID NO.: 17), CGAKPTATTGNATAPSTLTAREC (SEQ ID NO.:18), and CTTSDVAGLQNDPC (SEQ ID NO.:19). In certain embodiments, the *C. trachomatis* antigen is a peptide of one of these sequences. In certain embodiments, the chimeric immunogen comprises, 1, 2, 3, 4, 5, 6, 7, 8, 9, or more of these *C. trachomatis* antigens.

In certain embodiments, administration of the chimeric immunogen to a subject induces an immune response in the subject that is effective to reduce adherence of a microorganism expressing the *C. trachomatis* antigen to epithelial cells of the subject. In certain embodiments, administration of the chimeric immunogen to a subject induces an immune response in the subject that is effective to reduce risk of infection or disease, or prevent infection of or disease in the subject by a microorganism expressing the *C. trachomatis* antigen. In certain embodiments, administration of the chimeric immunogen to a subject induces an immune response in the subject that is effective to treat an infection of the subject by a microorganism expressing the *C. trachomatis* antigen. In certain embodiments, the microorganism is a *Chlamydia* bacterium. In certain embodiments, the microorganism is *C. trachomatis*. In certain embodiments, administration of the chimeric immunogen to a subject induces the production of interferon-γ(IFN-γ) in the subject. In certain embodiments, administration of the chimeric immunogen to a subject induces an immune response that increases the rate of clearance of an infection from the subject. In certain embodiments, the infection is a *Chlamydia* infection. In certain embodiments, the infection is a *C. trachomatis* infection. In certain embodiments, administration of the chimeric immunogen to a subject induces an immune response in the subject that is effective to reduce attachment of a microorganism expressing a *C. trachomatis* antigen to a cell of the subject. In certain embodiments, administration of the chimeric immunogen to a subject induces an immune response in the subject that is effective to reduce uptake by a cell of the subject of a microorganism expressing a *C. trachomatis* antigen. In certain embodiments, the cell is a epithelial, macrophage, dendritic, T-lymphocyte, B-lymphocyte, or leukocyte. In certain embodiments, the cell can be any cell known by one of skill in the art to be infected during chlamydial infection. In certain embodiments, administration of the chimeric immunogen to a subject induces an immune response in the subject that is effective to reduce the bacterial load of a subject infected with a microorganism expressing a *C. trachomatis* antigen. In certain embodiments, administration of the chimeric immunogen to a subject induces an immune response in the subject that is effective to reduce the probability that the subject will be infected with HIV following exposure to a human immunodeficiency virus. In certain embodiments, administration of the chimeric immunogen to a subject induces an immune response in the subject that reduces cytotoxicity of *Pseudomonas* exotoxin A.

In certain embodiments, the subject is a human. In certain embodiments, the chimeric immunogen is administered to a mucosal surface of said subject, e.g., nasally, orally, or vaginally.

In certain embodiments, the chimeric immunogen is administered in the form of a pharmaceutical composition that comprises the chimeric immunogen and a pharmaceutically acceptable diluent, excipient, vehicle, or carrier. In certain embodiments, the pharmaceutical composition is formulated for nasal or oral administration.

In other embodiments, the invention provides a method for generating in a subject antibodies specific for a *C. trachomatis* antigen having an amino acid sequence that is selected from the group consisting of AGTEAA (SEQ ID NO.:4), AGTDAA (SEQ ID NO.:5), AETIPDVTTLNPTIAGAGD-VKTSAEG (SEQ ID NO.:6), AETILDVTTLNPTI-AGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKP-KGYVGKE (SEQ ID NO.:11), ILWEGFGGDPCDPCTT (SEQ ID NO.:12), ALNIWDRFDV (SEQ ID NO.:13), KMKSRKSCGIAVGTTVVSADKYAVT (SEQ ID NO.:14), CAETIFDVTTLNPTIAGAGDVKTSAEGC (SEQ ID NO.:15), CAETILDVTTLNPTIAGKGTVVTSAEC (SEQ ID NO.:16), CTTLNPTIAGC (SEQ ID NO.: 17), CGAKPTAT-TGNATAPSTLTAREC (SEQ ID NO.:18), and CTTSDVA-GLQNDPC (SEQ ID NO.:19). In certain embodiments, the *C. trachomatis* antigen is a peptide of one of these sequences. In certain embodiments, the chimeric immunogen comprises, 1, 2, 3, 4, 5, 6, 7, 8, 9, or more of these *C. trachomatis* antigens. In some embodiments, the method comprises administering to the subject an immunogenic amount of a chimeric immunogen that comprises a receptor binding domain, a translocation domain, and a *C. trachomatis* antigen that comprises an amino acid sequence that is selected from the group consisting of AGTEAA (SEQ ID NO.:4), AGT-DAA (SEQ ID NO.:5), AETIFDVTTLNPTIAGAGDVKT-SAEG (SEQ ID NO.:6), AETILDVTTLNPTIAGKGTVVT-SAE (SEQ ID NO.:7), TTLNPTIAGC (SEQ ID NO.:8), GAKPTATTGNATAPSTLTARE (SEQ ID NO.:9), TTSD-VAGLQNDPC (SEQ ID NO.:10), SEFTINKPKGYVGKE (SEQ ID NO.:11), ILWEGFGGDPCDPCTT (SEQ ID NO.:12), ALNIWDRFDV (SEQ ID NO.:13), KMKSRKSCGIA-VGTTVVSADKYAVT (SEQ ID NO.:14), CAETIFDVTTL-NPTIAGAGDVKTSAEGC (SEQ ID NO.:15), CAETILDVTTLNPTIAGKGTVVTSAEC (SEQ ID NO.:16), CTTLNPTIAGC (SEQ ID NO.:17), CGAKPTAT-TGNATAPSTLTAREC (SEQ ID NO.:18), and CTTSDVA-GLQNDPC (SEQ ID NO.:19). In certain embodiments, the *C. trachomatis* antigen is a peptide of one of these sequences. In certain embodiments, the chimeric immunogen comprises, 1, 2, 3, 4, 5, 6, 7, 8, 9, or more of these *C. trachomatis* antigens. Administration of such chimeric immunogens to a subject generates antibodies that bind the *C. trachomatis* antigen. Preferably, such antibodies are specific for the *C. trachomatis* antigen.

In certain embodiments, the methods comprise administering a chimeric immunogen of the invention to a subject two, three, four, five, six, seven, eight, nine, ten, eleven, twelve, fifteen, twenty, or more times. In certain embodiments, the chimeric immunogen can be administered at regular intervals until death of the subject. The administration can be by any method described here, e.g., nasally, orally, by injection, etc. Further, the administrations can be separated by as little as, e.g., about 1 month or as much as e.g., about ten or more years. In certain embodiments, the administrations can be at regular periods, e.g., about every six months, about every year, about every 18 months, about every two years. In other embodiments, the administrations can be irregular, e.g., a second administration after about three months of the first administration, then a third administration at about 2 years after the first. In still other embodiments, the administration can be variously irregular and regular, e.g., a second administration after about three months of the first administration, then a third administration at about 2 years after the first and further administrations every two years thereafter. In certain embodiments, the administrations are separated by about 1, 2, 3, 4, 5, 6, 7, 8, 9, 10, 11, or 12 months. In certain embodiments, the administrations are separated by about 1, 2, 3, 4, 5, 6, 7, 8, 9, 10, 11, or 12 years.

In certain embodiments, the subject is a mammal. In further embodiments, the subject is a rodent, lagomorph or primate. In a preferred embodiments, the subject is a human.

6.4.1. Humoral Immune Responses

In certain embodiments, the invention provides a method for inducing a humoral immune response against the heterologous antigen in a subject. The methods generally comprise administering to a subject a chimeric immunogen that is configured to produce a humoral immune response. Such immune responses generally involve the production of antibodies specific for the antigen. Certain embodiments of the chimeric immunogens have properties that allow the skilled artisan to induce a humoral immune response against the heterologous antigens. For example, when the heterologous antigen is inserted into PE domain Ib, the flanking cysteines cause the heterologous antigen to be extended from the remainder of the immunogen and facilitate recognition of the antigen by a B cell through an interaction with a B-cell receptor. Interaction between the heterologous antigen and the B cell receptor stimulates clonal expansion of the B cell bearing the receptor, eventually resulting in a population of plasma cells that secrete antibodies specific for the antigen.

In most circumstances, B cell recognition of antigen is necessary, but not sufficient, to induce a robust humoral immune response. The humoral response is greatly potentiated by $CD4^+$ (helper) T cell signaling to B cells primed by antigen recognition. Helper T cells are activated to provide such signals to B cells by recognition of antigen processed through the Class II MHC pathway. The antigen recognized by the T cell can, but need not, be the same antigen recognized by the B cell. The chimeric immunogens of the invention can be targeted to such antigen presenting cells for processing in the Class II MHC pathway in order to stimulate helper T cells to activate B cells. By doing so, the chimeric immunogens can be used to stimulate a robust humoral immune response that is specific for the heterologous antigen.

Further, the chimeric immunogens are attractive vehicles for inducing a humoral immune response against heterologous antigens that are constrained within their native environment. By inserting the heterologous antigen into the Ib loop of PE antigens, the antigen can be presented to immune cells in near-native conformation. The resulting antibodies generally recognize the native antigen better than those raised against unconstrained versions of the heterologous antigen. The Ib loop can also be used to present B cell antigens that are not constrained in their native environment. In such embodiments, the antigen inserted into the Ib loop should be flanked by a sufficient number of amino acids that give conformational flexibility, such as, e.g., glycine, serine, etc., to allow the antigen to fold into its native form and avoid constraint by the disulfide linkage between the cysteines of the Ib loop.

The humoral immune response induced by the chimeric immunogens can be assessed using any method known by one of skill in the art without limitation. For example, an animal's immune response against the heterologous antigen can be monitored by taking test bleeds and determining the titer of antibody reactivity to the heterologous antigen. When appropriately high titers of antibody to the heterologous antigen are obtained, blood can be collected from the animal and antisera prepared. The antisera can be further enriched for antibodies reactive to the heterologous antigen, when desired. See, e.g., Coligan, 1991, *Current Protocols in Immunology*, Greene Publishing Associates and Wiley Interscience, NY; and Harlow and Lane, 1989, *Antibodies: A Laboratory Manual*, Cold Spring Harbor Press, NY.

Antibodies produced in response to administration of the chimeric immunogens can then be used for any purpose known by one of skill in the art, without limitation. The antibodies are believed to be equivalent to antibodies induced using conventional techniques, such as coupling peptides to an immunogen. For example, the antibodies can be used to make monoclonal antibodies, humanized antibodies, chimeric antibodies or antibody fragments. Techniques for producing such antibody derivatives may be found in, for example, Stites et al. eds., 1997, *Medical Immunology* (9th ed.), McGraw-Hill/Appleton & Lange, CA; Harlow and Lane, 1989, *Antibodies: A Laboratory Manual*, Cold Spring Harbor Press, NY; Goding, 1986, *Monoclonal Antibodies: Principles and Practice* (2d ed.), Academic Press, NY; Kohler and Milstein, 1975, *Nature* 256: 495-497; and U.S. Pat. No. 5,585,089.

6.4.2. Cell-Mediated Immune Responses

In other embodiments, the invention provides methods for eliciting a cell-mediated immune response against cells expressing the heterologous antigen. The methods generally comprise administering to a subject a chimeric immunogen that comprises the heterologous antigen that is configured to produce a cell-mediated immune response. Such immune responses generally involve the activation of cytotoxic T lymphocytes that can recognize and kill cells that display the antigen on their surfaces. However, certain aspects of humoral immune responses give rise to cell-mediated effects as well, as described below. Certain embodiments of the chimeric immunogens have properties that allow the skilled artisan to induce a cell-mediated immune response against the heterologous antigens.

In particular, heterologous antigens that are inserted into a chimeric immunogen near a ER retention signal tend to induce a cell-mediated immune response. In one embodiment, a heterologous antigen is near an ER retention signal when it is within about 50 amino acids away from the ER retention signal. In certain embodiments, the about 50 amino acids are endogenous to the heterologous antigen. In certain embodiments, the about 50 amino acids are heterologous to the heterologous antigen. In certain embodiments, the about 50 amino acids are endogenous to the ER retention domain. In certain embodiments, the about 50 amino acids are heterologous to the ER retention domain. Without intending to be bound to any particular theory or mechanism of action, it is believed that the ER retention signal causes the chimeric immunogen to be trafficked from an endosome to the ER, and from thence into the cytosol. Still not intending to be bound to any theory, once in the cytosol, peptides from the immunogen, including the heterologous antigen, enter the Class I MHC processing pathway. The peptides associate with Class I MHC and are presented on the surface of the cell into which the immunogen has been introduced. $CD8^+$ (cytotoxic) T lymphocytes then recognize the heterologous antigen in association with Class I MHC and thereby become activated and primed to kill cells that similarly have the heterologous antigen associated with Class I MHC on their surfaces.

Without intending to be bound to any particular theory or mechanism of action, part of the processing that occurs during presentation on Class I MHC is believed to result in degradation of the chimeric immunogen into peptides that can associate with the MHC molecule. This proteolysis is believed to begin in the endosome and to continue in the cytosol. If, in the course of this process, the heterologous antigen is separated from the ER retention signal before the heterologous antigen is trafficked to the cytosol, it is believed that the heterologous antigen cannot associate with Class I MHC. In such circumstances, the heterologous antigen can remain in the endosome, and can be directed to the Class II MHC processing pathway. Accordingly, it is believed that the distance, e.g., the number of amino acids, between the heterologous antigen and the ER retention signal can affect the degree to which the antigen is presented in association with Class I or Class II MHC.

Features of peptides that associate with the various allelic forms of Class I MHC have been well characterized. For example, peptides bound by HLA-A1 generally comprise a first conserved residue of T, S or M, a second conserved residue of D or E, and a third conserved residue of Y, wherein the first and second residues are adjacent, and both are separated from the third residue by six or seven amino acids. Peptides that bind to other alleles of Class I MHC have also been characterized. Using this knowledge, the skilled artisan can select heterologous antigens that can associate with a Class I MHC allele that is expressed in the subject. By administering chimeric immunogens comprising such antigens near the ER retention signal, a cell-mediated immune response can be induced.

Cell-mediated immune responses can also arise as a consequence of humoral immune responses. Antibodies produced in the course of the humoral immune response bind to their cognate antigen; if this antigen is present on the surface of a cell, the antibody binds to the cell surface. Cells bound by antibodies in this manner are subject to antibody-dependent cell-mediated cytotoxicity, in which immune cells that bear Fc receptors attack the marked cells. For example, natural killer cells and macrophages have Fc receptors and can participate in this phenomenon.

6.4.3. Mucosal Immune Response

In other embodiments, the invention provides methods for eliciting a mucosal immune response against the heterologous antigen. The methods generally comprise administering to a mucous membrane of the subject a chimeric immunogen that comprises the heterologous antigen that is configured to bind to a receptor present on the mucous membrane. The mucous membrane can be any mucous membrane known by one of skill in the art to be present in the subject, without limitation. For example, the mucous membrane can be present in the eye, nose, mouth, trachea, lungs, esophagus, stomach, small intestine, large intestine, rectum, anus, sweat glands, vulva, vagina, or penis of the subject. Preferably, the mucous membrane is in the nose. Certain embodiments of the chimeric immunogens have properties that allow the skilled artisan to induce a mucosal immune response against the heterologous antigens.

In particular, chimeric immunogens that comprise receptor binding domains that can bind to a receptor present on the apical membrane of an epithelial cell can be used to induce a mucosal immune response. Such receptor binding domains are extensively described above. Without intending to be bound by any particular theory or mechanism of action, it is believed that the original encounter with the antigen at the mucosal surface directs the immune system to produce a mucosal rather than humoral immune response.

Mucosal immune responses are desirable for protecting against any pathogen that enters the body through a mucous membrane. Mucous membranes, particularly genital mucous membranes, are primary entryways for many infectious pathogens, including, for example, *Chlamydia* ssp. Mucous membranes can be found in the mouth, nose, throat, lung, vagina, rectum and colon. As one defense against entry by these pathogens, the body secretes secretory IgA from mucosal epithelial membranes that can bind the pathogens and prevent or deter pathogenesis. Furthermore, antigens presented at one mucosal surface can trigger responses at other mucosal surfaces due to trafficking of antibody-secreting cells between the mucous membranes. The structure of secretory IgA appears to be crucial for its sustained residence and effective function at the luminal surface of a mucous membrane. “Secretory IgA” or “sIgA” generally refers to a polymeric molecule comprising two IgA immunoglobulins joined by a J chain and further bound to a secretory component. While mucosal administration of antigens can generate an IgG response, parenteral administration of immunogens rarely produces strong sIgA responses.

The chimeric immunogens can be administered to the mucous membrane of the subject by any suitable method or in any suitable formulation known to one of skill in the art without limitation. For example, the chimeric immunogens can be administered in the form of liquids or solids, e.g., sprays, ointments, suppositories or erodible polymers impregnated with the immunogen. Administration can involve applying the immunogen to a one or more different mucosal surfaces. Further, in certain embodiments, the chimeric immunogen can be administered in a single dose. In other embodiments, the chimeric immunogen can be administered in a series of two or more administrations. In certain embodiments, the second or subsequent administration of the chimeric immunogen is administered parenterally, e.g., subcutaneously or intramuscularly.

The sIgA response is strongest on mucosal surfaces exposed to the immunogen. Therefore, in certain embodiment, the immunogen is applied to a mucosal surface that is likely to be a site of exposure to the pathogen. Accordingly, chimeric immunogens against pathogens encountered on vaginal, anal, or oral mucous membranes are preferably administered to vaginal, anal or oral mucosal surfaces, respectively. However, nasal administration of the chimeric immunogens can also induce robust mucosal immune responses from other mucous membranes including, for example, vaginal, anal, urethral, etc. mucous membranes. See, for example, Boyaka et al., 2003, *Cur. Pharm. Des.* 9:1965-1972, and the Examples below.

Mucosal administration of the chimeric immunogens of this invention result in strong memory responses, both for IgA and IgG. These memory responses can advantageously be boosted by re-administering the chimeric immunogen after a period of time. Such booster administrations can be administered either mucosally or parenterally. The memory response can be elicited by administering a booster dose more than a year after the initial dose. For example, a booster dose can be administered about 12, about 16, about 20 or about 24 months after the initial dose.

6.5. Polynucleotides Encoding Chimeric Immunogens

In another aspect, the invention provides polynucleotides comprising a nucleotide sequence encoding a chimeric immunogen of the invention as described herein. These polynucleotides are useful, for example, for making the chimeric immunogens. In yet another aspect, the invention provides an expression system that comprises a recombinant polynucleotide sequence encoding a receptor binding domain, a translocation domain, an optional ER retention domain, and an insertion site for a polynucleotide sequence encoding a heterologous antigen. The insertion site can be anywhere in the polynucleotide sequence so long as the insertion does not disrupt the receptor binding domain, the translocation domain, or the optional ER retention domain. Preferably, the insertion site is between the translocation domain and the ER retention domain. In other equally preferred embodiments, the insertion site is in the ER retention domain.

In certain embodiments, the recombinant polynucleotides are based on polynucleotides encoding PE, or portions or derivatives thereof. In other embodiments, the recombinant polynucleotides are based on polynucleotides that hybridize to a polynucleotide that encodes PE under stringent hybridization conditions. A nucleotide sequence encoding PE is presented as SEQ ID NO.:41. This sequence can be used to prepare PCR primers for isolating a nucleic acid that encodes any portion of this sequence that is desired. For example, PCR can be used to isolate a nucleic acid that encodes one or more of the functional domains of PE. A nucleic acid so isolated can then be joined to nucleic acids encoding other functional domains of the chimeric immunogens using standard recombinant techniques.

Other in vitro methods that can be used to prepare a polynucleotide encoding PE, PE domains, or any other functional domain useful in the chimeric immunogens of the invention include, but are not limited to, reverse transcription, the polymerase chain reaction (PCR), the ligase chain reaction (LCR), the transcription-based amplification system (TAS), the self-sustained sequence replication system (3SR) and the QP replicase amplification system (QB). Any such technique known by one of skill in the art to be useful in construction of recombinant nucleic acids can be used. For example, a polynucleotide encoding the protein or a portion thereof can be isolated by polymerase chain reaction of cDNA using primers based on the DNA sequence of PE or another polynucleotide encoding a receptor binding domain.

Guidance for using these cloning and in vitro amplification methodologies are described in, for example, U.S. Pat. No. 4,683,195; Mullis et al, 1987, *Cold Spring Harbor Symp. Quant. Biol.* 51:263; and Erlich, ed., 1989, *PCR Technology*, Stockton Press, NY. Polynucleotides encoding a chimeric immunogen or a portion thereof also can be isolated by screening genomic or cDNA libraries with probes selected from the sequences of the desired polynucleotide under stringent, moderately stringent, or highly stringent hybridization conditions.

Construction of nucleic acids encoding the chimeric immunogens of the invention can be facilitated by introducing an insertion site for a nucleic acid encoding the heterologous antigen into the construct. In certain embodiments, an insertion site for the heterologous antigen can be introduced between the nucleotides encoding the cysteine residues of domain Ib. In other embodiments, the insertion site can be introduced anywhere in the nucleic acid encoding the immunogen so long as the insertion does not disrupt the functional domains encoded thereby. In certain embodiments, the insertion site can be in the ER retention domain. In certain embodiments, the insertion site is introduced into the nucleic acid encoding the chimeric immunogen. In other embodiments, the nucleic acid comprising the insertion site can replace a portion of the nucleic acid encoding the immunogen, as long as the replacement does not disrupt the receptor binding domain or the translocation domain.

In more specific embodiments, the insertion site comprises that includes a cloning site cleaved by a restriction enzyme. In certain embodiments, the cloning site can be recognized and cleaved by a single restriction enzyme, for example, by PstI. In such examples, a polynucleotide encoding heterologous antigen that is flanked by PstI sequences can be inserted into the vector. In other embodiments, the insertion site comprises a polylinker that comprises about one, about two, about three, about four, about five, about ten, about twenty or more cloning sites, each of which can be cleaved by one or more restriction enzymes.

Further, the polynucleotides can also encode a secretory sequence at the amino terminus of the encoded chimeric immunogen. Such constructs are useful for producing the chimeric immunogens in mammalian cells as they simplify isolation of the immunogen.

Furthermore, the polynucleotides of the invention also encompass derivative versions of polynucleotides encoding a chimeric immunogen. Such derivatives can be made by any method known by one of skill in the art without limitation. For example, derivatives can be made by site-specific mutagenesis, including substitution, insertion, or deletion of one, two, three, five, ten or more nucleotides, of polynucleotides encoding the chimeric immunogen. Alternatively, derivatives can be made by random mutagenesis. One method for randomly mutagenizing a nucleic acid comprises amplifying the nucleic acid in a PCR reaction in the presence of 0.1 mM $MnCl_2$ and unbalanced nucleotide concentrations. These conditions increase the misincorporation rate of the polymerase used in the PCR reaction and result in random mutagenesis of the amplified nucleic acid.

Several site-specific mutations and deletions in chimeric molecules derived from PE have been made and characterized. For example, deletion of nucleotides encoding amino acids 1-252 of PE yields a construct referred to as "PE40." Deleting nucleotides encoding amino acids 1-279 of PE yields a construct referred to as "PE37." See U.S. Pat. No. 5,602,095. In both of these constructs, the receptor binding domain of PE, i.e., domain Ia, has been deleted. Nucleic acids encoding a receptor binding domain can be ligated to these constructs to produce chimeric immunogens that are targeted to the cell surface receptor recognized by the receptor binding domain. Of course, these constructs are particularly useful for expressing chimeric immunogens that have a receptor binding domain that is not domain Ia of PE. The constructs can optionally encode an amino-terminal methionine to assist in expression of the construct. In certain embodiments, the receptor binding domain can be ligated to the 5' end of the polynucleotide encoding the translocation domain and optional ER retention domain. In other embodiments, the polynucleotide can be inserted into the constructs in the nucleotide sequence encoding the ER retention domain.

Other nucleic acids encoding mutant forms of PE that can be used as a source of nucleic acids for constructing the chimeric immunogens of the invention include, but are not limited to, PEΔ553 and those described in U.S. Pat. Nos. 5,602,095; 5,512,658 and 5,458,878, and in Vasil et al., 1986, *Infect. Immunol.* 52:538-48.

Accordingly, in certain aspects, the invention provides a polynucleotide that encodes a chimeric immunogen that comprises a receptor binding domain, a translocation domain, and a *C. trachomatis* antigen that comprises an amino acid sequence that is selected from the group consisting of AGTEAA (SEQ ID NO.:4), AGTDAA (SEQ ID NO.:5), AETIFDVTTLNPTIAGAGDVKTSAEG (SEQ ID NO.:6), AETILDVTTLNPTIAGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKPKGYVGKE (SEQ ID NO.:11), ILWEGFGGDPCDPCTT (SEQ ID NO.:12), ALNIWDRFDV (SEQ ID NO.:13), KMKSRKSCGIAVGTTVVSADKYAVT (SEQ ID NO.: 14), CAETIFDVTTLNPTIAGAGDVKTSAEGC (SEQ ID NO.:15), CAETILDVTTLNPTIAGKGTVVTSAEC (SEQ ID NO.:16), CTTLNPTIAGC (SEQ ID NO.: 17), CGAKPTATTGNATAPSTLTAREC (SEQ ID NO.:18), and CTTSDVAGLQNDPC (SEQ ID NO.:19). In certain embodiments, the chimeric immunogen, when administered to a subject, induces an immune response in the subject that is effective to reduce adherence of a microorganism that expresses the *C. trachomatis* antigen to epithelial cells of the subject. In certain embodiments, the chimeric immunogen, when administered to the subject, generates an immune response in the subject that reduces the cytotoxicity of *Pseudomonas* exotoxin A.

In certain embodiments, polynucleotide encodes a chimeric immunogen further comprising an endoplasmic reticulum retention domain. In further embodiments, the *C. trachomatis* antigen is located between the translocation domain and the endoplasmic reticulum retention domain. In certain embodiments, the endoplasmic reticulum retention domain is an enzymatically-inactive domain III of *Pseudomonas* exotoxin A. In certain embodiments, the enzymatically inactive domain III of *Pseudomonas* exotoxin A is inactivated by deleting a glutamate at position 553. In certain embodiments, the endoplasmic reticulum retention domain comprises an amino acid sequence that is selected from the group of RDEL (SEQ ID NO.:20) or KDEL (SEQ ID NO.:21) that is sufficiently near the C-terminus of said endoplasmic reticulum retention domain to result in retention of said chimeric immunogen in the endoplasmic reticulum.

In certain embodiments, the polynucleotide encodes a translocation domain that is selected from the group consisting translocation domains from *Pseudomonas* exotoxin A, diptheria toxin, pertussis toxin, cholera toxin, heat-labile *E. coli* enterotoxin, shiga toxin, and shiga-like toxin. In certain embodiments, the translocation domain is domain II of *Pseudomonas* exotoxin A. In further embodiments, the translocation domain comprises amino acids 280 to 364 of domain II of *Pseudomonas* exotoxin A.

In certain embodiments, the polynucleotide encodes a chimeric immunogen that comprises more than one of the *C. trachomatis* antigens.

In certain embodiments, the polynucleotide encodes a receptor binding domain that is selected from the group consisting of domain Ia of *Pseudomonas* exotoxin A; a receptor binding domains from cholera toxin, diptheria toxin, shiga toxin, or shiga-like toxin; a monoclonal antibody, a polyclonal antibody, or a single-chain antibody; TGFα, TGFβ, EGF, PDGF, IGF, or FGF; IL-1, IL-2, IL-3, or IL-6; and MIP-1α, MIP-1b, MCAF, or IL-8. In certain embodiments, the receptor binding domain is domain Ia of *Pseudomonas* exotoxin A. In further embodiments, the domain Ia of *Pseudomonas* exotoxin A has an amino acid sequence that is SEQ ID NO.:22.

In certain embodiments, the receptor binding domain binds to α2-macroglobulin receptor, epidermal growth factor receptor, transferrin receptor, interleukin-2 receptor, interleukin-6 receptor, interleukin-8 receptor, Fc receptor, poly-IgG receptor, asialoglycopolypeptide receptor, CD3, CD4, CD8, chemokine receptor, CD25, CD11B, CD11C, CD80, CD86, TNFα receptor, TOLL receptor, M-CSF receptor, GM-CSF receptor, scavenger receptor, or VEGF receptor. In certain embodiments, the receptor binding domain binds to α2-macroglobulin receptor.

In certain embodiments, the polynucleotide encodes a chimeric immunogen that has an amino acid sequence that is selected from the group consisting of SEQ ID NOs.:23-33. In other embodiments, the polynucleotide hybridizes under stringent hybridization conditions to a polynucleotide that encodes a chimeric immunogen has an amino acid sequence that is SEQ ID NO.:23-33.

6.6. Expression Vectors

In still another aspect, the invention provides expression vectors for expressing the chimeric immunogens. Generally, expression vectors are recombinant polynucleotide molecules comprising expression control sequences operatively linked to a nucleotide sequence encoding a polypeptide. Expression vectors can readily be adapted for function in prokaryotes or eukaryotes by inclusion of appropriate promoters, replication sequences, selectable markers, etc. to result in stable transcription and translation of mRNA. Techniques for construction of expression vectors and expression of genes in cells comprising the expression vectors are well known in the art. See, e.g., Sambrook et al., 2001, *Molecular Cloning—A Laboratory Manual*, 3$^{rd}$ edition, Cold Spring Harbor Laboratory, Cold Spring Harbor, N.Y., and Ausubel et al., eds., Current Edition, *Current Protocols in Molecular Biology*, Greene Publishing Associates and Wiley Interscience, NY.

Useful promoters for use in expression vectors include, but are not limited to, a metallothionein promoter, a constitutive adenovirus major late promoter, a dexamethasone-inducible MMTV promoter, a SV40 promoter, a MRP pol III promoter, a constitutive MPSV promoter, a tetracycline-inducible CMV promoter (such as the human immediate-early CMV promoter), and a constitutive CMV promoter.

The expression vectors should contain expression and replication signals compatible with the cell in which the chimeric immunogens are expressed. Expression vectors useful for expressing chimeric immunogens include viral vectors such as retroviruses, adenoviruses and adenoassociated viruses, plasmid vectors, cosmids, and the like. Viral and plasmid vectors are preferred for transfecting the expression vectors into mammalian cells. For example, the expression vector pcDNA1 (Invitrogen, San Diego, Calif.), in which the expression control sequence comprises the CMV promoter, provides good rates of transfection and expression into such cells.

The expression vectors can be introduced into the cell for expression of the chimeric immunogens by any method known to one of skill in the art without limitation. Such methods include, but are not limited to, e.g., direct uptake of the molecule by a cell from solution; facilitated uptake through lipofection using, e.g., liposomes or immunoliposomes; particle-mediated transfection; etc. See, e.g., U.S. Pat. No. 5,272,065; Goeddel et al., eds, 1990, *Methods in Enzymology*, vol. 185, Academic Press, Inc., CA; Krieger, 1990, *Gene Transfer and Expression—A Laboratory Manual*, Stockton Press, NY; Sambrook et al., 2001, *Molecular Cloning—A Laboratory Manual,* 3rd edition, Cold Spring Harbor Laboratory, Cold Spring Harbor, N.Y., and Ausubel et al., eds., Current Edition, *Current Protocols in Molecular Biology*, Greene Publishing Associates and Wiley Interscience, NY.

The expression vectors can also contain a purification moiety that simplifies isolation of the protein. For example, a polyhistidine moiety of, e.g., six histidine residues, can be incorporated at the amino terminal end of the protein. The polyhistidine moiety allows convenient isolation of the protein in a single step by nickel-chelate chromatography. In certain embodiments, the purification moiety can be cleaved from the remainder of the chimeric immunogen following purification. In other embodiments, the moiety does not interfere with the function of the functional domains of the chimeric immunogen and thus need not be cleaved.

6.7. Cell for Expressing a Chimeric Immunogen

In yet another aspect, the invention provides a cell comprising an expression vector for expression of the chimeric immunogens, or portions thereof. The cell is preferably selected for its ability to express high concentrations of the chimeric immunogen to facilitate purification of the protein. In certain embodiments, the cell is a prokaryotic cell, for example, *E. coli*. As described in the examples, the chimeric immunogens are properly folded and comprise the appropriate disulfide linkages when expressed in *E. coli.*

In other embodiments, the cell is a eukaryotic cell. Useful eukaryotic cells include yeast and mammalian cells. Any mammalian cell known by one of skill in the art to be useful for expressing a recombinant polypeptide, without limitation, can be used to express the chimeric immunogens. For example, Chinese hamster ovary (CHO) cells can be used to express the chimeric immunogens.

6.8. Vaccines Comprising Chimeric Immunogens

In yet another aspect, the invention provides vaccines comprising one or more chimeric immunogens. The vaccines are useful for eliciting a protective immune response against the heterologous antigen, particularly against pathogens or cells bearing the heterologous antigen. A vaccine can include one or a plurality of chimeric immunogens. For example, a vaccine can include chimeric immunogens with heterologous antigens from several circulating strains of a pathogen, e.g., from more than one class of *C. trachomatis* or from more than one serovar of *C. trachomatis*. In certain embodiments, the composition can comprise a combination of chimeric immunogens that comprise a *C. trachomatis* antigen from two, three, four, five, six, seven, eight, nine, ten, eleven, twelve, thirteen, fourteen, fifteen, sixteen, seventeen, or more serovars of *C. trachomatis*. In certain embodiments, the composition comprises a combination of chimeric immunogens that, when administered to a subject, induces an immune response in the subject that recognizes a MOMP from more than one serovar. In certain embodiments, the composition comprises a combination of chimeric immunogens that, when administered to a subject, induces an immune response in the subject that recognizes a MOMP from each serovar.

6.8.1. Vaccine Compositions

The vaccines of the invention can be formulated as compositions. The compositions are generally formulated appropriately for the immediate use intended for the vaccine. For example, if the vaccine is not to be administered immediately, the vaccine can be formulated in a composition suitable for storage. One such composition is a lyophilized preparation of the vaccine together with a suitable stabilizer. Alternatively, the vaccine composition can be formulated for storage in a solution with one or more suitable stabilizers. Any such stabilizer known to one of skill in the art without limitation can be used. For example, stabilizers suitable for lyophilized preparations include, but are not limited to, sugars, salts, surfactants, proteins, chaotropic agents, lipids, and amino acids. Stabilizers suitable for liquid preparations include, but are not limited to, sugars, salts, surfactants, proteins, chaotropic agents, lipids, and amino acids. Specific stabilizers than can be used in the compositions include, but are not limited to, trehalose, serum albumin, phosphatidylcholine, lecithin, and arginine. Other compounds, compositions, and methods for stabilizing a lyophilized or liquid preparation of the delivery constructs may be found, for example, in U.S. Pat. Nos. 6,573,237, 6,525,102, 6,391,296, 6,255,284, 6,133,229, 6,007,791, 5,997,856, and 5,917,021.

Further, the vaccine compositions of the invention can be formulated for administration to a subject. The formulation can be suitable for administration to a nasal, oral, vaginal, rectal, or other mucosal surface. Such vaccine compositions generally comprise one or more chimeric immunogens of the invention and a pharmaceutically acceptable excipient, diluent, carrier, or vehicle. Any such pharmaceutically acceptable excipient, diluent, carrier, or vehicle known to one of skill in the art without limitation can be used. Examples of a suitable excipient, diluent, carrier, or vehicle can be found in *Remington's Pharmaceutical Sciences,* 19th Ed. 1995, Mack Publishing Co., Easton.

The vaccine compositions can also include an adjuvant that potentiates an immune response when used in administered in conjunction with the chimeric immunogen. Useful adjuvants, particularly for administration to human subjects, include, but are not limited to, alum, aluminum hydroxide, aluminum phosphate, CpG-containing oligonucleotides (both methylated and unmethylated), bacterial nucleic acids, lipopolysaccharide and lipopolysaccharide derivatives such as monophosphoryl lipid A, oil-in-water emulsions, etc. Other suitable adjuvants are described in Sheikh et al., 2000, *Cur. Opin. Mol. Ther.* 2:37-54. Adjuvants are most useful when the vaccine composition is to be injected rather than administered to a mucosal membrane of the subject. However, certain of the above adjuvants are also known in the art to be useful in compositions to be administered to mucosal surface.

In certain embodiments, the vaccine compositions are formulated for oral administration. In such embodiments, the vaccine compositions are formulated to protect the chimeric immunogen from acid and/or enzymatic degradation in the stomach. Upon passage to the neutral to alkaline environment of the duodenum, the chimeric immunogen then contacts a mucous membrane and is transported across the polarized epithelial membrane. The delivery constructs may be formulated in such compositions by any method known by one of skill in the art, without limitation.

In certain embodiments, the vaccine compositions are formulated for nasal administration. In certain embodiments, the vaccine compositions are formulated for rectal administration. In certain embodiments, the vaccine compositions are formulated for vaginal administration.

In certain embodiments, the oral formulation comprises a chimeric immunogen and one or more compounds that can protect the chimeric immunogen while it is in the stomach. For example, the protective compound should be able to prevent acid and/or enzymatic hydrolysis of the chimeric immunogen. In certain embodiments, the oral formulation comprises a chimeric immunogen and one or more compounds that can facilitate transit of the immunogen from the stomach to the small intestine. In certain embodiments, the one or more compounds that can protect the chimeric immunogen from degradation in the stomach can also facilitate transit of the immunogen from the stomach to the small intestine. Preferably, the oral formulation comprises one or more compounds that can protect the chimeric immunogen from degradation in the stomach and facilitate transit of the immunogen from the stomach to the small intestine. For example, inclusion of sodium bicarbonate can be useful in facilitating the rapid movement of intra-gastric delivered materials from the stomach to the duodenum as described in Mrsny et al., 1999, *Vaccine* 17:1425-1433.

Other methods for formulating compositions so that the chimeric immunogens can pass through the stomach and contact polarized epithelial membranes in the small intestine include, but are not limited to, enteric-coating technologies as described in DeYoung, 1989, *Int J Pancreatol.* 5 Suppl:31-6, and the methods provided in U.S. Pat. Nos. 6,613,332, 6,174,529, 6,086,918, 5,922,680, and 5,807,832.

Accordingly, in certain aspects, the invention provides a composition comprising a chimeric immunogen that comprises a receptor binding domain, a translocation domain, and a *C. trachomatis* antigen that has an amino acid sequence that is selected from the group consisting of AGTEAA (SEQ ID NO.:4), AGTDAA (SEQ ID NO.:5), AETIFDVTTLNPTIAGAGDVKTSAEG (SEQ ID NO.:6), AETILDVTTLNPTIAGKGTVVTSAE (SEQ ID NO.:7), TTLNPTIAGC (SEQ ID NO.:8), GAKPTATTGNATAPSTLTARE (SEQ ID NO.:9), TTSDVAGLQNDPC (SEQ ID NO.:10), SEFTINKPKGYVGKE (SEQ ID NO.:11), ILWEGFGGDPCDPCTT (SEQ ID NO.:12), ALNIWDRFDV (SEQ ID NO.:13), KMKSRKSCGIAVGTTVVSADKYAVT (SEQ ID NO.: 14), CAETIFDVTTLNPTIAGAGDVKTSAEGC (SEQ ID NO.: 15), CAETILDVTTLNPTIAGKGTVVTSAEC (SEQ ID NO.:16), CTTLNPTIAGC (SEQ ID NO.: 17), CGAKPTATTGNATAPSTLTAREC (SEQ ID NO.:18), and CTTSDVAGLQNDPC (SEQ ID NO.:19). In certain embodiments, the chimeric immunogen, when administered to a subject, induces an immune response in the subject that is effective to reduce adherence of a microorganism that expresses the *C. trachomatis* antigen to epithelial cells of the subject. In certain embodiments, the chimeric immunogen, when administered to a subject, induces an immune response in the subject that reduces cytotoxicity of *Pseudomonas* exotoxin A.

In certain embodiments, the composition further comprises a pharmaceutically acceptable diluent, excipient, vehicle, or carrier. In certain embodiments, the composition is formulated for nasal or oral administration.

6.8.2. Dosage and Regimen

Generally, a pharmaceutically effective amount of the vaccine compositions of the invention is administered to a subject. The skilled artisan can readily determine if the dosage of the vaccine composition is sufficient to elicit an immune response by monitoring the immune response so elicited, as described below. In certain embodiments, an amount of vaccine composition corresponding to between about 1 μg and about 1000 μg of chimeric immunogen is administered. In other embodiments, an amount of vaccine composition corresponding to between about 10 μg and about 500 μg of chimeric immunogen is administered. In still other embodiments, an amount of vaccine composition corresponding to between about 10 μg and about 250 μg of chimeric immunogen is administered. In yet other embodiments, an amount of vaccine composition corresponding to between about 10 μg and about 100 μg of chimeric immunogen is administered. Preferably, an amount of vaccine composition corresponding to between about 10 μg and about 50 μg of chimeric immunogen is administered. Further guidance on selecting an effective dose of the vaccine compositions may be found, for example, in Rose and Friedman, 1980, *Manual of Clinical Immunology*, American Society for Microbiology, Washington, D.C.

The volume of vaccine composition administered will generally depend on the concentration of chimeric immunogen and the formulation of the composition. In certain embodiments, a unit dose of the vaccine is between about 0.05 ml and about 1 ml, preferably about 0.5 ml. The vaccine compositions can be prepared in dosage forms containing between 1 and 50 doses (e.g., 0.5 ml to 25 ml), more usually between 1 and 10 doses (e.g., 0.5 ml to 5 ml)

The vaccine compositions of the invention can be administered in one dose or in multiple doses. A dose can be followed by one or more doses spaced by about 4 to about 8 weeks, by about 1 to about 3 months, or by about 1 to about 6 months. Additional booster doses can be administered as needed. In certain embodiments, booster doses are administered in about 1 to about 10 years.

6.8.3. Administration of Vaccine Compositions

The vaccine compositions of the invention can be administered to a subject by any method known to one of skill in the art. In certain embodiments, the vaccine compositions are contacted to a mucosal membrane of the subject. In other embodiments, the vaccine compositions are injected into the subject. By selecting one of these methods of administering the vaccine compositions, a skilled artisan can modulate the immune response that is elicited. These methods are described extensively below.

Thus, in certain embodiments, the vaccine compositions are contacted to a mucosal membrane of a subject. Any mucosal membrane known by one of skill in the art, without limitation, can be the target of such administration. For example, the mucosal membrane can be present in the eye, nose, mouth, lungs, esophagus, stomach, small intestine, large intestine, rectum, anus, vagina, or penis of the subject. Preferably, the mucosal membrane is a nasal mucous membrane.

In other embodiments, the vaccine composition is delivered by injection. The vaccine composition can be injected subcutaneously or intramuscularly. In such embodiments, the vaccine composition preferably comprises an adjuvant, as described above.

6.8.4. Kits Comprising Vaccine Compositions

In yet another aspect, the invention provides a kit comprising a vaccine composition of the invention. In certain embodiments, the kit further comprises instructions directing a medical professional to administer the vaccine composition to a subject to be vaccinated. In further embodiments, the instructions direct the medical professional to administer the vaccine composition of a mucous membrane of the subject to be vaccinated.

6.9. Antibodies Binding a *C. trachomatis* Antigen

The *C. trachomatis* antigens of the invention and the polynucleotides encoding them can also be used to prepare polyclonal or monoclonal antibodies that are capable of binding (preferably specifically) to at least one such *C. trachomatis* antigen. Thus, the present invention also provides monoclonal and polyclonal antibodies that bind a *C. trachomatis* antigen described herein.

In certain embodiments, the antibodies can recognize and bind isolated, modified, or multimeric *C. trachomatis* antigen(s). In certain embodiments, the antibodies can be obtained from mixtures of the antigens or fragments thereof. Certain of the antibodies of this invention may be specific to particular *C. trachomatis* classes or serovars, by binding to epitopes on the *C. trachomatis* MOMP which differ between *C. trachomatis* class or serovar. For example, an antibody of the invention may bind an epitope present on MOMP from *C. trachomatis* class B which is not present on MOMP from *C. trachomatis* class C or intermediate class, or vice versa. As a further example, an antibody of the invention may bind an epitope present on MOMP from *C. trachomatis* serovar A which is not present on MOMP from another *C. trachomatis* serovar, e.g., serovar B, C, D, etc., or which is present on MOMP from some other serovars but not others, or vice versa. In certain embodiments, the antibodies can bind an epitope present on MOMP from both *C. trachomatis* class B and class C. In certain embodiments, the antibodies can bind an epitope present on MOMP from both *C. trachomatis* class B and intermediate class. In certain embodiments, the antibodies can bind an epitope present on MOMP from both *C. trachomatis* intermediate class and class C.

The antibodies of the invention are useful, for example, in diagnosis of non-symptomatic chlamydial infection as well as symptomatic disease caused by *C. trachomatis* and in therapeutic compositions for treating humans and/or animals suspected of chlamydial infection or exhibit symptoms of such disease. The antibodies are useful in diagnosis alone or in combination with antibodies to other *C. trachomatis* antigens, as well as antibodies to other known antigens from homologous or completely heterologous species of microorganism. These antibodies are also useful in compositions that provide passive immune protection, which compositions may also be polyvalent, containing antibodies to antigens of other microorganisms or to more than one of the *C. trachomatis* antigens of this invention.

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In certain embodiments, the immunoglobulin molecules of the invention are IgG1. In other embodiments, the immunoglobulin molecules of the invention are IgG4.

In certain embodiments, the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, horse, sheep, rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described, for example in, U.S. Pat. No. 5,939,598

The antibodies may be monospecific, bispecific, trispecific or of greater multispecificity. Multispecific antibodies may be specific for different epitopes of a polypeptide of the present invention or may be specific for both a *C. trachomatis* antigen of the present invention as well as for a heterologous epitope, such as a heterologous polypeptide or solid support material. See, e.g., International Patent Publication Nos. WO 93/17715, WO 92/08802, WO 91/00360, and WO 92/05793; Tutt et al., 1991, *J. Immunol.* 147:60; Kostelny et al., 1992, *J. Immunol.* 148:1547; and U.S. Pat. Nos. 4,474,893, 4,714,681, 4,925,648, 5,573,920, and 5,601,819.

The antibodies of the present invention may be described or specified in terms of the epitope(s) or *C. trachomatis* antigen(s) which they recognize or specifically bind. The epitope(s) or *C. trachomatis* antigen(s) may be specified as described herein, e.g., by N-terminal and C-terminal positions, by size in contiguous amino acid residues, or as listed in the Examples and Figures. Antibodies which specifically bind any epitope or polypeptide of the present invention may also be excluded. Therefore, the present invention includes antibodies that specifically bind polypeptides of the present invention, and allows for the exclusion of the same.

The antibodies can be generated by conventional means utilizing, for example, the isolated, recombinant or modified *C. trachomatis* antigens of this invention, mixtures of such antigens or antigenic fragments, whether alone, as part of a chimeric immunogen, or as part of an immunogenic composition as described herein. For example, polyclonal antibodies can be generated by conventionally stimulating the immune system of a selected animal or human with the isolated antigen or mixture of antigenic proteins or peptides of this invention, allowing the immune system to produce natural antibodies thereto, and collecting these antibodies from the animal or human's blood or other biological fluid.

For example, an antibody according to the invention can be produced by administering to a vertebrate host an antigen, immunogenic composition, or chimeric immunogen of this invention. Preferably, a chimeric immunogen comprising a C, trachomatis antigen is used as an immunogen. A suitable polyclonal antibody against the *C. trachomatis* antigen may be generated as antisera.

In certain embodiments, an antibody of the invention can be isolated by affinity purifying antiserum generated during an infection of a mammal, e.g., a mouse, with *C. trachomatis* using as immunoabsorbant a *C. trachomatis* antigen described herein. In certain embodiments, an antibody of the invention can be isolated by immunizing mice with a antigen of this invention, whether alone or as part of a chimeric immunogen or immunogenic composition, or a purified, isolated *C. trachomatis* antigen of native origin.

Monoclonal antibodies (MAbs) against a *C. trachomatis* antigen are also contemplated as part of this invention. Hybridoma cell lines expressing desirable MAbs that recognize a *C. trachomatis* antigen can be generated by well-known conventional techniques. See, e.g., Harlow and Lane, 1989, *Antibodies: A Laboratory Manual*, Cold Spring Harbor Press, NY. Similarly, desirable high titer antibodies can be generated by applying recombinant techniques to the monoclonal or polyclonal antibodies developed against a *C. trachomatis* antigen. See, e.g., International Patent Application No. PCT/GB85/00392; British Patent Application Publication No. GB2188638A; Amit et al., 1986, *Science* 233:747; Queen et al., 1989, *Proc. Nat'l. Acad. Sci. USA*, 86:10029-10033; International Patent Publication No. WO90/07861; Riechmann et al., 1988, *Nature* 332:323; and Huse et al., 1988, *Science* 246:1275.

Further, one of skill in the art may generate chimeric, humanized or fully human antibodies directed against a *C. trachomatis* antigen or antigenic fragments thereof by manipulating the complementarity determining regions of animal or human antibodies to the antigen of this invention. See, e.g., Mark and Padlin, "Humanization of Monoclonal Antibodies," Chapter 4, *The Handbook of Experimental Pharmacology*, Vol. 113, The Pharmacology of Monoclonal Antibodies, Springer-Verlag (June, 1994).

Alternatively, the antigens can be assembled as multi-antigenic complexes (see, e.g., European Patent Application 0339695) or as simple mixtures of antigenic proteins/peptides and employed to elicit high titer antibodies capable of binding the selected antigen(s) as it appears in the biological fluids of an infected animal or human.

Further provided by the present invention are anti-idiotype antibodies (Ab2) and anti-anti-idiotype antibodies (Ab3). Ab2 are specific for the target to which anti-*C. trachomatis* antibodies of the invention bind and Ab3 are similar to *C. trachomatis* antibodies (Ab1) in their binding specificities and biological activities. See, e.g., Wettendorff et al., 1990, "Modulation of anti-tumor immunity by anti-idiotypic antibodies" in *Idiotypic Network and Diseases*, Cerny and Hiernaux, eds., Am. Soc. Microbiol., Washington D.C.: pp. 203-229. These anti-idiotype and anti-anti-idiotype antibodies can be produced using techniques well known to those of skill in the art. Such anti-idiotype antibodies (Ab2) can bear the internal image of a *C. trachomatis* antigen, or fragment thereof, and are thus useful for the same purposes as the *C. trachomatis* antigens.

In general, polyclonal antisera, monoclonal antibodies and other antibodies which bind to a *C. trachomatis* antigen (Ab1) are useful to identify epitopes of *C. trachomatis* MOMP, to separate *C. trachomatis* MOMP and analogs thereof from contaminants (e.g., in chromatographic columns and the like), and in general as research tools and as starting material for the development of other types of antibodies described above. Anti-idiotype antibodies (Ab2) are useful for binding the same Ab1 antibodies for, e.g. purification, and may also be used in place of the a *C. trachomatis* antigen to induce an immune response.

When convenient for use in diagnostic assays, the antibodies can be associated with conventional labels which are capable, either alone or in concert with other compositions or compounds, of providing a detectable signal. Where more than one antibody is employed in a diagnostic method, the labels can be desirably interactive to produce a detectable signal. Alternatively, in such embodiments, the labels can be independently detectable, where preferably the signal from one antibody or antibody composition does not interfere with detection of the signal from the other antibody or antibody composition. In certain embodiments, the label can be detectable visually, e.g., calorimetrically. A variety of suitable enzyme systems have been described in the art which can reveal a calorimetric signal in an assay. For example, glucose oxidase (which uses glucose as a substrate) releases peroxide as a product. Peroxidase, when reacted with peroxide and a hydrogen donor such as tetramethyl benzidine (TMB), can produce an oxidized TMB that can be detected as a blue color. Other examples of suitable calorimetric systems include horseradish peroxidase (HRP) or alkaline phosphatase (AP), and hexokinase in conjunction with glucose-6-phosphate dehydrogenase which reacts with ATP, glucose, and $NAD^+$ to yield, among other products, NADH that can be detected as increased absorbance at 340 nm wavelength. Other label systems that may be utilized in the methods of this invention are detectable by other means, such as, e.g., colored latex microparticles (Bangs Laboratories, Indiana) in which a dye is embedded may be used in place of enzymes to form conjugates with the antibodies and provide a visual signal indicative of the presence of the resulting complex in applicable assays. Still other labels include fluorescent compounds, radioactive compounds, or radioactive elements. Detectable labels for attachment to antibodies useful in diagnostic assays can be easily selected from among numerous compositions known and readily available to one skilled in the art. The methods and antibodies of this invention are not limited by the particular detectable label or label system employed.

6.10. Making and Testing the Chimeric Immunogens

The chimeric immunogens of the invention are preferably produced recombinantly, as described below. However, the chimeric immunogens may also be produced by chemical synthesis using methods known to those of skill in the art. Alternatively, the chimeric immunogens can be produced using a combination of recombinant and synthetic methods.

6.10.1. Manufacture of Chimeric Immunogens

Methods for expressing and purifying the chimeric immunogens of the invention are described extensively in the examples below. Generally, the methods comprise introducing an expression vector encoding the chimeric immunogen into a cell that can express the chimeric immunogen from the vector. The chimeric immunogen can then be purified for administration to a subject following expression of the immunogen.

6.10.2. Verification of Chimeric Immunogens

Having selected the domains of the chimeric immunogen, the function of these domains, and of the chimeric immunogens as a whole, can routinely be tested to ensure that the immunogens can induce the desired immune response. For example, the chimeric immunogens can be tested for cell recognition, cytosolic translocation and immunogenicity using routine assays. The entire chimeric protein can be tested, or, the function of various domains can be tested by substituting them for native domains of the wild-type toxin.

6.10.2.1. Receptor Binding/Cell Recognition

Receptor binding domain function can be tested by monitoring the chimeric immunogen's ability to bind to the target receptor. Such testing can be accomplished using cell-based assays, with the target receptor present on a cell surface, or in cell-free assays. For example, chimeric immunogen binding to a target can be assessed with affinity chromatography. The chimera can be attached to a matrix in an affinity column, and binding of the receptor to the matrix detected, or vice versa. Alternatively, if antibodies have been identified that bind to either the receptor binding domain or its cognate receptor, the antibodies can be used, for example, to detect the receptor binding domain in the chimeric immunogen by immunoassay, or in a competition assay for the cognate receptor. An exemplary cell-based assay that detects chimeric immunogen binding to receptors on cells comprises labeling the chimera and detecting its binding to cells by, e.g., fluorescent cell sorting, autoradiography, etc.

6.10.2.2. Translocation

The function of the translocation domain can be tested as a function of the chimeric immunogen's ability to gain access to the interior of a cell. Because access first requires binding to the cell, these assays can also be used to assess the function of the cell recognition domain.

The chimeric immunogen's ability to enter the cell can be assessed, for example, by detecting the physical presence of the chimera in the interior of the cell. For example, the chimeric immunogen can be labeled with, for example, a fluorescent marker, and the chimeric immunogen exposed to the cell. Then, the cells can be washed, removing any chimeric immunogen that has not entered the cell, and the amount of label remaining determined. Detecting the label in this fraction indicates that the chimeric immunogen has entered the cell.

6.10.2.3. ER Retention and Translocation to the Cytosol

A related assay can be used to assess the ability of the chimeric immunogen to traffic to the ER and from there into the cytosol of a cell. In such assays, the chimeric immunogen can be labeled with, for example, a fluorescent marker, and the chimeric immunogen exposed to the cell. The cells can then be washed and treated to liberate the cellular contents. The cytosolic fraction of this preparation can then be isolated and assayed for the presence of the label. Detecting the label in this fraction indicates that the chimeric immunogen has entered the cytosol.

In another method, the ability of the translocation domain and ER retention domain to effect translocation to the ER and to the cytosol can be tested with a construct containing a domain III having ADP ribosylation activity. Briefly, cells expressing a receptor to which the construct binds are seeded in tissue culture plates and exposed to the chimeric protein or to an engineered PE exotoxin containing the modified translocation domain or ER retention sequence in place of the native domains. ADP ribosylation activity can be determined as a function of inhibition of protein synthesis by, e.g., monitoring the incorporation of 3H-leucine.

6.10.2.4. Immunogenicity

The ability of the chimeric immunogens to elicit an immune response against the heterologous antigen can be assessed by determining the chimeric immunogen's immunogenicity. Both humoral and cell-mediated immunogenicity can be assessed. For example, a humoral immune response can tested by inoculating an animal with the chimeric immunogen and detecting the production of antibodies specific for the heterologous immunogen with a suitable immunoassay. Such detection is well within the ordinary skill of those in the art.

In addition, cell-mediated immunogenicity can be tested by immunizing an animal with the chimeric immunogen, isolating cytotoxic T cells from the animal, and detecting their ability to kill cells whose MHC Class I molecules bear peptides sharing amino acid sequences with the heterologous antigen. This assay can also be used to test the activity of the cell recognition domain, the translocation domain and the ER retention domain because generation of a cell mediated response requires binding of the chimera to the cell, trafficking to the ER, and translocation to the cytosol.

7. EXAMPLES

The following examples merely illustrate the invention, and are not intended to limit the invention in any way.

7.1. Construction of Chimeric Immunogen Expression Vectors

Expression vectors that express ten different chimeric immunogens, shown below in Table 1, were generated in a multistep process. The individual chimeric immunogens were constructed to contain one, two, or three *C. trachomatis* antigens, as shown in Table 1. The sequences of the different *C. trachomatis* antigens are shown in Table 2, below.

TABLE 1

| Immunogen | *C. trachomatis* antigen | Antibody Recognition |
|---|---|---|
| (1) | E | M40-1, L21-10 |
| (2) | F | M40-1, L21-10 |
| (3) | C and E | M40-1, L21-10 |
| (4) | D and E | M40-1, L21-10 |
| (5) | C, D, and E | M40-1, L21-10 |
| (6) | G | M40-1, L21-10 |
| (7) | A and C | M40-1, L21-10 |
| (8) | A and D | M40-1, L21-10 |
| (9) | A | M40-1, |
| (10) | B | M40-1, |

TABLE 2

| Designation | Amino Acid Sequence | SEQ ID | MOMP Domain |
|---|---|---|---|
| A | $C^{63}$GAKPTATTGNATAPSTLTAR$^{83}$EC | SEQ ID NO.: 4 | VS1 |
| B | $C^{69}$TTSDVAGLQNPP$^{77}$C | SEQ ID NO.: 5 | VS1 |
| C | $^{231}$AGTEA$^{236}$A | SEQ ID NO.: 6 | VS3 |
| D | $^{231}$AGTDA$^{236}$A | SEQ ID NO.: 7 | VS3 |
| E | $C^{289}$AETIFDVTTLNPTIAGAGDVKTSAE$^{314}$GC | SEQ ID NO.: 8 | VS4 |
| F | $C^{293}$AETILDVTTLNPTIAGKGTVVTSAE$^{309}$C | SEQ ID NO.: 9 | VS4 |
| G | $C^{298}$TTLNPTIAG$^{306}$C | SEQ ID NO.: 10 | VS1 |

All antigens described above were selected from the MOMP from *C. trachomatis* serovar A (Accession No.: S12799; Hayes et al., 1990, *J. Gen. Microbiol.* 136(Pt 8):1559).

To generate the ten chimeric immunogens, oligonucleotide duplexes encoding the *C. trachomatis* antigens were purchased from Biosource (Camarillo, Calif.) and ligated into the unique PstI site of both pPE64 and pPE64pSTΔ553, thereby generating vectors for expressing both toxic and nontoxic forms of the ten chimeric immunogens. See Hertle et al., 2001, *Infect. Immun.* 69(15): 6962-6969. The plasmids were sequenced to ensure correct orientation of the inserts and to make sure that the plasmid had not been corrupted.

7.2. Expression of Chimeric Immunogens

*E. coli* DH5α cells (Gibco/BRL) were transformed using a standard heat-shock method with the appropriate plasmid to express toxic and nontoxic forms of the ten chimeric immunogens. Transformed cells, selected on antibiotic-containing media, were isolated and grown in Luria-Bertani broth (Difco; Becton Dickinson, Franklin Lakes, N.J.) with antibiotic and induced for protein expression by the addition of 1 mM isopropyl-D-thiogalactopyranoside (IPTG). Two hours following IPTG induction, cells were harvested by centrifugation at 5000 rpm. Inclusion bodies were isolated following cell lysis and proteins were solubilized in 6M guanidine HCl and 2 mM EDTA (pH 8.0) plus 65 mM dithioerythreitol. Following refolding and purification, as previously described (Buchner et al., 1992, *Anal. Biochem.* 205:263-70; Hertle et al., 2001, *Infect. Immun.* 69(15): 6962-6969), proteins were stored in PBS (pH 7.4) lacking $Ca^{2+}$ and $Mg^{2+}$ at −80° C.

7.3. Characterization of a Chimeric Immunogen

The chimeric immunogens 1 and 2 were characterized by preparing toxic forms of the chimeric immunogens, as described above, and testing them on a toxin-sensitive cell line as previously described. See Hertle et al., 2001, *Infect. Immun.* 69(15): 6962-6969, FitzGerald et al., 1998, *J Biol Chem* 273:9951-8, and Ogata et al., 1990, *J. Biol. Chem.* 265:20678-85. The toxic forms of chimeric immunogens 1 and 2, comprising *C. trachomatis* antigens 4a or 4b, respectively, retained the ability to kill L929 (ATCC CCL-1) cells, demonstrating that the toxic chimeric immunogens 1 and 2 bind CD91 and are properly trafficked inside the cell following internalization. See FIG. 1. Nontoxic chimeric immunogen 1 expressed and folded under the same conditions showed no toxicity, while nontoxic chimeric 2 displayed approximately 25% toxicity relative to PE. See FIG. 1.

Additionally, SDS-PAGE and Western blots were performed to verify the correct molecular weight and antigenic determinants of chimeric immunogens 1 and 2. FIG. 2*a* shows a Western blot of chimeric immunogens 1 and 2 probed with a chlamydia-specific monoclonal antibody, L21-10 (see Baehr et al., 1988; *Proc. Nat. Acad. Sci. USA* 85:4000, which is specific for a portion of VS4 of all known serovars of *C. trachomatis*. A portion of this sequence was included in chimeric immunogens 1 and 2. The blots were also probed with monoclonal antibody M40-1 (See Ogata, 1991, *Infect. Immun* 59:407-414), specific for the ntPE vector (FIG. 2*b*). Taken together, the above-described analysis of these chimeras demonstrated that these antigens can be successfully integrated in a native or near-native conformation into correctly-folded chimeric immunogens.

7.4. Vaccination Using a Chimeric Immunogen

Six to eight female C3H/HeJ mice were immunized intranasally (IN), 50 µl in each nostril, using a preparation of purified chimeric immunogen 1 with 0.015% carboxymethylcellulose in PBS (Group B); the carboxymethylcellulose was used to facilitate an increase time of presence in the nasal mucosa prior to natural washout by mucosal secretions. 8 additional female C3H/HeJ mice were immunized intranasally with ntPE in 0.015% carboxymethylcellulose in PBS as negative control (Group A), and 6 additional female C3H/HeJ mice were also immunized subcutaneously with chimeric immunogen 1 with either Freund's complete or incomplete adjuvant (Group C) to determine the level of systemic antibodies raised to this chimeric immunogen. The mice were administered the chimeric immunogen for a total of six administrations at 0 weeks 2 weeks, 4 weeks, 6 weeks, 10 weeks, 14 weeks, and 16 weeks, and the immune responses of the mice were monitored over time. Mice were challenged with *Chlamydia* infection at week 20.

7.5. Isolation of Secreted Antibodies

Mouse saliva (typically 50-100 μl) was collected over a 10 minute period using a polypropylene Pasteur pipette following the induction of hyper-salivation by an intra-peritoneal injection of 0.1 mg pilocarpine per animal. Serum samples (100 μl) were obtained using serum separators with blood collected from either periorbital or tail bleeds. Serum and saliva samples were then aliquoted in 10 μl volumes and stored at −70° C. until analysis. Secreted antibodies thus obtained were characterized in the assays described below.

7.6. ELISA Assays

A standard 96 well ELISA format protocol was developed using the chimeric immunogen 1 or chlamydial elementary bodies (EBs) as the protein against which the mouse sera was reacted. The serum dilutions were 1:200 for Group A, 1:60,000 for Group B, and 1:200,000 for Group C using the chimeric immunogen and 1:100 for each group when reacting against chlamydial EBs. An ntPE protein without the *C. trachomatis* antigen was used as a negative control in the ELISA assays. A standard curve was determined by reacting the L21-10 MAb, which is specific for *C. trachomatis*, against serial dilutions of chimeric immunogen 1.

By comparison with the control and chimeric immunogen 1 IN immunized groups, systemic levels of IgG were similar in the IN (Group B) and SC (Group C) immunized groups while the control IN (Group A) immunized group had extremely low levels of IgG. See FIG. 3A. There was a statistically significant difference between the SC and IN immunized group compared with the control IN immunized group ($p<0.001$). The first panel and second panel of FIG. 3A show the same results for Group A, with the scale changed for the first panel, which reveals an immune response to *C. trachomatis* as expected following challenge with chlamydial infection at 20 weeks.

The high level of specificity observed for Groups B and C was achieved by the third vaccination, which occurred 4 and 2 weeks from the first and second immunizations, respectively. Three subsequent boosts produced no significant increase in antibody response by either IN or SC routes compared with the third vaccination. Substantial differences were observed in the ELISA assays from Groups B and C using chimeric immunogen 1 and ntPE, showing that the immune response induced by chimeric immunogen 1 is specific for the *C. trachomatis* antigen. See FIG. 3A. The IgG response observed in ELISA assays against *C. trachomatis* EBs was consistent with the results observed in the ELISA assays against chimeric immunogen 1. See FIG. 3B. In particular, an immune response against *C. trachomatis* antigens was observed in Group A only following challenge with chlamydial infection, while IgG obtained from Groups B and C was specific for *C. trachomatis* EBs.

Moreover, the IgA response in saliva was significantly higher in the IN immunized mice than in the IN control-immunized mice (Group A) or SC-immunized mice (Group C) as measured in ELISAs against both chimeric immunogen 1 (FIG. 4A) and *C. trachomatis* EBs (FIG. 4B). While some nonspecific increase in the IgA response to EBs was observed with Group A following the sixth immunization (FIG. 4B), chimeric immunogen 1 elicited a higher IgA level and improved protective capabilities following immunization as compared to Groups A and C, as discussed below.

7.7. *C. trachomatis* Attachment Assays

Having demonstrated that chimeric immunogen 1 elicited mucosal (salivary IgA) and systemic (IgG) immune responses, the potential for antibodies present in saliva obtained from immunized mice to block attachment of *C. trachomatis* to a human epithelial cell line was investigated in an attachment assay.

A549 (human lung epithelial-like carcinoma cells; ATCC CCL-185) cells were maintained in Ham's F-12 medium (Ham's F12) supplemented with 10% heat-inactivated fetal bovine serum (HI-FBS), 2.5 mM glutamine, 100 U/ml penicillin, and 100 μg/ml streptomycin in 5% $CO_2$ at 37° C. Cells were transferred to antibiotic-free Ham's F-12 medium to seed in chamber slides for assays.

*C. trachomatis* elementary bodies (EBs) were cultured and purified as previously described for use in the attachment assays. See Caldwell et al., 1981, *Infect. Immun.* 31:1161-76.

*C. trachomatis* adherence to A549 cells was quantified as follows. A549 cells were grown in Lab-Tek II 8-chamber slides (Lab-Tek, USA) in antibiotic-free medium to a density of approximately $1\times10^5$ cells per chamber using culture conditions described in Ogata et al., 1990, *J. Biol. Chem.* 265:20678-85. Spent media was removed before adding bacteria opsonized with test samples. Chamber slides were incubated for 2 h at 37° C. and 5% $CO_2$.

Cells were gently washed three times with Hanks' balanced salt solution to remove unbound bacteria, fixed for 1 h in 3.7% paraformaldehyde in phosphate buffered saline (PBS), pH 7.2, washed twice with saline and stained with 10% Giemsa stain for 10 min. After washing to remove excess Giemsa stain, adherent bacteria were determined by counting cell-associated bacteria per 50 A549 cells under light microscopy at 1000× magnification. All samples were tested in duplicate.

Saliva samples collected from mice immunized IN with chimeric immunogen 1 (Group B) and diluted 1:100 in PBS were able to significantly decrease *C. trachomatis* adherence to A549 cells at 72 hours of incubation. See FIG. 5. Saliva from mice immunized with ntPE lacking the *C. trachomatis* antigen (Group A), however, also showed a substantial reduction in *C. trachomatis* binding, suggesting that mucosal immunization with chimeric immunogen 1 may act to reduce *C. trachomatis*-epithelium interactions, but that this effect may be nonspecific.

7.8. Isolation of Clonal *C. trachomatis* Strains

Clonally purified isolates are important for challenge experiments to test the ability of the chimeric immunogens to elicit immune responses broadly protective against multiple serovars. Clonal populations of serovars Ba, E, G, K and L2 were isolated for these studies. To do so, HeLa229 cells were plated at a density of $1.5 \times 10^6$ in six-well plates and incubated ON at 37° C. in 5% $CO_2$ prior to inoculation with a strain in SPG (0.25 M sucrose, 10 mM sodium phosphate, 5 mM L-glutamic acid, pH 7.4) at a multiplicity of infection (MOI) of 1 using culture techniques as previously described. See Dean and Powers, 2001, *Infect Immun* 69:2442-7. The inoculum was serially diluted so that each well in the plate had $1/10^{th}$ the inocula of the previous well to ensure that the dilute wells would have the fewest IFUs and form a single infected cell that would produce a plaque. Monolayers were infected by incubation at room temperature (RT), and then incubated in minimal essential media (MEM) containing 1 μg/ml cycloheximide and 10% Fetal Bovine Serum (FBS) as above. The plaque assay performed according to the method of Matsumoto et al., 1998, *J Clin Microbiol* 36:3013-9, with modifications as described hereinafter. Melted agarose [1.1% SeaKem ME agarose (RMC BioProducts) in $ddH_2O$] was mixed with 2×MEM and FCS (10% final concentration) and 1 μg/ml of cycloheximide and overlaid on each well. Two ml of 1×MEM with 10% FCS without cycloheximide were added and incubated as above. The final agarose medium (1/100 volume of neutral red, no cycloheximide) was added to the first agarose on one plate for days 9 to 14 postinoculation (pi).

Representative results of the isolations are shown in FIG. 6. FIG. 6 shows a single plaque where most cells are stained red (neutral red stains cytoplasm of viable cells) at the periphery of the plaque; cells in the center have little or no stain (FIG. 6*a*) because inclusions displace cellular contents to the edge of the cell (FIG. 6*b*). Ten single plaques of about 0.8 mm were selected, sonicated, and applied to six-well plates with monolayers and grown as above. After three plaque purifications, half the isolate was grown up and half was used for EB purification by renograffin gradient as previously described. See Caldwell et al., 1981, *Infect. Immun.* 31:1161-76. DNA was extracted, amplified by PCR, and sequenced for ompA as described previously. See Dean and Millman, 1997, *J. Clin. Invest.* 99:475-83; Baehr et al., 1988, *Proc. Natl. Acad. Sci. USA* 85:4000-4004; and Hayes et al., 1995, *J. Infect. Dis.* 172:268-272.

After MASE alignment, three of the 10 serovar Ba plaques differed by a single nucleotide change, representing a mixed clonal population of isolates. See Millman et al., 2001, *J Bacteriol* 183:5997-6008. In contrast, all 10 plaques of E, G, K and L2 were identical.

7.9. Protective Immune Responses Induced by Chimeric Immunogen 1

Once animals immunized with a chimeric immunogen demonstrated a robust immune response as described above, they were challenged with varying concentrations of two serovars of *C. trachomatis*. The serovars represented those that were plaque purified so that only a single clonal population would be inoculated into the mouse. The two serovars were selected because these pathogenic serovars are well documented for infecting mice (E and K).

Initially, a single serovar was used to vaginally challenge unimmunized mice to assess the distribution of chlamydial infection in the genital tract. A total volume of either 100 μl or 50 μl containing $10^8$ IFUs was used for intravaginal challenge as previously described. See Ito et al., 1990, *Infect. Immun.* 58:2021-2023. At one week after challenge, the mice were sacrificed and one half of each organ in the genital tract (vagina, uterus, horn, and ovaries) was snap frozen in OCT while the other half was subjected to RNA extraction, reverse transcription, and quantitative (k)PCR to quantitate the relative amounts of chlamydial RNA in each organ. These data were then normalized against mouse GAPDH for the respective organ. FIG. 7 shows the results of these experiments, indicating that a higher relative amount of chlamydial RNA was observed in the uterus compared to the horn and vagina. No chlamydial RNA was observed in the ovaries.

In addition, the other half of each organ that had been frozen in OCT was sectioned to detect *C. trachomatis* by immunohistochemistry (IHC). Briefly, sections were cut to 5 microns thickness and placed on slides, air dried, and fixed with acetone. The slides were then blocked for endogenous peroxide and biotin, then caesin (Biocare Medical) was used to block protein staining prior to staining with a *C. trachomatis* MOMP polyclonal antibody (Virostat). The slide was then reacted with streptavidin, and AEC was used as chromogen to stain *C. trachomatis* red. The IHC results correlated well with the kPCR results from the respective organ.

Subsequently, a single serovar was used for vaginally challenging mice from each of Groups A, B, and C, described above. A total volume of 100 μl containing $10^8$ IFUs was used for intravaginal challenge as previously described. See Ito et al., 1990, *Infect. Immun.* 58:2021-2023. Following inoculation, the mice were vaginally sampled at 72 hours and then weekly for 5 weeks to determine the extent of recovery of live chlamydiae from the mice. A male calcium alginate swab was used to sample the vagina of anesthetized mice, and was placed in chlamydiae collection media for subsequent analyses. One half of the sample was used for RNA extraction, to generate cDNA for quantitative real time(k)PCR as described above. The second half of the collected material was used standard tissue culture to determine the IFUs in HeLa cells. In order to ensure that technicians were blinded, each mouse was randomly coded during collection of vaginal samples so that the data could not be linked back to the immunization group until the data were analyzed.

After seven days, the challenged mice were sacrificed and IHC was used to quantify differences between *C. trachomatis* infection in the uterus and horns of Groups A and B. *C. trachomatis* infection was observed in all of the Group A mice, primarily in endometrial tissue. See FIGS. 8*a* and 8*b*. No *C. trachomatis* infection was observed in either the uterus or horn of any mouse of Group B except for residual protein stained in the lumen of the uterus. See FIG. 8*c*. Thus, intranasal administration of chimeric immunogen 1 elicited a protective immune response to genital *C. trachomatis* infection.

To confirm the IHC results described above, quantitative (k)PCR was performed as described above to detect the amounts of *C. trachomatis* mRNA in the respective groups. As shown in FIG. 9, 5 of 6 mice in Group A exhibited high levels of chlamydial RNA, while only 2 of 8 mice in Group B exhibited appreciable mRNA levels.

Finally, sections from the uterus of mice from Groups A and B were hemolysin and eosin stained to assess neutrophilic and lymphocytic infiltration of the uterus following vaginal challenge with *C. trachomatis*. See FIG. 10. Such neutrophilic and lymphocytic infiltration was observed for mice immunized with chimeric immunogen 1 (Group B; see FIG. 10B) but not ntPE (Group A; see FIG. 10A). Thus, the immune response induced by chimeric immunogen 1 was consistent with a T-cell-mediated antigenic response driven by previous immunization.

The present invention provides, inter alia, chimeric immunogens and methods of inducing an immune response in a subject. While many specific examples have been provided, the above description is intended to illustrate rather than limit the invention. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. Citation of these documents is not an admission that any particular reference is "prior art" to this invention.

What is claimed is:

1. A chimeric immunogen, comprising
   a) a *Pseudomonas exotoxin* A (PE) receptor binding domain Ia
   b) a PE translocation domain II,
   c) a *Chlamydia trachomatis* antigen selected from the group consisting of AETIFDVTTLNPTIAGAGDVKT-SAEG (SEQ ID NO.:6), AETILDVTTLNPTI-AGKGTVVTSAE (SEQ ID NO.:7), TTLNPTIAGC (SEQ ID NO.:8), CAETIFDVTTLNPTIAGAGDVKT-SAEGC (SEQ ID NO.: 15), CAETILDVTTLNPTI-AGKGTVVTSAEC (SEQ ID NO.:16), and CTTLNP-TIAGC (SEQ ID NO.:17) inserted into PE domain Ib, and
   d) a PE endoplasmic reticulum retention domain III, wherein the PE domain Ib is located between PE translocation domain II and PE endoplasmic reticulum retention domain III wherein the said chimeric immunogen does not comprise more than one *C. trachomatis* antigen.

2. The chimeric immunogen of claim 1, wherein said *C. trachomatis* antigen replaces all or a portion of said PE domain Ib.

3. The chimeric immunogen of claim 1, wherein said PE endoplasmic reticulum retention domain III is an enzymatically inactive PE domain III.

4. The chimeric immunogen of claim 3, wherein said enzymatically inactive PE domain III is inactivated by deleting a glutamate at position 553.

5. The chimeric immunogen of claim 1, wherein said PE endoplasmic reticulum retention domain III comprises an amino acid sequence that is selected from the group of RDEL (SEQ ID NO.:20) or KDEL (SEQ ID NO.:21).

6. The chimeric immunogen of claim 1, wherein said translocation domain comprises amino acids 280 to 364 of domain II of *Pseudomonas exotoxin* A.

7. A composition comprising the chimeric immunogen of claim 1.

8. The composition of claim 7, wherein said composition further comprises a pharmaceutically acceptable diluent, excipient, vehicle, or carrier.

9. A kit, comprising an article of manufacture containing the composition claim 7.

* * * * *

UNITED STATES PATENT AND TRADEMARK OFFICE
CERTIFICATE OF CORRECTION

| | | |
|---|---|---|
| PATENT NO. | : 7,964,200 B2 | Page 1 of 1 |
| APPLICATION NO. | : 11/914734 | |
| DATED | : June 21, 2011 | |
| INVENTOR(S) | : Randall J. Mrsny | |

It is certified that error appears in the above-identified patent and that said Letters Patent is hereby corrected as shown below:

Please add the Statement Regarding Federally Sponsored Research beginning on column 1, line 11, with the following statement:

STATEMENT REGARDING FEDERALLY SPONSORED RESEARCH

--This invention was made with government support under grants entitled "Pathogenesis of persistent C. trachomatis STDs," SBIR Grant No. R01AI39499, and "Mucosal vaccine for Chlamydia trachomatis infection," SBIR Grant No. 5R43AI052500-02, which was awarded by the National Institute of Health, United States Department of Health and Human Services. The U.S. government has certain rights in this invention.--

Signed and Sealed this
Eleventh Day of October, 2011

David J. Kappos
*Director of the United States Patent and Trademark Office*

```
                        SEQUENCE LISTING

<160> NUMBER OF SEQ ID NOS: 98

<210> SEQ ID NO 1
<211> LENGTH: 27
<212> TYPE: PRT
<213> ORGANISM: Artificial Sequence
<220> FEATURE:
<223> OTHER INFORMATION: Formula IV for construct C. trachomatis
      antigen
<220> FEATURE:
<221> NAME/KEY: VARIANT
<222> LOCATION: 1, 2, 3, 4, 5, 7, 12, 14, 15
<223> OTHER INFORMATION: Xaa1=A or V; Xaa2=E, T, or K; Xaa3=A, T, or P;
      Xaa4=I or V; Xaa5=F, L, or V; Xaa7=V, T, or I;
      Xaa12=P or R; Xaa14=T or I; Xaa15=A or T
<220> FEATURE:
<221> NAME/KEY: VARIANT
<222> LOCATION: 17, 19, 21, 22, 23, 24
<223> OTHER INFORMATION: Xaa17=A, C, or K; Xaa19=S, G, T, A, E, or D;
      Xaa21=A, V, I, or K; Xaa22=A, G, S, or T;
      Xaa23=A, G, N, or S; Xaa24=G, N, or absent
<220> FEATURE:
<221> NAME/KEY: VARIANT
<222> LOCATION: 25, 26, 27
<223> OTHER INFORMATION: Xaa25=A, S, or T; Xaa26=D or E; and Xaa27=G or
      N

<400> SEQUENCE: 1

Xaa Xaa Xaa Xaa Xaa Asp Xaa Thr Thr Leu Asn Xaa Thr Xaa Xaa Gly
 1               5                  10                  15

Xaa Gly Xaa Val Xaa Xaa Xaa Xaa Xaa Xaa Xaa
            20                  25

<210> SEQ ID NO 2
<211> LENGTH: 6
<212> TYPE: PRT
<213> ORGANISM: Artificial Sequence
<220> FEATURE:
<223> OTHER INFORMATION: Formula II for construct C. trachomatis
      antigen
<220> FEATURE:
<221> NAME/KEY: VARIANT
<222> LOCATION: 1, 4, 5, 6,
<223> OTHER INFORMATION: Xaa1=A, S; Xaa4=D or E, Xaa5=A or G; Xaa6=A
      or V

<400> SEQUENCE: 2

Xaa Gly Thr Xaa Xaa Xaa
 1               5

<210> SEQ ID NO 3
<211> LENGTH: 23
<212> TYPE: PRT
<213> ORGANISM: Artificial Sequence
<220> FEATURE:
<223> OTHER INFORMATION: Formula III for construct C. trachomatis
      antigen
<220> FEATURE:
<221> NAME/KEY: VARIANT
<222> LOCATION: 2, 3, 4, 5, 6, 7, 8, 9
<223> OTHER INFORMATION: Xaa2=A, D, or E; Xaa3=A, E, or K; Xaa4=L or P;
      Xaa5=A or T; Xaa6=A, G, S, T, or V; Xaa7=K, N, R, S, or absent;
      Xaa8=A, D, or absent; Xaa9=A, D, I, S, T, or V
```

```
<220> FEATURE:
<221> NAME/KEY: VARIANT
<222> LOCATION: 10, 11, 12, 13, 14, 15
<223> OTHER INFORMATION: Xaa10=A, E, G, T, or V; Xaa11=D, G, or N;
      Xaa12=L, N, or T; Xaa13=A, E, Q, S, or T;
      Xaa14=A, K, N, S, or T; Xaa15=A, D, or T
<220> FEATURE:
<221> NAME/KEY: VARIANT
<222> LOCATION: 16, 17, 18, 19, 20, 21, 23
<223> OTHER INFORMATION: Xaa16=L or P; Xaa17=K, S, T, or V; Xaa18=I,
      K, T, or V; Xaa19=C, L, or N; Xaa20=I, T or V; Xaa21=A or E; and
      Xa23 is E, P, or T

<400> SEQUENCE: 3

Gly Xaa Xaa Xaa Xaa Xaa Xaa Xaa Xaa Xaa Xaa Xaa Xaa Xaa Xaa
 1               5                  10                  15

Xaa Xaa Xaa Xaa Xaa Arg Xaa
                20

<210> SEQ ID NO 4
<211> LENGTH: 6
<212> TYPE: PRT
<213> ORGANISM: Chlamydia trachomatis

<400> SEQUENCE: 4

Ala Gly Thr Glu Ala Ala
 1               5

<210> SEQ ID NO 5
<211> LENGTH: 6
<212> TYPE: PRT
<213> ORGANISM: Chlamydia trachomatis

<400> SEQUENCE: 5

Ala Gly Thr Asp Ala Ala
 1               5

<210> SEQ ID NO 6
<211> LENGTH: 26
<212> TYPE: PRT
<213> ORGANISM: Chlamydia trachomatis

<400> SEQUENCE: 6

Ala Glu Thr Ile Phe Asp Val Thr Thr Leu Asn Pro Thr Ile Ala Gly
 1               5                  10                  15

Ala Gly Asp Val Lys Thr Ser Ala Glu Gly
                20                  25

<210> SEQ ID NO 7
<211> LENGTH: 25
<212> TYPE: PRT
<213> ORGANISM: Chlamydia trachomatis

<400> SEQUENCE: 7

Ala Glu Thr Ile Leu Asp Val Thr Thr Leu Asn Pro Thr Ile Ala Gly
 1               5                  10                  15

Lys Gly Thr Val Val Thr Ser Ala Glu
                20                  25

<210> SEQ ID NO 8
<211> LENGTH: 10
<212> TYPE: PRT
<213> ORGANISM: Chlamydia trachomatis

<400> SEQUENCE: 8

Thr Thr Leu Asn Pro Thr Ile Ala Gly Cys
```

```
                1               5                  10
```

<210> SEQ ID NO 9
<211> LENGTH: 21
<212> TYPE: PRT
<213> ORGANISM: Chlamydia trachomatis

<400> SEQUENCE: 9

```
Gly Ala Lys Pro Thr Ala Thr Thr Gly Asn Ala Thr Ala Pro Ser Thr
  1               5                  10                  15

Leu Thr Ala Arg Glu
             20
```

<210> SEQ ID NO 10
<211> LENGTH: 13
<212> TYPE: PRT
<213> ORGANISM: Chlamydia trachomatis

<400> SEQUENCE: 10

```
Thr Thr Ser Asp Val Ala Gly Leu Gln Asn Asp Pro Cys
  1               5                  10
```

<210> SEQ ID NO 11
<211> LENGTH: 15
<212> TYPE: PRT
<213> ORGANISM: Chlamydia trachomatis

<400> SEQUENCE: 11

```
Ser Glu Phe Thr Ile Asn Lys Pro Lys Gly Tyr Val Gly Lys Glu
  1               5                  10                  15
```

<210> SEQ ID NO 12
<211> LENGTH: 16
<212> TYPE: PRT
<213> ORGANISM: Chlamydia trachomatis

<400> SEQUENCE: 12

```
Ile Leu Trp Glu Gly Phe Gly Gly Asp Pro Cys Asp Pro Cys Thr Thr
  1               5                  10                  15
```

<210> SEQ ID NO 13
<211> LENGTH: 10
<212> TYPE: PRT
<213> ORGANISM: Chlamydia trachomatis

<400> SEQUENCE: 13

```
Ala Leu Asn Ile Trp Asp Arg Phe Asp Val
  1               5                  10
```

<210> SEQ ID NO 14
<211> LENGTH: 25
<212> TYPE: PRT
<213> ORGANISM: Chlamydia trachomatis

<400> SEQUENCE: 14

```
Lys Met Lys Ser Arg Lys Ser Cys Gly Ile Ala Val Gly Thr Thr Val
  1               5                  10                  15

Val Ser Ala Asp Lys Tyr Ala Val Thr
             20                  25
```

<210> SEQ ID NO 15
<211> LENGTH: 28
<212> TYPE: PRT
<213> ORGANISM: Chlamydia trachomatis

```
<400> SEQUENCE: 15

Cys Ala Glu Thr Ile Phe Asp Val Thr Leu Asn Pro Thr Ile Ala
 1               5                  10                  15

Gly Ala Gly Asp Val Lys Thr Ser Ala Glu Gly Cys
            20                  25

<210> SEQ ID NO 16
<211> LENGTH: 27
<212> TYPE: PRT
<213> ORGANISM: Chlamydia trachomatis

<400> SEQUENCE: 16

Cys Ala Glu Thr Ile Leu Asp Val Thr Leu Asn Pro Thr Ile Ala
 1               5                  10                  15

Gly Lys Gly Thr Val Val Thr Ser Ala Glu Cys
            20                  25

<210> SEQ ID NO 17
<211> LENGTH: 11
<212> TYPE: PRT
<213> ORGANISM: Chlamydia trachomatis

<400> SEQUENCE: 17

Cys Thr Thr Leu Asn Pro Thr Ile Ala Gly Cys
 1               5                  10

<210> SEQ ID NO 18
<211> LENGTH: 23
<212> TYPE: PRT
<213> ORGANISM: Chlamydia trachomatis

<400> SEQUENCE: 18

Cys Gly Ala Lys Pro Thr Ala Thr Thr Gly Asn Ala Thr Ala Pro Ser
 1               5                  10                  15

Thr Leu Thr Ala Arg Glu Cys
            20

<210> SEQ ID NO 19
<211> LENGTH: 14
<212> TYPE: PRT
<213> ORGANISM: Chlamydia trachomatis

<400> SEQUENCE: 19

Cys Thr Thr Ser Asp Val Ala Gly Leu Gln Asn Asp Pro Cys
 1               5                  10

<210> SEQ ID NO 20
<211> LENGTH: 4
<212> TYPE: PRT
<213> ORGANISM: Chlamydia trachomatis

<400> SEQUENCE: 20

Arg Asp Glu Leu
 1

<210> SEQ ID NO 21
<211> LENGTH: 4
<212> TYPE: PRT
<213> ORGANISM: Chlamydia trachomatis

<400> SEQUENCE: 21

Lys Asp Glu Leu
 1
```

```
<210> SEQ ID NO 22
<211> LENGTH: 240
<212> TYPE: PRT
<213> ORGANISM: Pseudomonas aeruginosa
<220> FEATURE:
<223> OTHER INFORMATION: Description of sequence: Domain I

<400> SEQUENCE: 22

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

<210> SEQ ID NO 23
<211> LENGTH: 633
<212> TYPE: PRT
<213> ORGANISM: Pseudomonas aeruginosa
<220> FEATURE:
<223> OTHER INFORMATION: Description of sequence: Domain I

<400> SEQUENCE: 23

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80
```

```
Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Ala Glu Thr Ile Phe Asp Val Thr Thr Leu Asn Pro
370                 375                 380

Thr Ile Ala Gly Ala Gly Asp Val Lys Thr Ser Ala Glu Gly Cys Ala
385                 390                 395                 400

Gly Pro Ala Asp Ser Gly Asp Ala Leu Leu Glu Arg Asn Tyr Pro Thr
                405                 410                 415

Gly Ala Glu Phe Leu Gly Asp Gly Asp Val Ser Phe Ser Thr Arg
            420                 425                 430

Gly Thr Gln Asn Trp Thr Val Glu Arg Leu Leu Gln Ala His Arg Gln
        435                 440                 445

Leu Glu Glu Arg Gly Tyr Val Phe Val Gly Tyr His Gly Thr Phe Leu
    450                 455                 460

Glu Ala Ala Gln Ser Ile Val Phe Gly Gly Val Arg Ala Arg Ser Gln
465                 470                 475                 480

Asp Leu Asp Ala Ile Trp Arg Gly Phe Tyr Ile Ala Gly Asp Pro Ala
                485                 490                 495

Leu Ala Tyr Gly Tyr Ala Gln Asp Gln Glu Pro Asp Ala Arg Gly Arg
            500                 505                 510
```

```
Ile Arg Asn Gly Ala Leu Leu Arg Val Tyr Val Pro Arg Ser Ser Leu
        515                 520                 525

Pro Gly Phe Tyr Arg Thr Ser Leu Thr Leu Ala Ala Pro Glu Ala Ala
        530                 535                 540

Gly Glu Val Glu Arg Leu Ile Gly His Pro Leu Pro Leu Arg Leu Asp
545                 550                 555                 560

Ala Ile Thr Gly Pro Glu Glu Gly Arg Leu Glu Thr Ile Leu
            565                 570                 575

Gly Trp Pro Leu Ala Glu Arg Thr Val Val Ile Pro Ser Ala Ile Pro
            580                 585                 590

Thr Asp Pro Arg Asn Val Gly Gly Asp Leu Asp Pro Ser Ile Pro
            595                 600                 605

Asp Lys Glu Gln Ala Ile Ser Ala Leu Pro Asp Tyr Ala Ser Gln Pro
        610                 615                 620

Gly Lys Pro Pro Arg Glu Asp Leu Lys
625                 630

<210> SEQ ID NO 24
<211> LENGTH: 613
<212> TYPE: PRT
<213> ORGANISM: Pseudomonas aeruginosa
<220> FEATURE:
<223> OTHER INFORMATION: Description of sequence: Domain I

<400> SEQUENCE: 24

Ala Glu Glu Ala Phe Asp Leu Trp Asn Glu Cys Ala Lys Ala Cys Val
  1               5                  10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240
```

```
Pro Thr Val Ile Ser His Arg Leu His Phe Pro Glu Gly Gly Ser Leu
            245                 250                 255

Ala Ala Leu Thr Ala His Gln Ala Cys His Leu Pro Leu Glu Thr Phe
        260                 265                 270

Thr Arg His Arg Gln Pro Arg Gly Trp Glu Gln Leu Glu Gln Cys Gly
    275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Asn Ala Asp Val Val
                355                 360                 365

Ser Leu Thr Cys Ala Gly Thr Glu Ala Ala Cys Ala Gly Pro Ala Asp
        370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610

<210> SEQ ID NO 25
<211> LENGTH: 613
<212> TYPE: PRT
<213> ORGANISM: Pseudomonas aeruginosa
<220> FEATURE:
<223> OTHER INFORMATION: Description of sequence: Domain I
```

```
<400> SEQUENCE: 25

Ala Glu Glu Ala Phe Asp Leu Trp Asn Glu Cys Ala Lys Ala Cys Val
 1               5                  10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Asn Ala Asp Val Val
        355                 360                 365

Ser Leu Thr Cys Ala Gly Thr Asp Ala Ala Cys Ala Gly Pro Ala Asp
370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415
```

-continued

```
Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
                435                 440                 445

Ser Ile Val Phe Gly Gly Val Arg Ala Arg Ser Gln Asp Leu Asp Ala
450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
                500                 505                 510

Arg Thr Ser Leu Thr Leu Ala Ala Pro Glu Ala Ala Gly Glu Val Glu
            515                 520                 525

Arg Leu Ile Gly His Pro Leu Pro Leu Arg Leu Asp Ala Ile Thr Gly
            530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
                580                 585                 590

Ala Ile Ser Ala Leu Pro Asp Tyr Ala Ser Gln Pro Gly Lys Pro Pro
            595                 600                 605

Arg Glu Asp Leu Lys
        610

<210> SEQ ID NO 26
<211> LENGTH: 632
<212> TYPE: PRT
<213> ORGANISM: Pseudomonas aeruginosa
<220> FEATURE:
<223> OTHER INFORMATION: Description of sequence: Domain I

<400> SEQUENCE: 26

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
```

```
                        165                 170                 175
Ala Gln Thr Gln Pro Arg Arg Glu Lys Arg Trp Ser Glu Trp Ala Ser
                180                 185                 190

Gly Lys Val Leu Cys Leu Leu Asp Pro Leu Asp Gly Val Tyr Asn Tyr
            195                 200                 205

Leu Ala Gln Gln Arg Cys Asn Leu Asp Asp Thr Trp Glu Gly Lys Ile
        210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Ala Glu Thr Ile Leu Asp Val Thr Thr Leu Asn Pro
370                 375                 380

Thr Ile Ala Gly Lys Gly Thr Val Val Thr Ser Ala Glu Cys Ala Gly
385                 390                 395                 400

Pro Ala Asp Ser Gly Asp Ala Leu Leu Glu Arg Asn Tyr Pro Thr Gly
                405                 410                 415

Ala Glu Phe Leu Gly Asp Gly Gly Asp Val Ser Phe Ser Thr Arg Gly
            420                 425                 430

Thr Gln Asn Trp Thr Val Glu Arg Leu Leu Gln Ala His Arg Gln Leu
        435                 440                 445

Glu Glu Arg Gly Tyr Val Phe Val Gly Tyr His Gly Thr Phe Leu Glu
450                 455                 460

Ala Ala Gln Ser Ile Val Phe Gly Gly Val Arg Ala Arg Ser Gln Asp
465                 470                 475                 480

Leu Asp Ala Ile Trp Arg Gly Phe Tyr Ile Ala Gly Asp Pro Ala Leu
                485                 490                 495

Ala Tyr Gly Tyr Ala Gln Asp Gln Glu Pro Asp Ala Arg Gly Arg Ile
            500                 505                 510

Arg Asn Gly Ala Leu Leu Arg Val Tyr Val Pro Arg Ser Ser Leu Pro
        515                 520                 525

Gly Phe Tyr Arg Thr Ser Leu Thr Leu Ala Ala Pro Glu Ala Ala Gly
530                 535                 540

Glu Val Glu Arg Leu Ile Gly His Pro Leu Pro Leu Arg Leu Asp Ala
545                 550                 555                 560

Ile Thr Gly Pro Glu Glu Gly Gly Arg Leu Glu Thr Ile Leu Gly
                565                 570                 575

Trp Pro Leu Ala Glu Arg Thr Val Val Ile Pro Ser Ala Ile Pro Thr
            580                 585                 590
```

```
Asp Pro Arg Asn Val Gly Gly Asp Leu Asp Pro Ser Ser Ile Pro Asp
            595                 600                 605

Lys Glu Gln Ala Ile Ser Ala Leu Pro Asp Tyr Ala Ser Gln Pro Gly
        610                 615                 620

Lys Pro Pro Arg Glu Asp Leu Lys
625                 630

<210> SEQ ID NO 27
<211> LENGTH: 617
<212> TYPE: PRT
<213> ORGANISM: Pseudomonas aeruginosa
<220> FEATURE:
<223> OTHER INFORMATION: Description of sequence: Domain I

<400> SEQUENCE: 27

Ala Glu Glu Ala Phe Asp Leu Trp Asn Glu Cys Ala Lys Ala Cys Val
  1               5                  10                  15

Leu Asp Leu Lys Asp Gly Val Arg Ser Ser Arg Met Ser Val Asp Pro
             20                  25                  30

Ala Ile Ala Asp Thr Asn Gly Gln Gly Val Leu His Tyr Ser Met Val
         35                  40                  45

Leu Glu Gly Gly Asn Asp Ala Leu Lys Leu Ala Ile Asp Asn Ala Leu
 50                  55                  60

Ser Ile Thr Ser Asp Gly Leu Thr Ile Arg Leu Glu Gly Gly Val Glu
 65                  70                  75                  80

Pro Asn Lys Pro Val Arg Tyr Ser Tyr Thr Arg Gln Ala Arg Gly Ser
                 85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
```

```
                    325                 330                 335
Arg Leu Ala Leu Thr Leu Ala Ala Glu Ser Glu Arg Phe Val Arg
                340                 345                 350

Gln Gly Thr Gly Asn Asp Glu Ala Gly Ala Asn Ala Asp Val Val
                355                 360                 365

Ser Leu Thr Cys Thr Thr Leu Asn Pro Thr Ile Ala Gly Cys Cys Ala
    370                 375                 380

Gly Pro Ala Asp Ser Gly Asp Ala Leu Leu Glu Arg Asn Tyr Pro Thr
385                 390                 395                 400

Gly Ala Glu Phe Leu Gly Asp Gly Gly Asp Val Ser Phe Ser Thr Arg
                405                 410                 415

Gly Thr Gln Asn Trp Thr Val Glu Arg Leu Leu Gln Ala His Arg Gln
                420                 425                 430

Leu Glu Glu Arg Gly Tyr Val Phe Val Gly Tyr His Gly Thr Phe Leu
                435                 440                 445

Glu Ala Ala Gln Ser Ile Val Phe Gly Gly Val Arg Ala Arg Ser Gln
                450                 455                 460

Asp Leu Asp Ala Ile Trp Arg Gly Phe Tyr Ile Ala Gly Asp Pro Ala
465                 470                 475                 480

Leu Ala Tyr Gly Tyr Ala Gln Asp Gln Glu Pro Asp Ala Arg Gly Arg
                485                 490                 495

Ile Arg Asn Gly Ala Leu Leu Arg Val Tyr Val Pro Arg Ser Ser Leu
                500                 505                 510

Pro Gly Phe Tyr Arg Thr Ser Leu Thr Leu Ala Ala Pro Glu Ala Ala
                515                 520                 525

Gly Glu Val Glu Arg Leu Ile Gly His Pro Leu Pro Leu Arg Leu Asp
                530                 535                 540

Ala Ile Thr Gly Pro Glu Glu Gly Gly Arg Leu Glu Thr Ile Leu
545                 550                 555                 560

Gly Trp Pro Leu Ala Glu Arg Thr Val Val Ile Pro Ser Ala Ile Pro
                565                 570                 575

Thr Asp Pro Arg Asn Val Gly Gly Asp Leu Asp Pro Ser Ser Ile Pro
                580                 585                 590

Asp Lys Glu Gln Ala Ile Ser Ala Leu Pro Asp Tyr Ala Ser Gln Pro
            595                 600                 605

Gly Lys Pro Pro Arg Glu Asp Leu Lys
        610                 615

<210> SEQ ID NO 28
<211> LENGTH: 628
<212> TYPE: PRT
<213> ORGANISM: Pseudomonas aeruginosa
<220> FEATURE:
<223> OTHER INFORMATION: Description of sequence: Domain I

<400> SEQUENCE: 28

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
                20                  25                  30

Ala Ile Ala Asp Thr Asn Gly Gln Gly Val Leu His Tyr Ser Met Val
            35                  40                  45

Leu Glu Gly Gly Asn Asp Ala Leu Lys Leu Ala Ile Asp Asn Ala Leu
        50                  55                  60

Ser Ile Thr Ser Asp Gly Leu Thr Ile Arg Leu Glu Gly Gly Val Glu
65                  70                  75                  80
```

```
Pro Asn Lys Pro Val Arg Tyr Ser Tyr Thr Arg Gln Ala Arg Gly Ser
             85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
            115                 120                 125

Met Ser Pro Ile Tyr Thr Ile Glu Met Gly Asp Glu Leu Leu Ala Lys
            130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
                180                 185                 190

Gly Lys Val Leu Cys Leu Leu Asp Pro Leu Asp Gly Val Tyr Asn Tyr
            195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
                260                 265                 270

Thr Arg His Arg Gln Pro Arg Gly Trp Glu Gln Leu Glu Gln Cys Gly
            275                 280                 285

Tyr Pro Val Gln Arg Leu Val Ala Leu Tyr Leu Ala Ala Arg Leu Ser
            290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
                340                 345                 350

Gln Gly Thr Gly Asn Asp Glu Ala Gly Ala Ala Asn Ala Asp Val Val
            355                 360                 365

Ser Leu Thr Cys Gly Ala Lys Pro Thr Ala Thr Gly Asn Ala Thr
            370                 375                 380

Ala Pro Ser Thr Leu Thr Ala Arg Glu Cys Ala Gly Pro Ala Asp Ser
385                 390                 395                 400

Gly Asp Ala Leu Leu Glu Arg Asn Tyr Pro Thr Gly Ala Glu Phe Leu
                405                 410                 415

Gly Asp Gly Gly Asp Val Ser Phe Ser Thr Arg Gly Thr Gln Asn Trp
            420                 425                 430

Thr Val Glu Arg Leu Leu Gln Ala His Arg Gln Leu Glu Glu Arg Gly
            435                 440                 445

Tyr Val Phe Val Gly Tyr His Gly Thr Phe Leu Glu Ala Ala Gln Ser
            450                 455                 460

Ile Val Phe Gly Gly Val Arg Ala Arg Ser Gln Asp Leu Asp Ala Ile
465                 470                 475                 480

Trp Arg Gly Phe Tyr Ile Ala Gly Asp Pro Ala Leu Ala Tyr Gly Tyr
                485                 490                 495

Ala Gln Asp Gln Glu Pro Asp Ala Arg Gly Arg Ile Arg Asn Gly Ala
```

```
                    500                 505                 510
Leu Leu Arg Val Tyr Val Pro Arg Ser Ser Leu Pro Gly Phe Tyr Arg
                515                 520                 525

Thr Ser Leu Thr Leu Ala Ala Pro Glu Ala Ala Gly Glu Val Glu Arg
            530                 535                 540

Leu Ile Gly His Pro Leu Pro Leu Arg Leu Asp Ala Ile Thr Gly Pro
545                 550                 555                 560

Glu Glu Glu Gly Gly Arg Leu Glu Thr Ile Leu Gly Trp Pro Leu Ala
                565                 570                 575

Glu Arg Thr Val Val Ile Pro Ser Ala Ile Pro Thr Asp Pro Arg Asn
            580                 585                 590

Val Gly Gly Asp Leu Asp Pro Ser Ser Ile Pro Asp Lys Glu Gln Ala
                595                 600                 605

Ile Ser Ala Leu Pro Asp Tyr Ala Ser Gln Pro Gly Lys Pro Pro Arg
            610                 615                 620

Glu Asp Leu Lys
625

<210> SEQ ID NO 29
<211> LENGTH: 620
<212> TYPE: PRT
<213> ORGANISM: Pseudomonas aeruginosa
<220> FEATURE:
<223> OTHER INFORMATION: Description of sequence: Domain I

<400> SEQUENCE: 29

Ala Glu Glu Ala Phe Asp Leu Trp Asn Glu Cys Ala Lys Ala Cys Val
  1               5                  10                  15

Leu Asp Leu Lys Asp Gly Val Arg Ser Ser Arg Met Ser Val Asp Pro
                 20                  25                  30

Ala Ile Ala Asp Thr Asn Gly Gln Gly Val Leu His Tyr Ser Met Val
             35                  40                  45

Leu Glu Gly Gly Asn Asp Ala Leu Lys Leu Ala Ile Asp Asn Ala Leu
 50                  55                  60

Ser Ile Thr Ser Asp Gly Leu Thr Ile Arg Leu Glu Gly Gly Val Glu
 65                  70                  75                  80

Pro Asn Lys Pro Val Arg Tyr Ser Tyr Thr Arg Gln Ala Arg Gly Ser
                 85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
            115                 120                 125

Met Ser Pro Ile Tyr Thr Ile Glu Met Gly Asp Glu Leu Leu Ala Lys
            130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
            195                 200                 205

Leu Ala Gln Gln Arg Cys Asn Leu Asp Asp Thr Trp Glu Gly Lys Ile
            210                 215                 220

Tyr Arg Val Leu Ala Gly Asn Pro Ala Lys His Asp Leu Asp Ile Lys
225                 230                 235                 240
```

Pro Thr Val Ile Ser His Arg Leu His Phe Pro Glu Gly Gly Ser Leu
            245                 250                 255

Ala Ala Leu Thr Ala His Gln Ala Cys His Leu Pro Leu Glu Thr Phe
        260                 265                 270

Thr Arg His Arg Gln Pro Arg Gly Trp Glu Gln Leu Glu Gln Cys Gly
    275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Thr Thr Ser Asp Val Ala Gly Leu Gln Asn Asp Pro
    370                 375                 380

Cys Cys Ala Gly Pro Ala Asp Ser Gly Asp Ala Leu Leu Glu Arg Asn
385                 390                 395                 400

Tyr Pro Thr Gly Ala Glu Phe Leu Gly Asp Gly Gly Asp Val Ser Phe
                405                 410                 415

Ser Thr Arg Gly Thr Gln Asn Trp Thr Val Glu Arg Leu Leu Gln Ala
            420                 425                 430

His Arg Gln Leu Glu Glu Arg Gly Tyr Val Phe Val Gly Tyr His Gly
        435                 440                 445

Thr Phe Leu Glu Ala Ala Gln Ser Ile Val Phe Gly Val Arg Ala
    450                 455                 460

Arg Ser Gln Asp Leu Asp Ala Ile Trp Arg Gly Phe Tyr Ile Ala Gly
465                 470                 475                 480

Asp Pro Ala Leu Ala Tyr Gly Tyr Ala Gln Asp Gln Glu Pro Asp Ala
                485                 490                 495

Arg Gly Arg Ile Arg Asn Gly Ala Leu Leu Arg Val Tyr Val Pro Arg
            500                 505                 510

Ser Ser Leu Pro Gly Phe Tyr Arg Thr Ser Leu Thr Leu Ala Ala Pro
        515                 520                 525

Glu Ala Ala Gly Glu Val Glu Arg Leu Ile Gly His Pro Leu Pro Leu
    530                 535                 540

Arg Leu Asp Ala Ile Thr Gly Pro Glu Glu Glu Gly Gly Arg Leu Glu
545                 550                 555                 560

Thr Ile Leu Gly Trp Pro Leu Ala Glu Arg Thr Val Val Ile Pro Ser
                565                 570                 575

Ala Ile Pro Thr Asp Pro Arg Asn Val Gly Gly Asp Leu Asp Pro Ser
            580                 585                 590

Ser Ile Pro Asp Lys Glu Gln Ala Ile Ser Ala Leu Pro Asp Tyr Ala
        595                 600                 605

Ser Gln Pro Gly Lys Pro Pro Arg Glu Asp Leu Lys
    610                 615                 620

<210> SEQ ID NO 30
<211> LENGTH: 622
<212> TYPE: PRT
<213> ORGANISM: Pseudomonas aeruginosa
<220> FEATURE:
<223> OTHER INFORMATION: Description of sequence: Domain I

<400> SEQUENCE: 30

```
Ala Glu Glu Ala Phe Asp Leu Trp Asn Glu Cys Ala Lys Ala Cys Val
 1               5                  10                  15

Leu Asp Leu Lys Asp Gly Val Arg Ser Ser Arg Met Ser Val Asp Pro
             20                  25                  30

Ala Ile Ala Asp Thr Asn Gly Gln Gly Val Leu His Tyr Ser Met Val
         35                  40                  45

Leu Glu Gly Gly Asn Asp Ala Leu Lys Leu Ala Ile Asp Asn Ala Leu
 50                  55                  60

Ser Ile Thr Ser Asp Gly Leu Thr Ile Arg Leu Glu Gly Gly Val Glu
 65                  70                  75                  80

Pro Asn Lys Pro Val Arg Tyr Ser Tyr Thr Arg Gln Ala Arg Gly Ser
                 85                  90                  95

Trp Ser Leu Asn Trp Leu Val Pro Ile Gly His Glu Lys Pro Ser Asn
                100                 105                 110

Ile Lys Val Phe Ile His Glu Leu Asn Ala Gly Asn Gln Leu Ser His
            115                 120                 125

Met Ser Pro Ile Tyr Thr Ile Glu Met Gly Asp Glu Leu Leu Ala Lys
130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Asn Ala Asp Val Val
            355                 360                 365

Ser Leu Thr Cys Ser Glu Phe Thr Ile Asn Lys Pro Lys Gly Tyr Val
        370                 375                 380

Gly Lys Glu Cys Ala Gly Pro Ala Asp Ser Gly Asp Ala Leu Leu Glu
385                 390                 395                 400

Arg Asn Tyr Pro Thr Gly Ala Glu Phe Leu Gly Asp Gly Gly Asp Val
                405                 410                 415
```

```
Ser Phe Ser Thr Arg Gly Thr Gln Asn Trp Thr Val Glu Arg Leu Leu
            420                 425                 430

Gln Ala His Arg Gln Leu Glu Glu Arg Gly Tyr Val Phe Val Gly Tyr
            435                 440                 445

His Gly Thr Phe Leu Glu Ala Ala Gln Ser Ile Val Phe Gly Gly Val
            450                 455                 460

Arg Ala Arg Ser Gln Asp Leu Asp Ala Ile Trp Arg Gly Phe Tyr Ile
465                 470                 475                 480

Ala Gly Asp Pro Ala Leu Ala Tyr Gly Tyr Ala Gln Asp Gln Glu Pro
            485                 490                 495

Asp Ala Arg Gly Arg Ile Arg Asn Gly Ala Leu Leu Arg Val Tyr Val
            500                 505                 510

Pro Arg Ser Ser Leu Pro Gly Phe Tyr Arg Thr Ser Leu Thr Leu Ala
            515                 520                 525

Ala Pro Glu Ala Ala Gly Glu Val Glu Arg Leu Ile Gly His Pro Leu
            530                 535                 540

Pro Leu Arg Leu Asp Ala Ile Thr Gly Pro Glu Glu Gly Gly Arg
545                 550                 555                 560

Leu Glu Thr Ile Leu Gly Trp Pro Leu Ala Glu Arg Thr Val Val Ile
            565                 570                 575

Pro Ser Ala Ile Pro Thr Asp Pro Arg Asn Val Gly Gly Asp Leu Asp
            580                 585                 590

Pro Ser Ser Ile Pro Asp Lys Glu Gln Ala Ile Ser Ala Leu Pro Asp
            595                 600                 605

Tyr Ala Ser Gln Pro Gly Lys Pro Pro Arg Glu Asp Leu Lys
            610                 615                 620

<210> SEQ ID NO 31
<211> LENGTH: 623
<212> TYPE: PRT
<213> ORGANISM: Pseudomonas aeruginosa
<220> FEATURE:
<223> OTHER INFORMATION: Description of sequence: Domain I

<400> SEQUENCE: 31

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
            35                  40                  45

Leu Glu Gly Gly Asn Asp Ala Leu Lys Leu Ala Ile Asp Asn Ala Leu
50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
            85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
            115                 120                 125

Met Ser Pro Ile Tyr Thr Ile Glu Met Gly Asp Glu Leu Leu Ala Lys
            130                 135                 140

Leu Ala Arg Asp Ala Thr Phe Phe Val Arg Ala His Glu Ser Asn Glu
145                 150                 155                 160
```

-continued

```
Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Ile Leu Trp Glu Gly Phe Gly Gly Asp Pro Cys Asp
    370                 375                 380

Pro Cys Thr Thr Cys Ala Gly Pro Ala Asp Ser Gly Asp Ala Leu Leu
385                 390                 395                 400

Glu Arg Asn Tyr Pro Thr Gly Ala Glu Phe Leu Gly Asp Gly Gly Asp
                405                 410                 415

Val Ser Phe Ser Thr Arg Gly Thr Gln Asn Trp Thr Val Glu Arg Leu
            420                 425                 430

Leu Gln Ala His Arg Gln Leu Glu Glu Arg Gly Tyr Val Phe Val Gly
        435                 440                 445

Tyr His Gly Thr Phe Leu Glu Ala Ala Gln Ser Ile Val Phe Gly Gly
    450                 455                 460

Val Arg Ala Arg Ser Gln Asp Leu Asp Ala Ile Trp Arg Gly Phe Tyr
465                 470                 475                 480

Ile Ala Gly Asp Pro Ala Leu Ala Tyr Gly Tyr Ala Gln Asp Gln Glu
                485                 490                 495

Pro Asp Ala Arg Gly Arg Ile Arg Asn Gly Ala Leu Leu Arg Val Tyr
            500                 505                 510

Val Pro Arg Ser Ser Leu Pro Gly Phe Tyr Arg Thr Ser Leu Thr Leu
        515                 520                 525

Ala Ala Pro Glu Ala Ala Gly Glu Val Glu Arg Leu Ile Gly His Pro
    530                 535                 540

Leu Pro Leu Arg Leu Asp Ala Ile Thr Gly Pro Glu Glu Gly Gly
545                 550                 555                 560

Arg Leu Glu Thr Ile Leu Gly Trp Pro Leu Ala Glu Arg Thr Val Val
                565                 570                 575

Ile Pro Ser Ala Ile Pro Thr Asp Pro Arg Asn Val Gly Gly Asp Leu
            580                 585                 590
```

```
Asp Pro Ser Ser Ile Pro Asp Lys Glu Gln Ala Ile Ser Ala Leu Pro
        595                 600                 605
Asp Tyr Ala Ser Gln Pro Gly Lys Pro Pro Arg Glu Asp Leu Lys
        610                 615                 620

<210> SEQ ID NO 32
<211> LENGTH: 617
<212> TYPE: PRT
<213> ORGANISM: Pseudomonas aeruginosa
<220> FEATURE:
<223> OTHER INFORMATION: Description of sequence: Domain I

<400> SEQUENCE: 32

Ala Glu Glu Ala Phe Asp Leu Trp Asn Glu Cys Ala Lys Ala Cys Val
1               5                   10                  15
Leu Asp Leu Lys Asp Gly Val Arg Ser Ser Arg Met Ser Val Asp Pro
                20                  25                  30
Ala Ile Ala Asp Thr Asn Gly Gln Gly Val Leu His Tyr Ser Met Val
        35                  40                  45
Leu Glu Gly Gly Asn Asp Ala Leu Lys Leu Ala Ile Asp Asn Ala Leu
    50                  55                  60
Ser Ile Thr Ser Asp Gly Leu Thr Ile Arg Leu Glu Gly Gly Val Glu
65                  70                  75                  80
Pro Asn Lys Pro Val Arg Tyr Ser Tyr Thr Arg Gln Ala Arg Gly Ser
                85                  90                  95
Trp Ser Leu Asn Trp Leu Val Pro Ile Gly His Glu Lys Pro Ser Asn
            100                 105                 110
Ile Lys Val Phe Ile His Glu Leu Asn Ala Gly Asn Gln Leu Ser His
        115                 120                 125
Met Ser Pro Ile Tyr Thr Ile Glu Met Gly Asp Glu Leu Leu Ala Lys
    130                 135                 140
Leu Ala Arg Asp Ala Thr Phe Phe Val Arg Ala His Glu Ser Asn Glu
145                 150                 155                 160
Met Gln Pro Thr Leu Ala Ile Ser His Ala Gly Val Ser Val Val Met
                165                 170                 175
Ala Gln Thr Gln Pro Arg Arg Glu Lys Arg Trp Ser Glu Trp Ala Ser
            180                 185                 190
Gly Lys Val Leu Cys Leu Leu Asp Pro Leu Asp Gly Val Tyr Asn Tyr
        195                 200                 205
Leu Ala Gln Gln Arg Cys Asn Leu Asp Asp Thr Trp Glu Gly Lys Ile
    210                 215                 220
Tyr Arg Val Leu Ala Gly Asn Pro Ala Lys His Asp Leu Asp Ile Lys
225                 230                 235                 240
Pro Thr Val Ile Ser His Arg Leu His Phe Pro Glu Gly Gly Ser Leu
                245                 250                 255
Ala Ala Leu Thr Ala His Gln Ala Cys His Leu Pro Leu Glu Thr Phe
            260                 265                 270
Thr Arg His Arg Gln Pro Arg Gly Trp Glu Gln Leu Glu Gln Cys Gly
        275                 280                 285
Tyr Pro Val Gln Arg Leu Val Ala Leu Tyr Leu Ala Ala Arg Leu Ser
    290                 295                 300
Trp Asn Gln Val Asp Gln Val Ile Arg Asn Ala Leu Ala Ser Pro Gly
305                 310                 315                 320
Ser Gly Gly Asp Leu Gly Glu Ala Ile Arg Glu Gln Pro Glu Gln Ala
                325                 330                 335
```

```
Arg Leu Ala Leu Thr Leu Ala Ala Glu Ser Glu Arg Phe Val Arg
         340                 345                 350

Gln Gly Thr Gly Asn Asp Glu Ala Gly Ala Asn Ala Asp Val Val
         355                 360                 365

Ser Leu Thr Cys Ala Leu Asn Ile Trp Asp Arg Phe Asp Val Cys Ala
370                 375                 380

Gly Pro Ala Asp Ser Gly Asp Ala Leu Leu Glu Arg Asn Tyr Pro Thr
385                 390                 395                 400

Gly Ala Glu Phe Leu Gly Asp Gly Asp Val Ser Phe Ser Thr Arg
                 405                 410                 415

Gly Thr Gln Asn Trp Thr Val Glu Arg Leu Leu Gln Ala His Arg Gln
                 420                 425                 430

Leu Glu Glu Arg Gly Tyr Val Phe Val Gly Tyr His Gly Thr Phe Leu
                 435                 440                 445

Glu Ala Ala Gln Ser Ile Val Phe Gly Gly Val Arg Ala Arg Ser Gln
         450                 455                 460

Asp Leu Asp Ala Ile Trp Arg Gly Phe Tyr Ile Ala Gly Asp Pro Ala
465                 470                 475                 480

Leu Ala Tyr Gly Tyr Ala Gln Asp Gln Glu Pro Asp Ala Arg Gly Arg
                 485                 490                 495

Ile Arg Asn Gly Ala Leu Leu Arg Val Tyr Val Pro Arg Ser Ser Leu
                 500                 505                 510

Pro Gly Phe Tyr Arg Thr Ser Leu Thr Leu Ala Ala Pro Glu Ala Ala
                 515                 520                 525

Gly Glu Val Glu Arg Leu Ile Gly His Pro Leu Pro Leu Arg Leu Asp
         530                 535                 540

Ala Ile Thr Gly Pro Glu Glu Gly Gly Arg Leu Glu Thr Ile Leu
545                 550                 555                 560

Gly Trp Pro Leu Ala Glu Arg Thr Val Val Ile Pro Ser Ala Ile Pro
                 565                 570                 575

Thr Asp Pro Arg Asn Val Gly Gly Asp Leu Asp Pro Ser Ser Ile Pro
                 580                 585                 590

Asp Lys Glu Gln Ala Ile Ser Ala Leu Pro Asp Tyr Ala Ser Gln Pro
         595                 600                 605

Gly Lys Pro Pro Arg Glu Asp Leu Lys
    610                 615

<210> SEQ ID NO 33
<211> LENGTH: 632
<212> TYPE: PRT
<213> ORGANISM: Pseudomonas aeruginosa
<220> FEATURE:
<223> OTHER INFORMATION: Description of sequence: Domain I

<400> SEQUENCE: 33

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
                 20                  25                  30

Ala Ile Ala Asp Thr Asn Gly Gln Gly Val Leu His Tyr Ser Met Val
             35                  40                  45

Leu Glu Gly Gly Asn Asp Ala Leu Lys Leu Ala Ile Asp Asn Ala Leu
         50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
```

```
                        85                  90                  95
Trp Ser Leu Asn Trp Leu Val Pro Ile Gly His Glu Lys Pro Ser Asn
                100                 105                 110
Ile Lys Val Phe Ile His Glu Leu Asn Ala Gly Asn Gln Leu Ser His
            115                 120                 125
Met Ser Pro Ile Tyr Thr Ile Glu Met Gly Asp Glu Leu Leu Ala Lys
        130                 135                 140
Leu Ala Arg Asp Ala Thr Phe Phe Val Arg Ala His Glu Ser Asn Glu
145                 150                 155                 160
Met Gln Pro Thr Leu Ala Ile Ser His Ala Gly Val Ser Val Val Met
                165                 170                 175
Ala Gln Thr Gln Pro Arg Arg Glu Lys Arg Trp Ser Glu Trp Ala Ser
                180                 185                 190
Gly Lys Val Leu Cys Leu Leu Asp Pro Leu Asp Gly Val Tyr Asn Tyr
            195                 200                 205
Leu Ala Gln Gln Arg Cys Asn Leu Asp Asp Thr Trp Glu Gly Lys Ile
        210                 215                 220
Tyr Arg Val Leu Ala Gly Asn Pro Ala Lys His Asp Leu Asp Ile Lys
225                 230                 235                 240
Pro Thr Val Ile Ser His Arg Leu His Phe Pro Glu Gly Gly Ser Leu
                245                 250                 255
Ala Ala Leu Thr Ala His Gln Ala Cys His Leu Pro Leu Glu Thr Phe
            260                 265                 270
Thr Arg His Arg Gln Pro Arg Gly Trp Glu Gln Leu Glu Gln Cys Gly
        275                 280                 285
Tyr Pro Val Gln Arg Leu Val Ala Leu Tyr Leu Ala Ala Arg Leu Ser
        290                 295                 300
Trp Asn Gln Val Asp Gln Val Ile Arg Asn Ala Leu Ala Ser Pro Gly
305                 310                 315                 320
Ser Gly Gly Asp Leu Gly Glu Ala Ile Arg Glu Gln Pro Glu Gln Ala
                325                 330                 335
Arg Leu Ala Leu Thr Leu Ala Ala Ala Glu Ser Glu Arg Phe Val Arg
            340                 345                 350
Gln Gly Thr Gly Asn Asp Glu Ala Gly Ala Ala Asn Ala Asp Val Val
        355                 360                 365
Ser Leu Thr Cys Lys Met Lys Ser Arg Lys Ser Cys Gly Ile Ala Val
        370                 375                 380
Gly Thr Thr Val Val Ser Ala Asp Lys Tyr Ala Val Thr Cys Ala Gly
385                 390                 395                 400
Pro Ala Asp Ser Gly Asp Ala Leu Leu Glu Arg Asn Tyr Pro Thr Gly
                405                 410                 415
Ala Glu Phe Leu Gly Asp Gly Gly Asp Val Ser Phe Ser Thr Arg Gly
            420                 425                 430
Thr Gln Asn Trp Thr Val Glu Arg Leu Leu Gln Ala His Arg Gln Leu
        435                 440                 445
Glu Glu Arg Gly Tyr Val Phe Val Gly Tyr His Gly Thr Phe Leu Glu
        450                 455                 460
Ala Ala Gln Ser Ile Val Phe Gly Gly Val Arg Ala Arg Ser Gln Asp
465                 470                 475                 480
Leu Asp Ala Ile Trp Arg Gly Phe Tyr Ile Ala Gly Asp Pro Ala Leu
                485                 490                 495
Ala Tyr Gly Tyr Ala Gln Asp Gln Glu Pro Asp Ala Arg Gly Arg Ile
                500                 505                 510
```

```
Arg Asn Gly Ala Leu Leu Arg Val Tyr Val Pro Arg Ser Ser Leu Pro
            515                 520                 525

Gly Phe Tyr Arg Thr Ser Leu Thr Leu Ala Ala Pro Glu Ala Ala Gly
        530                 535                 540

Glu Val Glu Arg Leu Ile Gly His Pro Leu Pro Leu Arg Leu Asp Ala
545                 550                 555                 560

Ile Thr Gly Pro Glu Glu Gly Gly Arg Leu Glu Thr Ile Leu Gly
                565                 570                 575

Trp Pro Leu Ala Glu Arg Thr Val Val Ile Pro Ser Ala Ile Pro Thr
            580                 585                 590

Asp Pro Arg Asn Val Gly Gly Asp Leu Asp Pro Ser Ser Ile Pro Asp
            595                 600                 605

Lys Glu Gln Ala Ile Ser Ala Leu Pro Asp Tyr Ala Ser Gln Pro Gly
    610                 615                 620

Lys Pro Pro Arg Glu Asp Leu Lys
625                 630

<210> SEQ ID NO 34
<211> LENGTH: 155
<212> TYPE: PRT
<213> ORGANISM: Pseudomonas aeruginosa
<220> FEATURE:
<223> OTHER INFORMATION: Description of sequence: Domain II

<400> SEQUENCE: 34

Pro Thr Val Ile Ser His Arg Leu His Phe Pro Glu Gly Gly Ser Leu
1               5                   10                  15

Ala Ala Leu Thr Ala His Gln Ala Cys His Leu Pro Leu Glu Thr Phe
            20                  25                  30

Thr Arg His Arg Gln Pro Arg Gly Trp Glu Gln Leu Glu Gln Cys Gly
        35                  40                  45

Tyr Pro Val Gln Arg Leu Val Ala Leu Tyr Leu Ala Ala Arg Leu Ser
    50                  55                  60

Trp Asn Gln Val Asp Gln Val Ile Arg Asn Ala Leu Ala Ser Pro Gly
65                  70                  75                  80

Ser Gly Gly Asp Leu Gly Glu Ala Ile Arg Glu Gln Pro Glu Gln Ala
                85                  90                  95

Arg Leu Ala Leu Thr Leu Ala Ala Ala Glu Ser Glu Arg Phe Val Arg
            100                 105                 110

Gln Gly Thr Gly Asn Asp Glu Ala Gly Ala Ala Asn Ala Asp Val Val
        115                 120                 125

Ser Leu Thr Cys Pro Val Ala Ala Gly Glu Cys Ala Gly Pro Ala Asp
    130                 135                 140

Ser Gly Asp Ala Leu Leu Glu Arg Asn Tyr Pro
145                 150                 155

<210> SEQ ID NO 35
<211> LENGTH: 5
<212> TYPE: PRT
<213> ORGANISM: Artificial Sequence
<220> FEATURE:
<223> OTHER INFORMATION: Pseudomonas exotoxin chimeric immunogen ER
      retention signal

<400> SEQUENCE: 35

Arg Glu Asp Leu Lys
1               5

<210> SEQ ID NO 36
```

-continued

```
<211> LENGTH: 3
<212> TYPE: PRT
<213> ORGANISM: Chlamydia trachomatis

<400> SEQUENCE: 36

Gln Leu Gly
1

<210> SEQ ID NO 37
<211> LENGTH: 7
<212> TYPE: PRT
<213> ORGANISM: Chlamydia trachomatis

<400> SEQUENCE: 37

Ser Ala Glu Gly Gln Leu Gly
1               5

<210> SEQ ID NO 38
<211> LENGTH: 6
<212> TYPE: PRT
<213> ORGANISM: Chlamydia trachomatis

<400> SEQUENCE: 38

Gly Thr Asp Glu Leu Ala
1               5

<210> SEQ ID NO 39
<211> LENGTH: 9
<212> TYPE: PRT
<213> ORGANISM: Chlamydia trachomatis

<400> SEQUENCE: 39

Ala Glu Cys Gly Thr Asp Glu Leu Ala
1               5

<210> SEQ ID NO 40
<211> LENGTH: 7
<212> TYPE: PRT
<213> ORGANISM: Chlamydia trachomatis

<400> SEQUENCE: 40

Thr Thr Asn Val Ala Arg Pro
1               5

<210> SEQ ID NO 41
<211> LENGTH: 1839
<212> TYPE: DNA
<213> ORGANISM: Pseudomonas aeruginosa

<400> SEQUENCE: 41
gccgaagaag ctttcgacct ctggaacgaa tgcgccaaag cctgcgtgct cgacctcaag      60
gacggcgtgc gttccagccg catgagcgtc gacccggcca tcgccgacac caacggccag     120
ggcgtgctgc actactccat ggtcctggag gcggcaacg acgcgctcaa gctggccatc      180
gacaacgccc tcagcatcac cagcgacggc ctgaccatcc gcctcgaagg cggcgtcgag     240
ccgaacaagc cggtgcgcta cagctacacg cgccaggcgc gcggcagttg gtcgctgaac     300
tggctggtac cgatcggcca cgagaagccc tcgaacatca aggtgttcat ccacgaactg     360
aacgccggca accagctcag ccacatgtcg ccgatctaca ccatcgagat gggcgacgag     420
ttgctggcga agctggcgcg cgatgccacc ttcttcgtca gggcgcacga gagcaacgag     480
atgcagccga cgctcgccat cagccatgcc ggggtcagcg tggtcatggc ccagacccag     540
ccgcgccggg aaaagcgctg gagcgaatgg gccagcggca aggtgttgtg cctgctcgac     600
```

-continued

```
ccgctggacg gggtctacaa ctacctcgcc cagcaacgct gcaacctcga cgatacctgg      660
gaaggcaaga tctaccgggt gctcgccggc aacccggcga agcatgacct ggacatcaaa      720
cccacggtca tcagtcatcg cctgcacttt cccgagggcg gcagcctggc cgcgctgacc      780
gcgcaccagg cttgccacct gccgctggag actttcaccc gtcatcgcca gccgcgcggc      840
tgggaacaac tggagcagtg cggctatccg gtgcagcggc tggtcgccct ctacctggcg      900
gcgcggctgt cgtggaacca ggtcgaccag gtgatccgca cgccctggc cagccccggc       960 agcggcggcg acctgggcga agcgatccgc gagcagccgg agcaggcccg tctggccctg     1020
accctggccg ccgccgagag cgagcgcttc gtccggcagg caccggcaa cgacgaggcc      1080 ggcgcggcca cgccgacgt ggtgagcctg acctgcccgg tcgccgccgg tgaatgcgcg      1140
ggcccggcgg acagcggcga cgccctgctg agcgcaact atcccactgg cgcggagttc      1200
ctcggcgacg gcggcgacgt cagcttcagc acccgcggca cgcagaactg acggtggag      1260 cggctgctcc aggcgcaccg ccaactggag gagcgcggct atgtgttcgt cggctaccac     1320
ggcaccttcc tcgaagcggc gcaaagcatc gtcttcggcg gggtgcgcgc gcgcagccag     1380
gacctcgacg cgatctggcg cggttttctat atcgccggcg atccggcgct ggcctacggc    1440
tacgcccagg accaggaacc cgacgcacgc ggccggatcc gcaacggtgc cctgctgcgg    1500
gtctatgtgc cgcgctcgag cctgccggc ttctaccgca ccagcctgac cctggccgcg     1560
ccggaggcgg cgggcgaggt cgaacggctg atcgccatc cgctgccgct cgcctggac     1620 gccatcaccg ccccgagga ggaaggcggg cgcctggaga ccattctcgg ctggccgctg     1680
gccgagcgca ccgtggtgat tccctcggcg atccccaccg acccgcgcaa cgtcggcggc    1740
gacctcgacc cgtccagcat ccccgacaag gaacaggcga tcagcgccct gccggactac    1800
gccagccagc cggcaaaacc gccgcgcgag gacctgaag                           1839
```

<210> SEQ ID NO 42
<211> LENGTH: 27
<212> TYPE: PRT
<213> ORGANISM: Artificial Sequence
<220> FEATURE:
<223> OTHER INFORMATION: Formula I for construct C. trachomatis antigen
<220> FEATURE:
<221> NAME/KEY: VARIANT
<222> LOCATION: 1, 2, 3, 4, 5, 6
<223> OTHER INFORMATION: Xaa1= A, V, or absent; Xaa2= E, T, K, or
      absent; Xaa3= A, T, P, or absent; Xaa4= I, V, or absent;
      Xaa5 is F, L, V, or absent; Xaa6= D or absent
<220> FEATURE:
<221> NAME/KEY: VARIANT
<222> LOCATION: 7, 12, 14, 15, 17, 18, 19, 20
<223> OTHER INFORMATION: Xaa7= V, T, I, or absent; Xaa12= P or R;
      Xaa14= T or I; Xaa15= A or T; Xaa17= A, C, K, or absent;
      Xaa18= G or absent; Xaa19= S, G, T, A, E, D, or absent; Xaa20=
      V or absent;
<220> FEATURE:
<221> NAME/KEY: VARIANT
<222> LOCATION: 21, 22, 23, 24, 25, 26, 27
<223> OTHER INFORMATION: Xaa21= A, V, I, K, or absent; Xaa22= A, G, S,
      T, or absent; Xaa23= A, G, N, S, or absent; Xaa24= G, N, or
      absent; Xaa25= A, S, T, or absent; Xaa26= D, E, or absent; and
      Xaa27 is G, N, or absent

<400> SEQUENCE: 42

Xaa Xaa Xaa Xaa Xaa Xaa Xaa Thr Thr Leu Asn Xaa Thr Xaa Xaa Gly
1               5                   10                  15

Xaa Xaa Xaa Xaa Xaa Xaa Xaa Xaa Xaa Xaa Xaa
            20                  25

<210> SEQ ID NO 43
<211> LENGTH: 20
<212> TYPE: PRT
<213> ORGANISM: Chlamydia trachomatis

<400> SEQUENCE: 43

Ala Lys Pro Thr Ala Thr Thr Gly Asn Ala Thr Ala Pro Ser Thr Leu
1               5                   10                  15

Thr Ala Arg Glu
            20

<210> SEQ ID NO 44
<211> LENGTH: 22
<212> TYPE: PRT
<213> ORGANISM: Chlamydia trachomatis

<400> SEQUENCE: 44

Asn Asn Glu Asn Gln Thr Lys Val Ser Asn Ser Thr Phe Val Pro Asn
1               5                   10                  15

Met Ser Leu Asp Gln Ser
            20

<210> SEQ ID NO 45
<211> LENGTH: 14
<212> TYPE: PRT
<213> ORGANISM: Chlamydia trachomatis

<400> SEQUENCE: 45

Lys Glu Leu Pro Leu Asp Leu Thr Ser Gly Thr Asp Ala Ala
1               5                   10

<210> SEQ ID NO 46
<211> LENGTH: 30
<212> TYPE: PRT
<213> ORGANISM: Chlamydia trachomatis

<400> SEQUENCE: 46

Ser Ala Glu Thr Ile Phe Asp Val Thr Thr Leu Asn Pro Thr Ile Ala
1               5                   10                  15

Gly Ala Gly Asp Val Lys Thr Ser Ala Glu Gly Gln Leu Gly
            20                  25                  30

<210> SEQ ID NO 47
<211> LENGTH: 20
<212> TYPE: PRT
<213> ORGANISM: Chlamydia trachomatis

<400> SEQUENCE: 47

Ala Lys Pro Thr Thr Asp Thr Gly Asn Ser Ala Ala Pro Ser Thr Leu
1               5                   10                  15

Thr Ala Arg Glu
            20

<210> SEQ ID NO 48
<211> LENGTH: 21
<212> TYPE: PRT
<213> ORGANISM: Chlamydia trachomatis

<400> SEQUENCE: 48

Asp Asn Glu Asn Gln Lys Thr Val Lys Ala Glu Ser Val Pro Asn Met
1               5                   10                  15

Ser Phe Asp Gln Ser
            20

```
<210> SEQ ID NO 49
<211> LENGTH: 14
<212> TYPE: PRT
<213> ORGANISM: Chlamydia trachomatis

<400> SEQUENCE: 49

Lys Glu Phe Pro Leu Asp Leu Thr Ala Gly Thr Asp Ala Ala
1               5                   10

<210> SEQ ID NO 50
<211> LENGTH: 30
<212> TYPE: PRT
<213> ORGANISM: Chlamydia trachomatis

<400> SEQUENCE: 50

Ser Ala Thr Ala Ile Phe Asp Thr Thr Thr Leu Asn Pro Thr Ile Ala
1               5                   10                  15

Gly Ala Gly Asp Val Lys Thr Gly Ala Glu Gly Gln Leu Gly
            20                  25                  30

<210> SEQ ID NO 51
<211> LENGTH: 20
<212> TYPE: PRT
<213> ORGANISM: Chlamydia trachomatis

<400> SEQUENCE: 51

Asp Lys Pro Thr Ser Thr Thr Gly Asn Ala Thr Ala Pro Thr Thr Leu
1               5                   10                  15

Thr Ala Arg Glu
            20

<210> SEQ ID NO 52
<211> LENGTH: 21
<212> TYPE: PRT
<213> ORGANISM: Chlamydia trachomatis

<400> SEQUENCE: 52

Asp Asn Glu Asn Gln Ser Thr Val Lys Thr Asn Ser Val Pro Asn Met
1               5                   10                  15

Ser Leu Asp Gln Ser
            20

<210> SEQ ID NO 53
<211> LENGTH: 14
<212> TYPE: PRT
<213> ORGANISM: Chlamydia trachomatis

<400> SEQUENCE: 53

Gln Glu Phe Pro Leu Ala Leu Ile Ala Gly Thr Asp Ala Ala
1               5                   10

<210> SEQ ID NO 54
<211> LENGTH: 30
<212> TYPE: PRT
<213> ORGANISM: Chlamydia trachomatis

<400> SEQUENCE: 54

Ser Ala Thr Ala Ile Phe Asp Thr Thr Thr Leu Asn Pro Thr Ile Ala
1               5                   10                  15

Gly Ala Gly Asp Val Lys Ala Ser Ala Glu Gly Gln Leu Gly
            20                  25                  30

<210> SEQ ID NO 55
```

```
<211> LENGTH: 21
<212> TYPE: PRT
<213> ORGANISM: Chlamydia trachomatis

<400> SEQUENCE: 55

Glu Ala Leu Ala Gly Ala Ser Gly Asn Thr Thr Ser Thr Leu Ser Lys
1               5                   10                  15

Leu Val Glu Arg Thr
            20

<210> SEQ ID NO 56
<211> LENGTH: 21
<212> TYPE: PRT
<213> ORGANISM: Chlamydia trachomatis

<400> SEQUENCE: 56

Asp Gly Val Asn Ala Thr Lys Pro Ala Ala Asp Ser Ile Pro Asn Val
1               5                   10                  15

Gln Leu Asn Gln Ser
            20

<210> SEQ ID NO 57
<211> LENGTH: 14
<212> TYPE: PRT
<213> ORGANISM: Chlamydia trachomatis

<400> SEQUENCE: 57

Lys Glu Phe Pro Leu Asp Leu Thr Ala Gly Thr Asp Ala Ala
1               5                   10

<210> SEQ ID NO 58
<211> LENGTH: 31
<212> TYPE: PRT
<213> ORGANISM: Chlamydia trachomatis

<400> SEQUENCE: 58

Leu Val Thr Pro Val Val Asp Ile Thr Thr Leu Asn Pro Thr Ile Ala
1               5                   10                  15

Gly Cys Gly Ser Val Ala Gly Ala Asn Thr Glu Gly Gln Ile Ser
            20                  25                  30

<210> SEQ ID NO 59
<211> LENGTH: 21
<212> TYPE: PRT
<213> ORGANISM: Chlamydia trachomatis

<400> SEQUENCE: 59

Glu Ala Leu Ala Gly Ala Ser Gly Asn Thr Thr Ser Thr Leu Ser Lys
1               5                   10                  15

Leu Val Glu Arg Thr
            20

<210> SEQ ID NO 60
<211> LENGTH: 21
<212> TYPE: PRT
<213> ORGANISM: Chlamydia trachomatis

<400> SEQUENCE: 60

Asp Gly Glu Asn Ala Thr Gln Pro Ala Ala Thr Ser Ile Pro Asn Val
1               5                   10                  15

Gln Leu Asn Gln Ser
            20
```

```
<210> SEQ ID NO 61
<211> LENGTH: 14
<212> TYPE: PRT
<213> ORGANISM: Chlamydia trachomatis

<400> SEQUENCE: 61

Gln Glu Phe Pro Leu Ala Leu Thr Ala Gly Thr Asp Ala Ala
1               5                   10

<210> SEQ ID NO 62
<211> LENGTH: 30
<212> TYPE: PRT
<213> ORGANISM: Chlamydia trachomatis

<400> SEQUENCE: 62

Leu Ala Lys Pro Val Val Asp Ile Thr Thr Leu Asn Pro Thr Ile Ala
1               5                   10                  15

Gly Cys Gly Ser Val Val Met Asn Ser Glu Gly Gln Ile Ser
            20                  25                  30

<210> SEQ ID NO 63
<211> LENGTH: 22
<212> TYPE: PRT
<213> ORGANISM: Chlamydia trachomatis

<400> SEQUENCE: 63

Ala Ala Pro Thr Thr Asn Asp Ala Ala Asp Leu Gln Asn Asp Pro Lys
1               5                   10                  15

Thr Asn Val Ala Arg Pro
            20

<210> SEQ ID NO 64
<211> LENGTH: 22
<212> TYPE: PRT
<213> ORGANISM: Chlamydia trachomatis

<400> SEQUENCE: 64

Thr Lys Thr Lys Ser Ser Asp Phe Asn Thr Ala Lys Leu Val Pro Asn
1               5                   10                  15

Ile Ala Leu Asn Arg Ala
            20

<210> SEQ ID NO 65
<211> LENGTH: 14
<212> TYPE: PRT
<213> ORGANISM: Chlamydia trachomatis

<400> SEQUENCE: 65

Ala Glu Phe Pro Leu Asp Ile Thr Ala Gly Thr Glu Ala Ala
1               5                   10

<210> SEQ ID NO 66
<211> LENGTH: 31
<212> TYPE: PRT
<213> ORGANISM: Chlamydia trachomatis

<400> SEQUENCE: 66

Leu Ala Glu Ala Ile Leu Asp Val Thr Thr Leu Asn Pro Thr Ile Ala
1               5                   10                  15

Gly Lys Gly Thr Val Val Ala Ser Gly Ser Asp Asn Asp Leu Ala
            20                  25                  30

<210> SEQ ID NO 67
<211> LENGTH: 22
```

```
<212> TYPE: PRT
<213> ORGANISM: Chlamydia trachomatis

<400> SEQUENCE: 67

Ala Ala Pro Thr Thr Lys Asp Val Ala Gly Leu Glu Asn Asp Pro Thr
1               5                   10                  15

Thr Asn Val Ala Arg Pro
            20

<210> SEQ ID NO 68
<211> LENGTH: 22
<212> TYPE: PRT
<213> ORGANISM: Chlamydia trachomatis

<400> SEQUENCE: 68

Thr Lys Thr Gln Ser Ser Asn Phe Asn Thr Ala Lys Leu Val Pro Asn
1               5                   10                  15

Ala Ala Leu Asn Gln Ala
            20

<210> SEQ ID NO 69
<211> LENGTH: 14
<212> TYPE: PRT
<213> ORGANISM: Chlamydia trachomatis

<400> SEQUENCE: 69

Ala Glu Phe Pro Leu Asp Ile Ile Ala Gly Thr Glu Ala Ala
1               5                   10

<210> SEQ ID NO 70
<211> LENGTH: 30
<212> TYPE: PRT
<213> ORGANISM: Chlamydia trachomatis

<400> SEQUENCE: 70

Leu Ala Glu Ala Ile Leu Asp Val Thr Thr Leu Asn Pro Thr Ile Ala
1               5                   10                  15

Gly Lys Gly Thr Val Val Ser Ser Ala Glu Asn Glu Leu Ala
            20                  25                  30

<210> SEQ ID NO 71
<211> LENGTH: 22
<212> TYPE: PRT
<213> ORGANISM: Chlamydia trachomatis

<400> SEQUENCE: 71

Ala Ala Pro Thr Thr Ser Asp Val Ala Gly Leu Gln Asn Asp Pro Thr
1               5                   10                  15

Thr Asn Val Ala Arg Pro
            20

<210> SEQ ID NO 72
<211> LENGTH: 22
<212> TYPE: PRT
<213> ORGANISM: Chlamydia trachomatis

<400> SEQUENCE: 72

Thr Lys Thr Gln Ala Ser Ser Phe Asn Thr Ala Asn Leu Phe Pro Asn
1               5                   10                  15

Thr Ala Leu Asn Gln Ala
            20

<210> SEQ ID NO 73
```

```
<211> LENGTH: 14
<212> TYPE: PRT
<213> ORGANISM: Chlamydia trachomatis

<400> SEQUENCE: 73

Ala Glu Phe Pro Leu Asp Ile Thr Ala Gly Thr Glu Ala Ala
1               5                   10

<210> SEQ ID NO 74
<211> LENGTH: 31
<212> TYPE: PRT
<213> ORGANISM: Chlamydia trachomatis

<400> SEQUENCE: 74

Leu Ala Glu Ala Ile Leu Asp Val Thr Thr Leu Asn Pro Thr Ile Ala
1               5                   10                  15

Gly Lys Gly Thr Val Val Ala Ser Gly Ser Glu Asn Asp Leu Ala
            20                  25                  30

<210> SEQ ID NO 75
<211> LENGTH: 22
<212> TYPE: PRT
<213> ORGANISM: Chlamydia trachomatis

<400> SEQUENCE: 75

Ala Ala Pro Thr Thr Ser Asp Val Glu Gly Leu Gln Asn Asp Pro Thr
1               5                   10                  15

Thr Asn Val Ala Arg Pro
            20

<210> SEQ ID NO 76
<211> LENGTH: 22
<212> TYPE: PRT
<213> ORGANISM: Chlamydia trachomatis

<400> SEQUENCE: 76

Thr Lys Thr Gln Tyr Ser Lys Phe Asn Thr Ala Asn Leu Val Pro Asn
1               5                   10                  15

Thr Ala Leu Asp Arg Ala
            20

<210> SEQ ID NO 77
<211> LENGTH: 14
<212> TYPE: PRT
<213> ORGANISM: Chlamydia trachomatis

<400> SEQUENCE: 77

Val Glu Phe Pro Leu Asp Ile Thr Ala Gly Thr Glu Ala Ala
1               5                   10

<210> SEQ ID NO 78
<211> LENGTH: 31
<212> TYPE: PRT
<213> ORGANISM: Chlamydia trachomatis

<400> SEQUENCE: 78

Leu Ala Glu Ala Ile Leu Asp Val Thr Thr Leu Asn Pro Thr Ile Thr
1               5                   10                  15

Gly Lys Gly Ala Val Val Ser Ser Gly Ser Asp Asn Glu Leu Ala
            20                  25                  30

<210> SEQ ID NO 79
<211> LENGTH: 22
<212> TYPE: PRT
```

```
<213> ORGANISM: Chlamydia trachomatis

<400> SEQUENCE: 79

Ala Glu Pro Thr Thr Ser Asp Thr Ala Gly Leu Ser Asn Asp Pro Thr
1               5                   10                  15

Thr Asn Val Ala Arg Pro
            20

<210> SEQ ID NO 80
<211> LENGTH: 22
<212> TYPE: PRT
<213> ORGANISM: Chlamydia trachomatis

<400> SEQUENCE: 80

Thr Lys Thr Gln Ser Thr Asn Phe Asn Thr Ala Lys Leu Val Pro Asn
1               5                   10                  15

Thr Ala Leu Asn Gln Ala
            20

<210> SEQ ID NO 81
<211> LENGTH: 14
<212> TYPE: PRT
<213> ORGANISM: Chlamydia trachomatis

<400> SEQUENCE: 81

Ala Glu Phe Pro Leu Asp Ile Thr Ala Gly Thr Glu Ala Ala
1               5                   10

<210> SEQ ID NO 82
<211> LENGTH: 31
<212> TYPE: PRT
<213> ORGANISM: Chlamydia trachomatis

<400> SEQUENCE: 82

Leu Ala Glu Ala Val Leu Asp Val Thr Thr Leu Asn Pro Thr Ile Ala
1               5                   10                  15

Gly Lys Gly Ser Val Val Ala Ser Gly Ser Glu Asn Glu Leu Ala
            20                  25                  30

<210> SEQ ID NO 83
<211> LENGTH: 30
<212> TYPE: PRT
<213> ORGANISM: Chlamydia trachomatis

<400> SEQUENCE: 83

Ser Ala Glu Thr Ile Phe Asp Val Thr Thr Leu Asn Pro Thr Ile Ala
1               5                   10                  15

Gly Ala Gly Asp Val Lys Thr Ser Ala Glu Gly Gln Leu Gly
            20                  25                  30

<210> SEQ ID NO 84
<211> LENGTH: 30
<212> TYPE: PRT
<213> ORGANISM: Chlamydia trachomatis

<400> SEQUENCE: 84

Ser Ala Thr Ala Ile Phe Asp Thr Thr Thr Leu Asn Pro Thr Ile Ala
1               5                   10                  15

Gly Ala Gly Asp Val Lys Thr Gly Ala Glu Gly Gln Leu Gly
            20                  25                  30

<210> SEQ ID NO 85
<211> LENGTH: 30
```

```
<212> TYPE: PRT
<213> ORGANISM: Chlamydia trachomatis

<400> SEQUENCE: 85

Ser Ala Thr Ala Ile Phe Asp Thr Thr Leu Asn Pro Thr Ile Ala
1               5                   10                  15

Gly Ala Gly Asp Val Lys Ala Ser Ala Glu Gly Gln Leu Gly
            20                  25                  30

<210> SEQ ID NO 86
<211> LENGTH: 30
<212> TYPE: PRT
<213> ORGANISM: Chlamydia trachomatis

<400> SEQUENCE: 86

Leu Ala Thr Ala Ile Phe Asp Thr Thr Thr Leu Asn Pro Thr Ile Ala
1               5                   10                  15

Gly Ala Gly Glu Val Lys Ala Asn Ala Glu Gly Gln Leu Gly
            20                  25                  30

<210> SEQ ID NO 87
<211> LENGTH: 30
<212> TYPE: PRT
<213> ORGANISM: Chlamydia trachomatis

<400> SEQUENCE: 87

Ser Ala Thr Thr Val Phe Asp Val Thr Thr Leu Asn Pro Thr Ile Ala
1               5                   10                  15

Gly Ala Gly Asp Val Lys Ala Ser Ala Glu Gly Gln Leu Gly
            20                  25                  30

<210> SEQ ID NO 88
<211> LENGTH: 31
<212> TYPE: PRT
<213> ORGANISM: Chlamydia trachomatis

<400> SEQUENCE: 88

Leu Val Thr Pro Val Val Asp Ile Thr Thr Leu Asn Pro Thr Ile Ala
1               5                   10                  15

Gly Cys Gly Ser Val Ala Gly Ala Asn Thr Glu Gly Gln Ile Ser
            20                  25                  30

<210> SEQ ID NO 89
<211> LENGTH: 31
<212> TYPE: PRT
<213> ORGANISM: Chlamydia trachomatis

<400> SEQUENCE: 89

Leu Ala Lys Pro Val Val Asp Ile Thr Thr Leu Asn Pro Thr Ile Ala
1               5                   10                  15

Gly Cys Gly Ser Val Val Ala Ala Asn Ser Glu Gly Gln Ile Ser
            20                  25                  30

<210> SEQ ID NO 90
<211> LENGTH: 31
<212> TYPE: PRT
<213> ORGANISM: Chlamydia trachomatis

<400> SEQUENCE: 90

Leu Ala Glu Ala Ile Leu Asp Val Thr Thr Leu Asn Pro Thr Ile Ala
1               5                   10                  15

Gly Lys Gly Ser Val Val Ser Ala Gly Thr Asp Asn Glu Leu Ala
            20                  25                  30
```

```
<210> SEQ ID NO 91
<211> LENGTH: 30
<212> TYPE: PRT
<213> ORGANISM: Chlamydia trachomatis

<400> SEQUENCE: 91

Leu Ala Lys Pro Val Leu Asp Thr Thr Thr Leu Asn Pro Thr Ile Ala
1               5                   10                  15

Gly Lys Gly Thr Val Val Ser Ser Ala Glu Asn Glu Leu Ala
            20                  25                  30

<210> SEQ ID NO 92
<211> LENGTH: 31
<212> TYPE: PRT
<213> ORGANISM: Chlamydia trachomatis

<400> SEQUENCE: 92

Leu Ala Glu Ala Ile Leu Asp Val Thr Thr Leu Asn Pro Thr Ile Ala
1               5                   10                  15

Gly Lys Gly Thr Val Val Ala Ser Gly Ser Asp Asn Asp Leu Ala
            20                  25                  30

<210> SEQ ID NO 93
<211> LENGTH: 30
<212> TYPE: PRT
<213> ORGANISM: Chlamydia trachomatis

<400> SEQUENCE: 93

Leu Ala Glu Ala Ile Leu Asp Val Thr Thr Leu Asn Pro Thr Ile Ala
1               5                   10                  15

Gly Lys Gly Thr Val Val Ser Ser Ala Glu Asn Glu Leu Ala
            20                  25                  30

<210> SEQ ID NO 94
<211> LENGTH: 31
<212> TYPE: PRT
<213> ORGANISM: Chlamydia trachomatis

<400> SEQUENCE: 94

Leu Ala Glu Ala Ile Leu Asp Val Thr Thr Leu Asn Pro Thr Ile Ala
1               5                   10                  15

Gly Lys Gly Thr Val Val Ala Ser Gly Ser Glu Asn Asp Leu Ala
            20                  25                  30

<210> SEQ ID NO 95
<211> LENGTH: 31
<212> TYPE: PRT
<213> ORGANISM: Chlamydia trachomatis

<400> SEQUENCE: 95

Leu Ala Glu Ala Ile Leu Asp Val Thr Thr Leu Asn Pro Thr Ile Thr
1               5                   10                  15

Gly Lys Gly Ala Val Val Ser Ser Gly Ser Asp Asn Glu Leu Ala
            20                  25                  30

<210> SEQ ID NO 96
<211> LENGTH: 31
<212> TYPE: PRT
<213> ORGANISM: Chlamydia trachomatis

<400> SEQUENCE: 96

Leu Ala Glu Ala Val Leu Asp Val Thr Thr Leu Asn Pro Thr Ile Ala
```

```
                    1               5                   10                  15
Gly Lys Gly Ser Val Val Ala Ser Gly Ser Glu Asn Glu Leu Ala
                20                  25                  30

<210> SEQ ID NO 97
<211> LENGTH: 11
<212> TYPE: PRT
<213> ORGANISM: Chlamydia trachomatis

<400> SEQUENCE: 97

Val Leu Gln Thr Asp Val Asn Lys Glu Phe Gln
1               5                   10

<210> SEQ ID NO 98
<211> LENGTH: 638
<212> TYPE: PRT
<213> ORGANISM: Pseudomonas aeruginosa

<400> SEQUENCE: 98

Met His Leu Ile Pro His Trp Ile Pro Leu Val Ala Ser Leu Gly Leu
1               5                   10                  15

Leu Ala Gly Gly Ser Ser Ala Ser Ala Ala Glu Glu Ala Phe Asp Leu
                20                  25                  30

Trp Asn Glu Cys Ala Lys Ala Cys Val Leu Asp Leu Lys Asp Gly Val
            35                  40                  45

Arg Ser Ser Arg Met Ser Val Asp Pro Ala Ile Ala Asp Thr Asn Gly
        50                  55                  60

Gln Gly Val Leu His Tyr Ser Met Val Leu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Thr Gln Pro Arg Arg
        195                 200                 205

Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
        275                 280                 285

Ala Cys His Leu Pro Leu Glu Thr Phe Thr Arg His Arg Gln Pro Arg
    290                 295                 300
```

-continued

```
Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
            325                 330                 335

Ile Arg Asn Ala Leu Ala Ser Pro Gly Ser Gly Gly Asp Leu Gly Glu
            340                 345                 350

Ala Ile Arg Glu Gln Pro Glu Gln Ala Arg Leu Ala Leu Thr Leu Ala
            355                 360                 365

Ala Ala Glu Ser Glu Arg Phe Val Arg Gln Gly Thr Gly Asn Asp Glu
            370             375                 380

Ala Gly Ala Ala Asn Ala Asp Val Val Ser Leu Thr Cys Pro Val Ala
385             390                 395                 400

Ala Gly Glu Cys Ala Gly Pro Ala Asp Ser Gly Asp Ala Leu Leu Glu
            405                 410                 415

Arg Asn Tyr Pro Thr Gly Ala Glu Phe Leu Gly Asp Gly Gly Asp Val
            420                 425                 430

Ser Phe Ser Thr Arg Gly Thr Gln Asn Trp Thr Val Glu Arg Leu Leu
            435                 440                 445

Gln Ala His Arg Gln Leu Glu Arg Gly Tyr Val Phe Val Gly Tyr
            450                 455                 460

His Gly Thr Phe Leu Glu Ala Ala Gln Ser Ile Val Phe Gly Gly Val
465                 470                 475                 480

Arg Ala Arg Ser Gln Asp Leu Asp Ala Ile Trp Arg Gly Phe Tyr Ile
            485                 490                 495

Ala Gly Asp Pro Ala Leu Ala Tyr Gly Tyr Ala Gln Asp Gln Glu Pro
            500                 505                 510

Asp Ala Arg Gly Arg Ile Arg Asn Gly Ala Leu Leu Arg Val Tyr Val
            515                 520                 525

Pro Arg Ser Ser Leu Pro Gly Phe Tyr Arg Thr Ser Leu Thr Leu Ala
            530                 535                 540

Ala Pro Glu Ala Ala Gly Glu Val Glu Arg Leu Ile Gly His Pro Leu
545                 550                 555                 560

Pro Leu Arg Leu Asp Ala Ile Thr Gly Pro Glu Glu Gly Gly Arg
            565                 570                 575

Leu Glu Thr Ile Leu Gly Trp Pro Leu Ala Glu Arg Thr Val Val Ile
            580                 585                 590

Pro Ser Ala Ile Pro Thr Asp Pro Arg Asn Val Gly Gly Asp Leu Asp
            595                 600                 605

Pro Ser Ser Ile Pro Asp Lys Glu Gln Ala Ile Ser Ala Leu Pro Asp
610                 615                 620

Tyr Ala Ser Gln Pro Gly Lys Pro Pro Arg Glu Asp Leu Lys
625                 630                 635
```